US011596561B2

(12) United States Patent
Hammond et al.

(10) Patent No.: US 11,596,561 B2
(45) Date of Patent: Mar. 7, 2023

(54) ABSORBENT ARTICLE WITH AN EXUDATE MANAGEMENT LAYER

(71) Applicant: Kimberly-Clark Worldwide, Inc., Neenah, WI (US)

(72) Inventors: Andrew Thomas Hammond, Grand Chute, WI (US); Kyle Mark Barriger, Neenah, WI (US); Michael Douglas Sperl, Waupaca, WI (US); Russell J. Brumm, Menasha, WI (US); Suzanne Marie Schmoker, Oshkosh, WI (US); Heidi Bauerlein Hopkins, Neenah, WI (US); Alyssa Kimberly DeYoung, Chicago, IL (US); Ellen E. Pelky, De Pere, WI (US); Kimberly M. Downs, Ripon, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 792 days.

(21) Appl. No.: 16/492,198

(22) PCT Filed: Mar. 29, 2018

(86) PCT No.: PCT/US2018/025102
§ 371 (c)(1),
(2) Date: Sep. 9, 2019

(87) PCT Pub. No.: WO2018/183651
PCT Pub. Date: Oct. 4, 2018

(65) Prior Publication Data
US 2021/0137753 A1  May 13, 2021

Related U.S. Application Data

(60) Provisional application No. 62/479,861, filed on Mar. 31, 2017.

(51) Int. Cl.
*B32B 3/24* (2006.01)
*B32B 3/28* (2006.01)
(Continued)

(52) U.S. Cl.
CPC .... *A61F 13/53747* (2013.01); *A61F 13/5116* (2013.01); *A61F 13/51104* (2013.01);
(Continued)

(58) Field of Classification Search
None
See application file for complete search history.

(56) References Cited

U.S. PATENT DOCUMENTS 3,182,661 A * 5/1965 Ribeiro ............... A41B 13/04
604/347
3,441,023 A * 4/1969 Rijssenbeek ...... A61F 13/00012
604/378
(Continued)

FOREIGN PATENT DOCUMENTS

CN        1079382 A     12/1993
CN    101272757 A      9/2008
(Continued)

OTHER PUBLICATIONS

Co-pending U.S. Appl. No. 16/492,209, filed Sep. 9, 2019, by Schmoker et al. for "Absorbent Article with an Exudate Management Layer."
(Continued)

*Primary Examiner* — Jeffrey A Vonch
(74) *Attorney, Agent, or Firm* — Kimberly-Clark Worldwide, Inc.

(57) ABSTRACT

An absorbent article can have a topsheet layer, a liquid impermeable layer, and an absorbent core positioned between the topsheet layer and the liquid impermeable layer. The absorbent article can further include an exudate man-
(Continued)

agement layer in fluid communication with the topsheet layer. In various embodiments, the exudate management layer can be positioned on a body facing surface of the topsheet layer. In various embodiments, the exudate management layer can be positioned between the topsheet layer and the absorbent core. The exudate management layer has a first component which defines an opening for direct passage of body exudates into the absorbent core. The exudate management layer has a second component which at least partially overlaps the first component of the exudate management layer and further extends in the longitudinal direction of the absorbent article in a direction towards the posterior region of the absorbent article.

13 Claims, 21 Drawing Sheets

(51) Int. Cl.
*A61F 13/511* (2006.01)
*A61F 13/537* (2006.01)
*B32B 3/26* (2006.01)
*A61F 13/47* (2006.01)
*A61F 13/512* (2006.01)
*A61F 13/472* (2006.01)

(52) U.S. Cl.
CPC .... *A61F 13/5376* (2013.01); *A61F 13/53708* (2013.01); *B32B 3/263* (2013.01); *B32B 3/266* (2013.01); *A61F 13/47218* (2013.01); *A61F 13/511* (2013.01); *A61F 13/512* (2013.01); *A61F 13/537* (2013.01); *A61F 13/53713* (2013.01); *A61F 2013/51186* (2013.01); *A61F 2013/53765* (2013.01); *A61F 2013/53782* (2013.01); *A61F 2013/53786* (2013.01); *A61F 2013/53795* (2013.01); *B32B 3/28* (2013.01); *B32B 2555/02* (2013.01); *Y10T 428/24215* (2015.01); *Y10T 428/24281* (2015.01); *Y10T 428/24331* (2015.01); *Y10T 428/24479* (2015.01); *Y10T 428/24661* (2015.01); *Y10T 428/24669* (2015.01)

(56) References Cited

U.S. PATENT DOCUMENTS

| | | | | |
|---|---|---|---|---|
| 3,441,024 A * | 4/1969 | Ralph | A61F 13/64 | 604/401 |
| 3,532,093 A * | 10/1970 | Lovret | A61F 5/451 | 604/350 |
| 3,658,065 A * | 4/1972 | Hirsch | A61M 27/00 | 604/350 |
| 4,031,897 A * | 6/1977 | Graetz | A61F 5/455 | 604/397 |
| 4,595,441 A * | 6/1986 | Holvoet | A61F 13/539 | 156/554 |
| 4,605,405 A | 8/1986 | Lassen | | |
| 4,631,062 A | 12/1986 | Lassen et al. | | |
| 4,662,877 A * | 5/1987 | Williams | A61F 13/49473 | 604/385.27 |
| 4,673,403 A | 6/1987 | Lassen et al. | | |
| 4,743,245 A | 5/1988 | Lassen et al. | | |
| 4,790,839 A * | 12/1988 | Ahr | A61F 13/4752 | 604/378 |
| 4,804,380 A | 2/1989 | Lassen et al. | | |
| 4,846,824 A | 7/1989 | Lassen et al. | | |
| 4,886,509 A * | 12/1989 | Mattsson | A61F 13/471 | 604/389 |
| 4,968,312 A * | 11/1990 | Khan | A61F 13/551 | 604/385.13 |
| 4,988,344 A * | 1/1991 | Reising | A61F 13/53747 | 604/378 |
| 4,988,345 A * | 1/1991 | Reising | A61L 15/425 | 604/378 |
| 5,171,236 A * | 12/1992 | Dreier | A61F 13/495 | 604/385.19 |
| D342,785 S | 12/1993 | Farrell | | |
| 5,304,159 A * | 4/1994 | Tanji | A61F 13/51311 | 604/385.19 |
| 5,304,160 A * | 4/1994 | Igaue | A61F 13/4942 | 604/385.28 |
| 5,306,266 A * | 4/1994 | Freeland | A61F 13/49007 | 604/385.19 |
| 5,324,278 A * | 6/1994 | Visscher | A61F 13/5605 | 604/385.12 |
| 5,330,459 A * | 7/1994 | Lavon | A61F 13/495 | 604/385.12 |
| 5,342,342 A * | 8/1994 | Kitaoka | A61F 13/5116 | 604/385.19 |
| 5,415,640 A * | 5/1995 | Kirby | A61F 13/512 | 604/383 |
| 5,429,632 A * | 7/1995 | Tanji | A61F 13/5116 | 604/394 |
| 5,439,459 A * | 8/1995 | Tanji | A61F 13/49473 | 604/385.28 |
| 5,507,735 A | 4/1996 | Van Iten et al. | | |
| 5,514,121 A * | 5/1996 | Roe | A61F 13/495 | 604/385.19 |
| 5,531,730 A * | 7/1996 | Dreier | A61F 13/49406 | 604/385.19 |
| 5,554,142 A * | 9/1996 | Dreier | A61F 13/495 | 604/385.23 |
| 5,558,660 A * | 9/1996 | Dreier | A61F 13/49413 | 604/385.19 |
| 5,591,149 A * | 1/1997 | Cree | A61F 13/535 | 604/378 |
| 5,624,421 A * | 4/1997 | Dabi | A61F 13/53747 | 604/385.101 |
| 5,662,633 A * | 9/1997 | Doak | A61F 13/53743 | 604/378 |
| 5,681,300 A * | 10/1997 | Ahr | A61F 13/537 | 604/358 |
| 5,688,259 A | 11/1997 | Osborn et al. | | |
| 5,704,931 A * | 1/1998 | Holtman | A61F 13/45 | 604/397 |
| 5,728,084 A * | 3/1998 | Palumbo | A61F 13/53704 | 604/378 |
| 5,733,274 A * | 3/1998 | Osborn, III | A61F 13/511 | 604/385.04 |
| 5,833,677 A * | 11/1998 | Sauer | A61F 13/49466 | 604/378 |
| 5,846,230 A * | 12/1998 | Osborn, III | A61F 13/47227 | 604/378 |
| 5,849,003 A | 12/1998 | Olsen et al. | | |
| 5,853,403 A * | 12/1998 | Tanzer | A61F 13/495 | 604/385.19 |
| 5,954,705 A * | 9/1999 | Sawaki | A61F 13/47263 | 604/385.101 |
| 5,997,520 A * | 12/1999 | Ahr | A61F 13/511 | 604/385.12 |
| 6,017,336 A * | 1/2000 | Sauer | A61F 13/495 | 604/385.01 |
| 6,022,338 A * | 2/2000 | Putzer | A61F 13/495 | 604/385.01 |
| 6,110,158 A * | 8/2000 | Kielpikowski | A61F 13/49413 | 604/385.24 |
| 6,114,597 A * | 9/2000 | Romare | A61F 13/474 | 604/385.24 |
| 6,117,524 A * | 9/2000 | Hisanaka | A61F 13/512 | 428/137 |
| 6,168,583 B1 * | 1/2001 | Tanji | A61F 13/495 | 604/385.19 |
| 6,168,584 B1 * | 1/2001 | Allen | A61F 13/495 | 604/385.19 |
| 6,171,291 B1 | 1/2001 | Osborn, III et al. | | |

(56) References Cited

U.S. PATENT DOCUMENTS

| | | | |
|---|---|---|---|
| 6,241,714 B1* | 6/2001 | Raidel | A61F 13/53747 604/383 |
| 6,248,098 B1* | 6/2001 | Sayama | A61F 13/495 604/385.27 |
| 6,264,641 B1* | 7/2001 | Van Gompel | A61F 13/53708 604/385.01 |
| 6,293,935 B1* | 9/2001 | Kimura | A61F 13/47263 604/385.03 |
| 6,293,936 B1* | 9/2001 | Otsubo | A61F 13/496 604/396 |
| 6,296,628 B1* | 10/2001 | Mizutani | A61F 13/47263 604/385.03 |
| 6,365,794 B1 | 4/2002 | Dabi et al. | |
| 6,375,643 B1 | 4/2002 | Moorhead et al. | |
| 6,376,011 B1 | 4/2002 | Reeves et al. | |
| 6,409,883 B1 | 6/2002 | Makolin et al. | |
| 6,423,043 B1* | 7/2002 | Gustafsson | A61F 13/505 604/385.24 |
| 6,429,351 B1* | 8/2002 | Guidotti | A61F 13/535 604/385.01 |
| 6,432,097 B1* | 8/2002 | Ahr | A61F 13/82 604/362 |
| 6,450,998 B1* | 9/2002 | Otsubo | A61F 13/495 604/383 |
| 6,458,110 B1* | 10/2002 | Lavon | A61F 13/495 604/385.12 |
| 6,486,379 B1* | 11/2002 | Chen | A61F 13/5323 604/378 |
| 6,492,574 B1* | 12/2002 | Chen | A61F 13/47227 604/385.01 |
| 6,506,185 B1* | 1/2003 | Sauer | A61F 13/49466 604/385.101 |
| 6,527,756 B1* | 3/2003 | Mishima | A61F 13/495 604/385.27 |
| 6,551,297 B2* | 4/2003 | Tanaka | A61F 13/4752 604/385.24 |
| 6,575,948 B1* | 6/2003 | Kashiwagi | A61F 13/47218 604/385.101 |
| 6,595,972 B1* | 7/2003 | Wise | A61F 13/495 604/385.101 |
| 6,613,955 B1 | 9/2003 | Lindsay et al. | |
| 6,667,424 B1 | 12/2003 | Hamilton et al. | |
| 6,716,204 B1* | 4/2004 | D'Acchioli | A61F 13/495 604/385.03 |
| 6,726,668 B2* | 4/2004 | Underhill | A61F 13/42 604/383 |
| 6,955,667 B1* | 10/2005 | Tanaka | A61F 13/4752 604/385.03 |
| 7,037,298 B2 | 5/2006 | Ohshima et al. | |
| 7,056,312 B1* | 6/2006 | Metcalf | A61F 13/4752 604/385.04 |
| 7,122,023 B1* | 10/2006 | Hinoki | A61F 13/47254 604/383 |
| 7,166,095 B1* | 1/2007 | Coates | A61F 13/505 604/401 |
| 7,175,613 B2* | 2/2007 | Sugiyama | A61F 13/495 604/385.01 |
| 7,858,841 B2 | 12/2010 | Krautkramer et al. | |
| 7,967,801 B2 | 6/2011 | Hammons et al. | |
| 3,157,780 A1 | 4/2012 | Lira et al. | |
| 3,167,860 A1 | 5/2012 | Siegel | |
| 8,870,842 B2 | 10/2014 | Hill | |
| 8,915,898 B2 | 12/2014 | Dieringer et al. | |
| 9,066,837 B2 | 6/2015 | Kim et al. | |
| 9,308,138 B2 | 4/2016 | Andersson et al. | |
| 9,314,382 B2 | 4/2016 | Zilm | |
| 11,033,438 B2* | 6/2021 | Nickel | A61F 13/53409 |
| 2002/0010453 A1* | 1/2002 | Mishima | A61F 13/495 604/385.27 |
| 2002/0026170 A1* | 2/2002 | Samuelsson | A61F 13/47227 604/385.01 |
| 2002/0068920 A1* | 6/2002 | Mishima | A61F 13/4942 604/385.24 |
| 2002/0072726 A1* | 6/2002 | Mishima | A61F 13/495 604/385.24 |
| 2002/0082570 A1* | 6/2002 | Mishima | A61F 5/451 604/385.19 |
| 2002/0099351 A1* | 7/2002 | Onishi | A61F 13/495 604/385.19 |
| 2002/0120247 A1* | 8/2002 | Mizutani | A61F 13/47218 604/385.03 |
| 2002/0120248 A1* | 8/2002 | Onishi | A61F 13/49466 604/385.24 |
| 2003/0018314 A1 | 1/2003 | Nozaki et al. | |
| 2003/0125699 A1* | 7/2003 | Drevik | A61F 13/4704 604/385.31 |
| 2004/0019337 A1* | 1/2004 | Moberg-Alehammar | A61F 13/5323 604/385.03 |
| 2004/0039363 A1* | 2/2004 | Sugiyama | A61F 13/511 604/385.24 |
| 2004/0087919 A1* | 5/2004 | Tanaka | A61F 5/451 604/327 |
| 2005/0010185 A1* | 1/2005 | Mizutani | A61F 13/47227 604/385.03 |
| 2005/0027278 A1* | 2/2005 | Mizutani | A61F 13/505 604/387 |
| 2005/0113777 A1* | 5/2005 | Samuelsson | A61F 13/47227 604/385.01 |
| 2005/0131369 A1* | 6/2005 | Benson | A61F 13/47227 604/385.01 |
| 2005/0148960 A1* | 7/2005 | Price | A61F 13/4752 604/358 |
| 2005/0182382 A1* | 8/2005 | Bailey | A61F 13/495 604/385.101 |
| 2005/0224171 A1* | 10/2005 | Hoshika | A61F 13/15804 156/301 |
| 2005/0228357 A1* | 10/2005 | Mishima | A61F 13/493 604/385.19 |
| 2005/0228358 A1* | 10/2005 | Mishima | A61F 13/495 604/385.19 |
| 2005/0234418 A1 | 10/2005 | Yoshimasa et al. | |
| 2005/0256491 A1* | 11/2005 | Watanabe | A61F 13/78 604/385.13 |
| 2006/0287636 A1* | 12/2006 | Sakai | A61F 13/532 604/385.101 |
| 2007/0043330 A1* | 2/2007 | Lankhof | A61F 13/51394 604/378 |
| 2007/0073256 A1* | 3/2007 | Ponomarenko | A61F 13/5123 604/385.13 |
| 2007/0088302 A1* | 4/2007 | Sugiyama | A61F 13/49017 604/385.19 |
| 2008/0262460 A1 | 10/2008 | Li et al. | |
| 2009/0088716 A1 | 4/2009 | Nwokeji | |
| 2009/0204095 A1* | 8/2009 | McDaniel | A61F 13/47227 604/387 |
| 2009/0306614 A1* | 12/2009 | Boissier | A61F 13/5123 604/378 |
| 2009/0326495 A1* | 12/2009 | MacDonald | A61F 13/495 604/385.19 |
| 2010/0152692 A1* | 6/2010 | Ong | A61F 13/47263 604/367 |
| 2010/0225215 A1 | 9/2010 | Lee | |
| 2010/0228215 A1* | 9/2010 | Ponomarenko | A61F 13/495 604/374 |
| 2010/0256586 A1* | 10/2010 | Bergstrom | A61F 13/4702 604/385.24 |
| 2011/0060303 A1* | 3/2011 | Bissah | A61F 13/53756 604/374 |
| 2011/0183109 A1 | 7/2011 | Seyler et al. | |
| 2012/0143163 A1* | 6/2012 | Ng | A61F 13/4704 604/385.101 |
| 2012/0277701 A1* | 11/2012 | Stone | A61F 13/51476 604/367 |
| 2012/0277711 A1* | 11/2012 | Kim | A61F 13/535 604/374 |

(56) References Cited

U.S. PATENT DOCUMENTS

| | | | |
|---|---|---|---|
| 2012/0296303 A1* | 11/2012 | Ng | A61F 13/51305 604/378 |
| 2013/0231622 A1* | 9/2013 | Dieringer | A61F 13/47218 604/374 |
| 2014/0121624 A1* | 5/2014 | Kirby | A61F 13/51108 604/383 |
| 2014/0128828 A1* | 5/2014 | Andersson | A61F 13/53752 604/383 |
| 2014/0358106 A1 | 12/2014 | Tan et al. | |
| 2015/0057631 A1 | 2/2015 | Dieringer et al. | |
| 2015/0073372 A1* | 3/2015 | Hippe | B32B 7/05 604/385.16 |
| 2015/0094678 A1* | 4/2015 | O'Brien | A61F 13/51394 604/385.04 |
| 2015/0133884 A1* | 5/2015 | Hao | A61F 13/47218 604/385.01 |
| 2015/0216714 A1* | 8/2015 | Sasaki | A61F 5/451 604/385.19 |
| 2015/0313766 A1 | 11/2015 | Miao et al. | |
| 2015/0313771 A1 | 11/2015 | Bergstrom et al. | |
| 2015/0320616 A1* | 11/2015 | Schmitz | A61F 13/539 604/380 |
| 2016/0287450 A1 | 10/2016 | Andersson et al. | |
| 2016/0346137 A1* | 12/2016 | Villarreal | A61F 5/4401 |
| 2017/0246045 A1* | 8/2017 | Schmoker | A61F 13/537 |
| 2017/0246055 A1* | 8/2017 | Barnes | A61F 13/15747 |
| 2017/0252231 A1* | 9/2017 | Kim | A61F 13/537 |
| 2017/0354549 A1* | 12/2017 | Cho | A61F 13/472 |
| 2017/0354550 A1* | 12/2017 | Park | A61F 13/5116 |
| 2018/0064585 A1* | 3/2018 | Park | A61F 13/47272 |
| 2018/0098892 A1* | 4/2018 | Park | A61F 13/475 |
| 2019/0091076 A1* | 3/2019 | Joshi | A61F 13/15203 |
| 2019/0133833 A1* | 5/2019 | Park | A61F 13/53747 |
| 2019/0313524 A1* | 10/2019 | Huang | H01L 23/49838 |
| 2020/0008986 A1* | 1/2020 | Hopkins | A61F 13/49017 |
| 2020/0008988 A1* | 1/2020 | Schmoker | A61F 13/5116 |
| 2020/0030161 A1 | 1/2020 | Beitz et al. | |
| 2020/0038258 A1* | 2/2020 | Schmoker | A61F 13/537 |

FOREIGN PATENT DOCUMENTS

| | | | | |
|---|---|---|---|---|
| CN | 103221010 A | | 7/2013 | |
| CN | 104769173 A | | 7/2015 | |
| CN | 105232235 A | | 1/2016 | |
| CN | 105377205 A | | 3/2016 | |
| EP | 1048277 A2 | * | 11/2000 | A61F 13/472 |
| JP | 10314223 A | * | 12/1998 | A61F 13/4755 |
| JP | 2002345871 A | * | 12/2002 | |
| JP | 2006149464 A | * | 6/2006 | |
| JP | 2012115463 A | * | 6/2012 | |
| JP | 2014097257 A | * | 5/2014 | |
| WO | WO-9325172 A1 | * | 12/1993 | A61F 13/495 |
| WO | WO-0037002 A1 | * | 6/2000 | A61F 13/4702 |
| WO | 0228335 A1 | | 4/2002 | |
| WO | 05048899 A1 | | 6/2005 | |
| WO | WO-2008002220 A1 | * | 1/2008 | A61F 13/4755 |
| WO | 12137668 A1 | | 10/2012 | |
| WO | 2016002471 A1 | | 1/2016 | |
| WO | 16053230 A1 | | 4/2016 | |
| WO | 16108833 A1 | | 7/2016 | |
| WO | 16108856 A1 | | 7/2016 | |
| WO | WO-2016108833 A1 | * | 7/2016 | A61F 13/472 |
| WO | 16183709 A1 | | 11/2016 | |
| WO | WO-2016183709 A1 | * | 11/2016 | A61F 13/47236 |

OTHER PUBLICATIONS

Co-pending U.S. Appl. No. 16/492,204, filed Sep. 9, 2019, by Schmoker et al. for "Absorbent Article with an Exudate Management Layer."

* cited by examiner

ABSORBENT ARTICLE WITH AN EXUDATE MANAGEMENT LAYER

BACKGROUND OF THE DISCLOSURE

A primary function of a personal care absorbent article is to absorb and retain body exudates such as urine and fecal material with additional desired attributes including low leakage of the exudates from the absorbent article and a dry feel to the wearer of the absorbent article. Currently, a wide variety of products for absorbent of body exudates are available in the form of diapers, training pants, and incontinence devices. These products generally have an absorbent core positioned between a body-facing liquid permeable topsheet layer and a garment-facing liquid impermeable layer. The edges of the topsheet layer and the liquid impermeable layer are often bonded together at their periphery to form a seal to contain the absorbent core and body exudates received into the product through the topsheet layer. In use, such products may have a front waist and rear waist region which can encircle the lower torso of the wearer to remain in place on the body of the wearer.

Absorbent articles commonly fail, however, to prevent leakage of body exudates. Some body exudates, such as solid and semi-solid fecal material, have difficulty penetrating the topsheet layer of the absorbent article as easily as urine and tend to spread across the surface of the topsheet layer under the influence of gravity, motion, and pressure by the wearer of the absorbent article. The migration of such body exudates is often towards the perimeter of the absorbent article, increasing the likelihood of leakage and smears against the skin of the wearer which can make clean-up of the skin difficult.

An additional problem is that such conventional absorbent article products may not always have an adequate fit to the body of the wearer which can lead to increased levels of leakage of body exudates from the product and discomfort during wear of the product. Many conventional absorbent article products are flat or have flat regions prior to use while the wearer's body is contoured. Even though the flat absorbent article product can bend during use, it can still fail to fully conform to the body of the wearer which can result in gaps between the product and the skin of the wearer resulting in leakage of body exudates, particularly those body exudates, such as solid and semi-solid femal material, which have a more difficult time penetrating the topsheet layer of the product. The movement of the wearer can also cause undesirable deformation of the product and fold lines within the product which can create pathways along which the body exudates can travel and leak from the product.

There remains a need for an absorbent article that can adequately reduce the incidence of leakage of body exudates from the absorbent article. There remains a need for an absorbent article which can provide improved handling of body exudates. There remains a need for an absorbent article that can minimize the amount of body exudates in contact with the wearer's skin.

SUMMARY OF THE DISCLOSURE

In various embodiment, an absorbent article can have a longitudinal direction and a transverse direction; a longitudinal centerline and a transverse centerline; an anterior region, a posterior region, and a central region positioned between the anterior region and the posterior region; an anterior region transverse direction end edge, a posterior region transverse direction end edge, and a pair of longitudinal direction side edges extending between and connecting the anterior region transverse direction end edge and the posterior region transverse direction end edge; a topsheet layer defining a body facing surface of the absorbent article, a liquid impermeable layer defining a garment facing surface of the absorbent article, and an absorbent core positioned between the topsheet layer and the liquid impermeable layer; and an exudate management layer in fluid communication with the topsheet layer; the exudate management layer comprising a first component at least partially defining an opening in the exudate management layer; and a second component connected to the first component via a primary fold, the second component extending from the primary fold in the longitudinal direction towards the posterior region of the absorbent article, wherein the opening is positioned between the transverse centerline and the posterior region transverse direction end edge.

In various embodiments, the exudate management layer is positioned on the body facing surface of the topsheet layer. In various embodiments, the exudate management layer is positioned between the topsheet layer and the absorbent core.

In various embodiments, the absorbent article further has an acquisition layer.

In various embodiments, the second component comprises a secondary fold.

In various embodiments, the absorbent article further has a third component connected to the primary component of the exudate management layer via a third component primary fold. In various embodiments, the third component extends from the third component primary fold in the longitudinal direction towards the anterior region of the absorbent article.

In various embodiments, the second component at least partially overlaps the first component. In various embodiments, the second component at least partially underlaps the first component.

In various embodiments, the absorbent article further has an opposing pair of containment flaps extending in the longitudinal direction of the absorbent article.

In various embodiments, the topsheet layer is a fluid entangled laminate web comprising a support layer comprising a plurality of fibers and opposed first and second surfaces; a projection layer comprising a plurality of fibers and opposed inner and outer surfaces, the second surface of the support layer in contact with the inner surface of the projection layer, fibers of at least one of the support layer and the projection layer being fluid-entangled fibers of the other of the support layer and the projection layer; a plurality of hollow projections formed form a first plurality of the plurality of fibers in the projection layer, the plurality of hollow projections extending from the outer surface of the projection layer in a direction away from the support layer; and a land area, wherein the plurality of hollow projections are surrounded by the land area.

In various embodiments, the absorbent core has a body facing surface and projections extending away from the body facing surface of the absorbent core.

In various embodiments, the second component comprises at least one opening.

Figure 1:
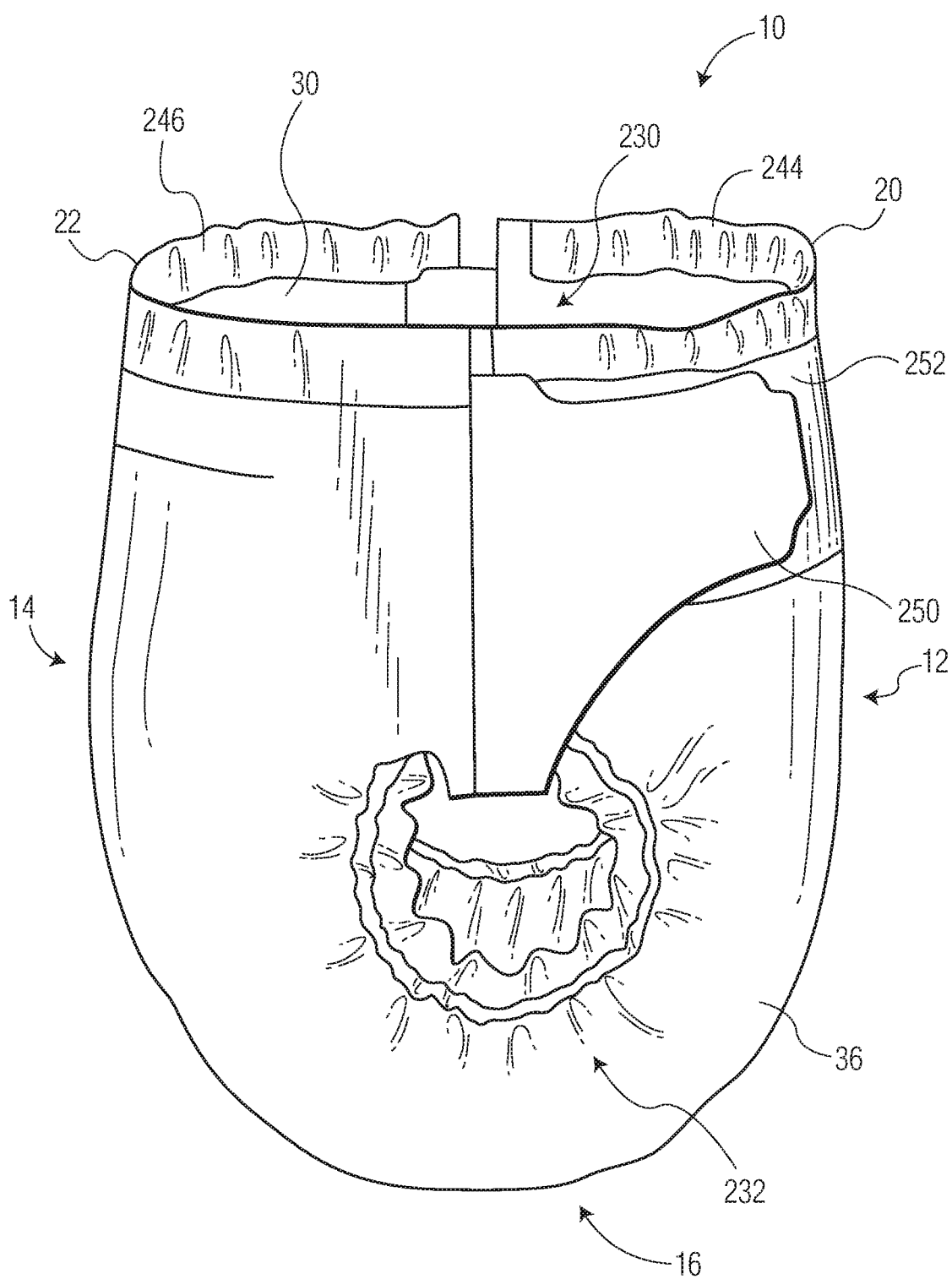
FIG. 1 is a side view of an exemplary embodiment of an absorbent article.

Repeat use of reference characters in the present specification and drawings is intended to represent the same or analogous features or elements of the disclosure.

DETAILED DESCRIPTION OF THE DISLOSURE

The present disclosure is directed towards an absorbent article which can have an improved conformity to the body of the wearer of the absorbent article providing for an improved intake and retention of body exudates such as fecal material. An absorbent article can have a longitudinal direction, a transverse direction, and a depth direction. The absorbent article can have an anterior region, a posterior region, and a central region. The absorbent article can have a topsheet layer, a liquid impermeable layer, and an absorbent core positioned between the topsheet layer and the liquid impermeable layer. The absorbent article can further include an exudate management layer in fluid communication with the topsheet layer. In various embodiments, the exudate management layer can be positioned on a body facing surface of the topsheet layer. In various embodiments, the exudate management layer can be positioned between the topsheet layer and the absorbent core. The exudate management layer has a first component which at least partially defines an opening for direct passage of body exudates into the absorbent core. The exudate management layer has a second component connected to the first component. The first component can provide the exudate management layer with a first height dimension and the second component can provide the exudate management layer with a second height dimension that is greater than the first height dimension.

Definitions:

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, and incontinence products, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. Nos. 4,100,324 to Anderson, et al., 4,818,464 to Lau, 5,284,703 to Everhart, et al., and 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. Nos. 5,108,820 to Kaneko, et al., 4,795,668 to Krueger, et al., 5,540,992 to Marcher, et al., 5,336,552 to Strack, et al., 5,425,987 to Shawver, and 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Absorbent Article:

The present disclosure is directed towards an absorbent article which can have an improved conformity to the body of the wearer of the absorbent article providing for an improved intake and retention of body exudates such as fecal material. An absorbent article can have a longitudinal direction, a transverse direction, and a depth direction. The absorbent article can have an anterior region, a posterior region, and a central region. The absorbent article can have a topsheet layer, a liquid impermeable layer, and an absorbent core positioned between the topsheet layer and the liquid impermeable layer. The absorbent article can further include an exudate management layer in fluid communication with the topsheet layer. In various embodiments, the exudate management layer can be positioned on a body facing surface of the topsheet layer. In various embodiments, the exudate management layer can be positioned between the topsheet layer and the absorbent core. The exudate management layer has a first component which at least partially defines an opening for direct passage of body exudates into the absorbent core. The exudate management layer has a second component connected to the first component. The first component can provide the exudate management layer with a first height dimension and the second component can provide the exudate management layer with a second height dimension that is greater than the first height dimension.

Figure 2:
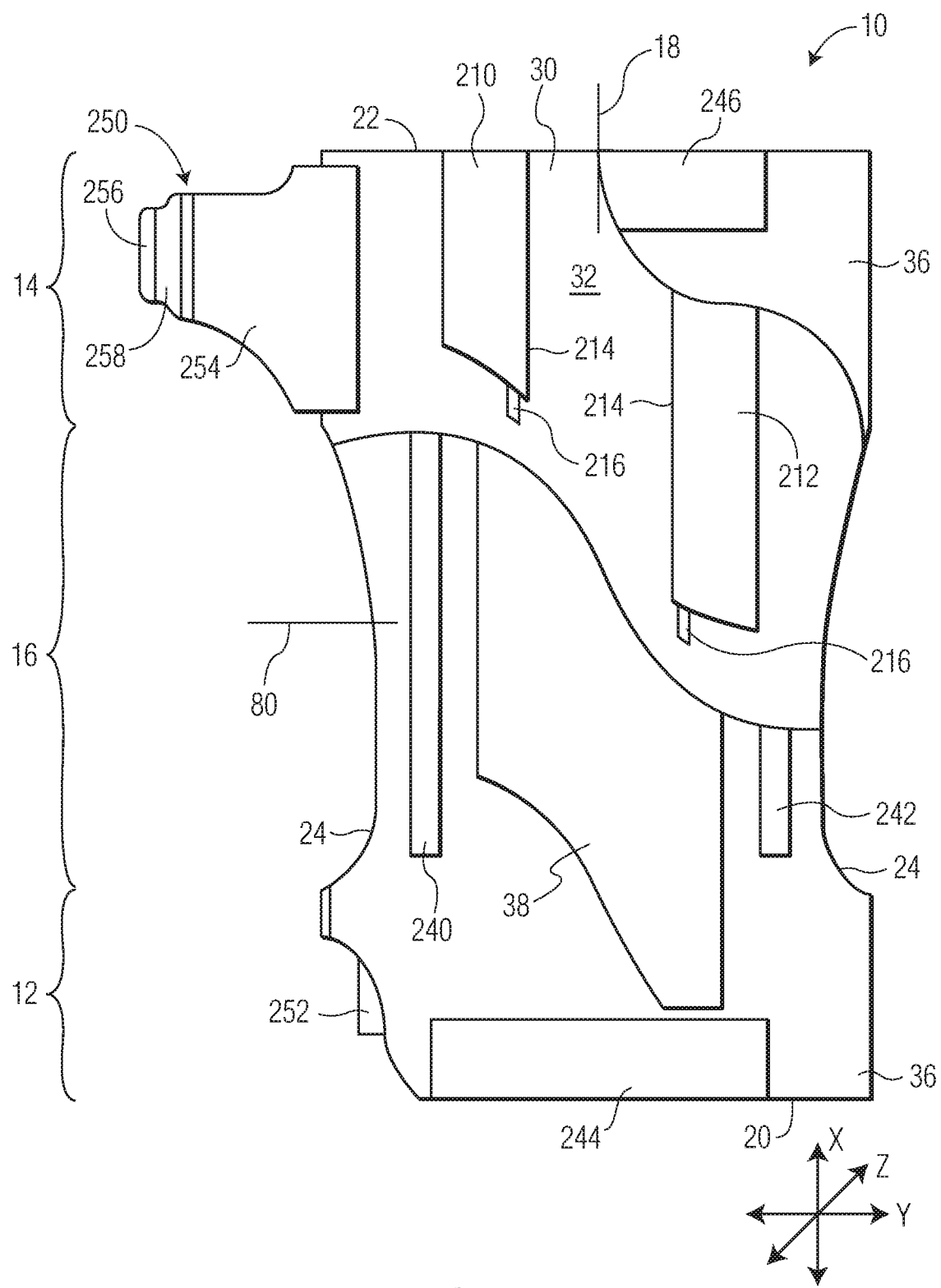
FIG. 2 is a top down view of the absorbent article of FIG. 1 with portions cut away for clarity.

Referring to FIGS. 1, 2, 3, 4A, 4B, 5, 6A, 6B, 7, 8A, 8B, 9A, and 9B, an absorbent article 10 of the present disclosure is exemplified in the form of a diaper. It is to be understood that the present disclosure is suitable for use with various other absorbent articles which are designed to be worn about the lower torso of a wearer, such as, but not limited to, training pants or adult incontinence pants, without departing from the scope of the present disclosure. FIG. 1 is a side view of an exemplary embodiment of the absorbent article 10 and FIG. 2 is a top down view of an exemplary embodiment of an absorbent article 10 with portions cut away for clarity. FIGS. 3, 4A, 4B, 5, 6A, 6B, 7, 8A, 8B, 9A, and 9B provide further illustrations of exemplary embodiments of an absorbent article 10 with an exudate management layer 40.

The absorbent article 10 can have a longitudinal direction (X), a transverse direction (Y), and a depth direction (Z). The absorbent article 10 can have an anterior region 12, a posterior region 14, and a central region 16 located between the anterior region 12 and the posterior region 14. The absorbent article 10 can have a first transverse direction end edge 20, a second transverse direction end edge 22 opposed to the first transverse direction end edge 20, and a pair of opposing longitudinal direction side edges 24 extending between and connecting the first and second transverse direction end edges, 20 and 22. The absorbent article 10 can have a wearer facing, liquid permeable topsheet layer 30 and a garment facing, liquid impermeable layer 36. An absorbent core 38 can be positioned between the topsheet layer 30 and the liquid impermeable layer 36. The absorbent article 10 can have an exudate management layer 40 in fluid communication with the topsheet layer 30. In various embodiments, the exudate management layer 40 can be positioned on a body facing surface 32 of the topsheet layer 30 such as, for example, illustrated in the exemplary embodiments illustrated in FIGS. 3, 4A, 4B, 5, 6A, and 6B. In various embodiments, the exudate management layer 40 can be positioned between the topsheet layer 30 and the absorbent core 38 such as, for example, illustrated in the exemplary embodiments illustrated in FIGS. 7, 8A, 8B, 9A, and 9B. The topsheet layer 30 and the liquid impermeable layer 36 can both extend beyond the outermost peripheral edges of the absorbent core 38 and can be peripherally bonded together, either entirely or partially, using known bonding techniques to form a sealed peripheral region. For example, the topsheet layer 30 and the liquid impermeable layer 36 can be bonded together by adhesive bonding, ultrasonic bonding, or any other suitable bonding technique known in the art.

In various embodiments in which the absorbent article 10 is a diaper, training pant, youth pant, swim pant, or an incontinence product such as an adult incontinence pant, the absorbent article 10 can be worn about the lower torso of the wearer and can have a waist opening 230 and leg openings 232.

The absorbent article 10 can have leg elastic members, 240 and 242, which can be bonded to the liquid impermeable layer 36 such as by, for example, an adhesive, generally adjacent the lateral outer edges of the liquid impermeable layer 36. Alternatively, the leg elastic members, 240 and 242, may be disposed between other layers of the absorbent article 10. A wide variety of elastic materials may be used for the leg elastic members, 240 and 242. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

In various embodiments, the absorbent article 10 can have waist elastic members, 244 and 246, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 244 and 246, may be omitted from the absorbent article 10 without departing from the scope of this disclosure.

In various embodiments, the absorbent article 10 can include a fastener system. The fastener system can include one or more back fasteners 250 and one or more front fasteners 252. Portions of the fastener system may be included in the anterior region 12, posterior region 14, or both. The fastener system can be configured to secure the absorbent article 10 about the waist of the wearer and maintain the absorbent article 10 in place during use. In an embodiment, the back fasteners 250 can include one or more materials bonded together to form a composite ear as is known in the art. For example, the composite fastener may be composed of a stretch component 254, a nonwoven carrier or hook base 256, and a fastening component 258.

Topsheet Layer:

The topsheet layer 30 defines a body facing surface 32 of the absorbent article 10 that may directly contact the body of the wearer and is liquid permeable to receive body exudates. The topsheet layer 30 is desirably provided for comfort and functions to direct body exudates away from the body of the wearer, through its own structure, and towards the absorbent core 38. The topsheet layer 30 desirably retains little to no liquid in its structure, so that it provides a relatively comfortable and non-irritating surface next to the skin of the wearer of the absorbent article 10.

The topsheet layer 30 can be a single layer of material, or alternatively, can be multiple layers that have been laminated together. The topsheet layer 30 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 30.

In various embodiments the topsheet layer 30 can be constructed from various nonwoven webs such as meltblown webs, spunbond webs, hydroentangled spunlace webs, or through air bonded carded webs. Examples of suitable topsheet layer 30 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 30 can be a bonded carded web made of polypropylene and polyethylene such as that obtainable from Sandler Corp., Germany. U.S. Pat. Nos. 4,801,494 to Datta, et al., and 4,908,026 to Sukiennik, et al., and WO 2009/062998 to Texol teach various other topsheet materials that may be used as the topsheet layer 30, each of which is hereby incorporated by reference thereto in its entirety. Additional topsheet layer 30 materials can include, but are not limited to, those described in U.S. Pat. Nos. 4,397,644 to Matthews, et al., 4,629,643 to Curro, et al., 5,188,625 to Van Iten, et al., 5,382,400 to Pike, et al., 5,533,991 to Kirby, et al., 6,410,823 to Daley, et al., and U.S. Publication No. 2012/0289917 to Abuto, et al., each of which is hereby incorporated by reference thereto in its entirety.

In various embodiments, the topsheet layer 30 may contain a plurality of apertures formed therethrough to permit body exudates to pass more readily into the absorbent core 38. The apertures may be randomly or uniformly arranged throughout the topsheet layer 30. The size, shape, diameter, and number of apertures may be varied to suit an absorbent article's 10 particular needs.

In various embodiments, the tosphheet layer 30 can have a basis weight ranging from about 5, 10, 15, 20, or 25 gsm to about 50, 100, 120, 125, or 150 gsm. For example, in an embodiment, a topsheet layer 30 can be constructed from a through air bonded carded web having a basis weight ranging from about 15 gsm to about 100 gsm. In another example, a topsheet layer 30 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 30 can be at least partially hydrophilic. In various embodiments, a portion of the topsheet layer 30 can be hydrophilic and a portion of the topsheet layer 30 can be hydrophobic. In various embodiments, the portions of the topsheet layer 30 which can be hydrophobic can be either an inherently hydrophobic material or can be a material treated with a hydrophobic coating.

In various embodiments, the topsheet layer 30 can be a multicomponent topsheet layer 30 such as by having two or more different nonwoven or film materials, with the different materials placed in separate locations in the transverse direction (Y) of the absorbent article 10. For example, the topsheet layer 30 can be a two layer or multicomponent material having a central portion positioned along and straddling a longitudinal centerline 18 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 30 are generally described in U.S. Pat. Nos. 5,961,505 to Coe, 5,415,640 to Kirby, and 6,117,523 to Sugahara, each of which is incorporated herein by reference thereto in its entirety.

In various embodiments, a central portion of a topsheet layer 30 can be positioned symmetrically about the absorbent article 10 longitudinal centerline 18. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 30. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 30. The selection of such topsheet layer 30 materials can vary based upon the overall desired attributes of the topsheet layer 30. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 30 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 30. The film layer may also serve as a barrier layer to prevent rewet of the topsheet layer 30 as well as to prevent the flow of fluid off the side edges of the absorbent article 10. In various embodiments, the side portions can be laminates such as a spunbond-meltblownmeltblown-spunbond layer ("SMMS") laminate, spunbond-film laminate, or alternatively, other nonwoven laminate combinations.

Figure 10:
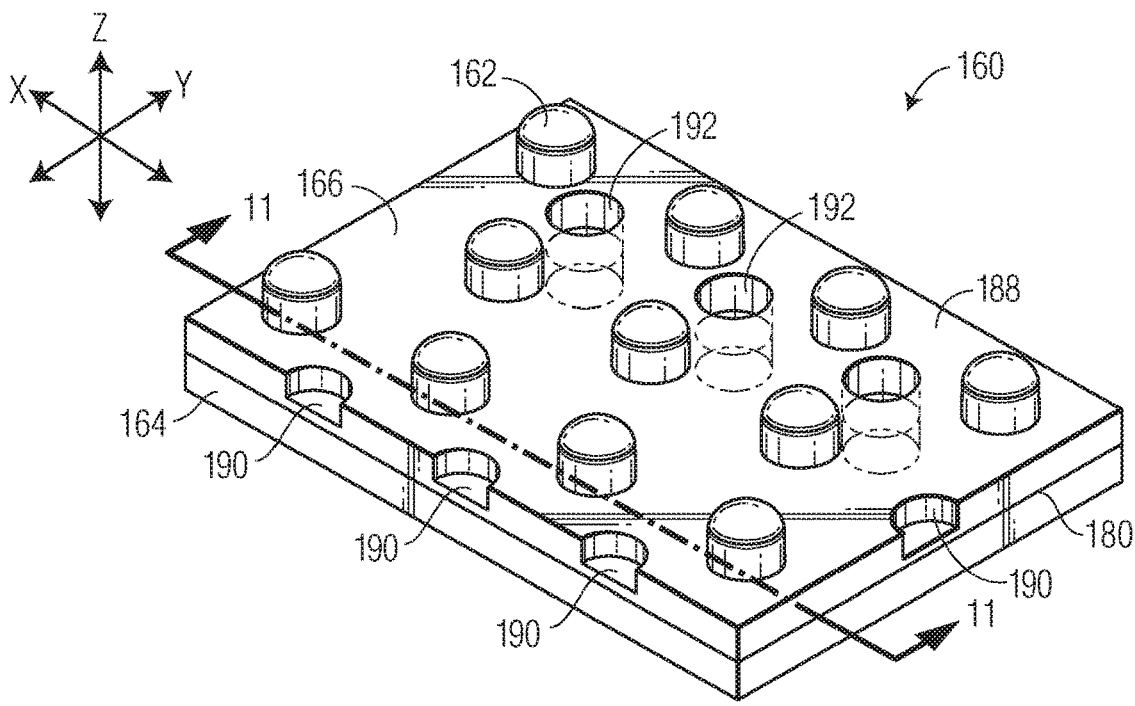
FIG. 10 is a perspective view of an exemplary embodiment of a topsheet layer.
Figure 11:
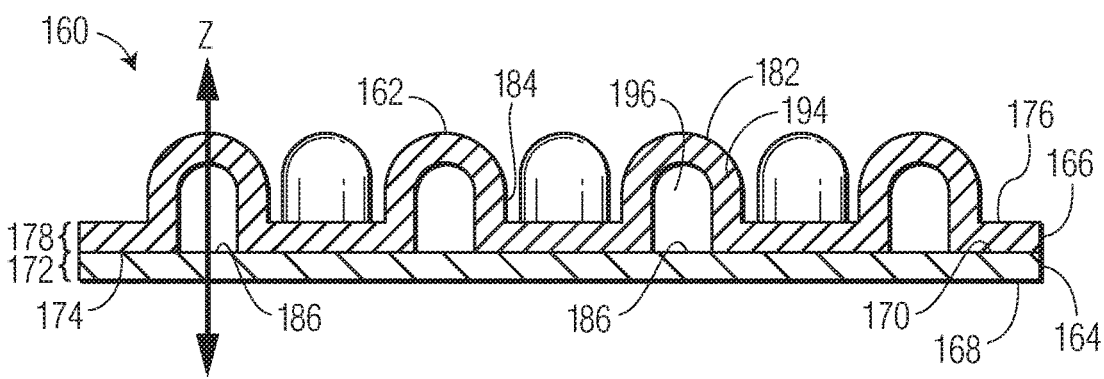
FIG. 11 is a cross-sectional view of the topsheet layer of FIG. 10 taken along line 11-11.
Figure 12:
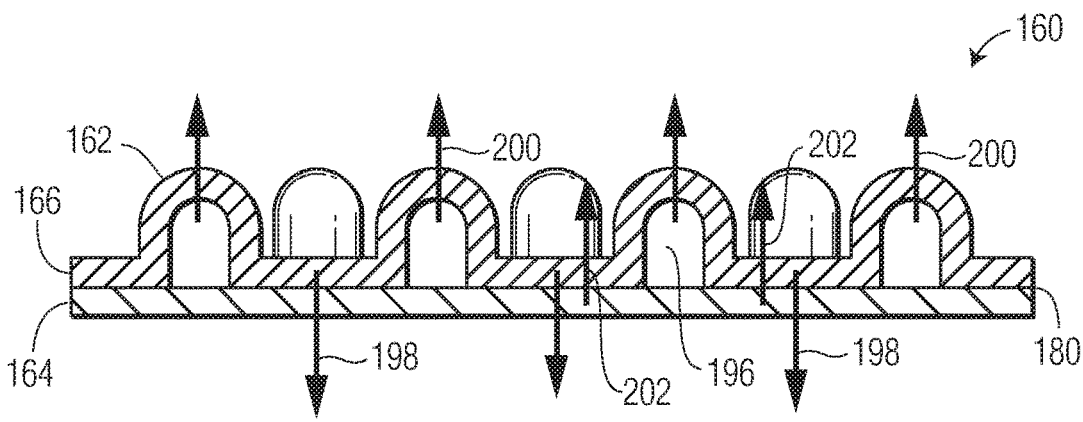
FIG. 12 is a cross-sectional view of the topsheet layer of FIG. 10 taken along line 11-11 showing possible directions of fiber movements within the topsheet layer due to a fluid entanglement process.

In various embodiments, the topsheet layer 30 can be a fluid entangled laminate web 160 with projections 162 extending outwardly and away from at least one intended body-facing surface of the laminate web 160 such as illustrated in FIGS. 10-12. In various embodiments, the projections 162 can be hollow. The laminate web 160 can have two layers such as a support layer 164 and a projection layer 166. The support layer 164 can have a first surface 168 and an opposed second surface 170 as well as a thickness 172. The projection layer 166 can have an inner surface 174 and an opposed outer surface 176 as well as a thickness 178. An interface 180 can be present between the support layer 164 and the projection layer 166. In various embodiments, fibers of the projection layer 166 can cross the interface 180 and be entangled with and engage the support layer 164 so as to form the laminate web 160. In various embodiments in which the support layer 164 is a fibrous nonwoven web, the fibers of the support layer 164 may cross the interface 180 and be entangled with the fibers of the projection layer 166.

In various embodiments, the projections 162 can be filled with fibers from the projection layer 166 and/or the support layer 164. In various embodiments, the projections 162 can be hollow. The projections 162 can have closed ends 182 which can be devoid of apertures. In various embodiments, however, it may be desirable to create one or more apertures in each of the projections 162. Such apertures can be formed in the closed ends 182 and/or side walls 184 of the projections 162. Such apertures are to be distinguished from interstitial fiber-to-fiber spacing which is the spacing from one individual fiber to the next individual fiber.

In various embodiments, the projections 162 can have a percentage of open area in which light can pass through the projections 162 unhindered by the material forming the projections 162, such as, for example, fibrous material. The percentage of open area present in the projections 162 encompasses all area of the projection 162 wherein light can pass through the projection 162 unhindered. Thus, for example, the percentage of open area of a projection 162 can encompass all open area of the projection 162 via apertures, interstitial fiber-to-fiber spacing, and any other spacing within the projection 162 where light can pass through unhindered. In various embodiments, the projections 162 can be formed without apertures and the open area can be due to the interstitial fiber-to-fiber spacing. In various embodiments, the projections 162 can have less than about 1, 0.9, 0.8, 0.7, 0.6, 0.5, 0.4, 0.3, 0.2, or 0.1% open area in a chosen area of the laminate web 160 as measured according to the Method to Determine Percent Open Area test method described herein.

In various embodiments, the shapes of the projections 162, when viewed from above, may be, for example, round, oval, square, rectangular, triangular, diamond-shaped, etc. Both the width and the height of the projections 162 can be varied as can be the spacing and pattern of the projections 162. In an embodiment, the projections 162 can have a height, measured according to the Method for Determining Height of Projections test method described herein, of greater than about 1 mm. In various embodiments, the projections 162 can have a height greater than about 1, 2, 3, 4, 5, 6, 7, 8, 9, or 10 mm. In various embodiments, the projections 162 can have a height from about 1, 2, 3, 4, or 5 mm to about 6, 7, 8, 9, or 10 mm.

The projections 162 of the laminate web 160 can be located on and emanate from the outer surface 176 of the projection layer 166. In various embodiments, the projections 162 can extend from the outer surface 176 of the projection layer 166 in a direction away from the support layer 164. In various embodiments in which the projections 162 can be hollow, they can have open ends 186 which can be located towards the inner surface 174 of the projection layer 166 and can be covered by the second surface 170 of the support layer 164 or the inner surface 174 of the projection layer 166 depending upon the amount of fiber that has been used from the projection layer 166 to form the projections 162. The projections 162 can be surrounded by land areas 188 which can be formed from the outer surface 176 of the projection layer 166 though the thickness of the land areas 188 can be comprised of both the projection layer 166 and the support layer 164. The land areas 188 can be relatively flat and planar or topographical variability may be built into the land areas 188. For example, in various embodiments, a land area 188 may have a plurality of three-dimensional shapes formed into it by forming the projection layer 166 on a three-dimensionally-shaped forming surface such as is disclosed in U.S. Pat. No. 4,741,941 to Engelbert, et al. and incorporated herein by reference in its entirety for all purposes. For example, in various embodiments, a land area 188 may be provided with depressions 190 which can extend all or part way into the projection layer 166 and/or support layer 164. In addition, a land area 188 may be subjected to embossing which can impart surface texture and other functional attributes to the land area 188. In various embodiments, a land area 188 and the laminate web 160 as a whole may be provided with apertures 192 which can extend through the laminate web 160 so as to further facilitate the movement of body exudate into and through the laminate web 160. Such apertures 192 are to be distinguished from interstitial fiber-to-fiber spacing, which is the spacing from one individual fiber to the next individual fiber.

In various embodiments, the land areas 188 can have a percentage of open area in which light can pass through the land areas 188 unhindered by the material forming the land areas 188, such as, for example, fibrous material. The percentage of open area present in the land areas 188 encompasses all area of the land areas 188 where light can pass through the land areas 188 unhindered. Thus, for example, the percentage of open area of a land area 188 can encompass all open area of the land areas 188 via apertures, interstitial fiber-to-fiber spacing, and any other spacing within the land areas 188 when light can pass through unhindered. In various embodiments, the land areas 188 can have greater than about 1% open area in a chosen area of laminate web 160, as measured according to the Method to Determine Percent Open Area test method described herein. In various embodiments, the land areas 188 can be formed without apertures and the open area can be due to the interstitial fiber-to-fiber spacing. In various embodiments, the land areas 188 can have greater than about 1, 2, 3, 4, 5, 6, 7, 8, 9, 10, 11, 12, 13, 14, 15, 16, 17, 18, 19, or 20% open area in a chosen area of the laminate web 160. In various embodiments, the land areas 188 can have about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20% open area in a chosen area of the laminate web 160. In various embodiments, the land areas 188 can have from about 1, 2, or 3% to about 4 or 5% open area in a chosen area of the laminate web 160. In various embodiments, the land areas 188 can have from about 5, 6, or 7% to about 8, 9, or 10% open area in a chosen area of the laminate web 160. In various embodiments, the land areas 188 can have from about 10, 11, 12, 13, 14, or 15% to about 16, 17, 18, 19, or 20% open area in a chosen area of the laminate web 160. In various embodiments, the land areas can have greater than about 20% open area in a chosen area of the laminate web 160.

The projections 162 of the laminate web 160 can be provided in any orientation as deemed suitable. In various embodiments, the projections 162 of the laminate web 160 can be provided randomly to the laminate web 160. In various embodiments, the projections 162 can be oriented linearly in the longitudinal direction (X) of the absorbent article 10. In various embodiments, the projections 162 can be oriented linearly in the transverse direction (Y) of the absorbent article 10. In various embodiments, the projections 162 can be oriented linearly in a direction which can be at an angle to the longitudinal direction (X) and/or the transverse direction (Y) of the absorbent article 10.

The land areas 188 of the laminate web 160 can be provided in any orientation as deemed suitable. In various embodiments, the land areas 188 can be oriented linearly in the longitudinal direction (X) of the absorbent article 10. In various embodiments, the land areas 188 can be oriented linearly in the transverse direction (Y) of the absorbent article 10. In various embodiments, the land areas 188 can be oriented linearly in a direction which can be at an angle to the longitudinal direction (X) and the transverse direction (Y) of the absorbent article 10.

In various embodiments, the projections 162 and/or the land areas 188 can be provided such that the projections 162 are located in the central region 16 of the absorbent article 10, are located towards the perimeter of the absorbent article 10, and combinations thereof. In various embodiments, the projections 162 can have varying heights in different areas of the absorbent article 10. In such embodiments, for example, the projections 162 can have a first height in an area of the absorbent article 10 and a different height in a different area of the absorbent article 10. In various embodiments, the projections 162 can have varying diameters in different areas of the absorbent article 10. In such embodiments, for example, the projections 162 can have a first diameter in an area of the absorbent article 10 and can have a different diameter in another area of the absorbent article 10. In various embodiments, the concentration of projections 162 can vary in the absorbent article 10. In such embodiments, an area of the absorbent article 10 can have a higher concentration of projections 162 than the concentration of projections 162 in a second area of the absorbent article 10.

While it is possible to vary the density and fiber content of the projections 162, in various embodiments, the projections 162 can be "hollow." When the projections 162 are hollow, they can have a shell 194 formed from the fibers of the projection layer 166. The shell 194 can define an interior space 196 which can have a lower density of fibers as compared to the shell 194 of the projections 162. By "density" it is meant the fiber count or content per chosen unit of volume within a portion of the interior space 196 or the shell 194 of the projection 162. The density of the shell 194 may vary within a particular or individual projection 162 and it also may vary as between different projections 162. In addition, the size of the hollow interior space 196 as well as its density may vary within a particular or individual projection 162 and it also may vary as between different projections 162. If there is at least some portion of an interior space 196 of a projection 162 that has a lower fiber density than at least some portion of the shell 194 of the same projection 162, then the projection 162 is regarded as being "hollow". In this regard, in some situations, there may not be a well-defined demarcation between the shell 194 and the interior space 196 of the projection 162 but, if with sufficient magnification of a cross-section of one of the projections 162, it can be seen that at least some portion of the interior space 196 of the projection 162 has a lower density than some portion of the shell 194 of the same projection 162, then the projection 162 is regarded as being "hollow", If at least a portion of the projections 162 of a laminate web 160 are hollow, the projection layer 166 and the laminate web 160 are regarded as being "hollow" or as having "hollow projections". In various embodiments, the portion of the projections 162 which are hollow can be greater than or equal to about 50 percent of the projections 162 in a chosen area of the laminate web 160. In various embodiments, greater than or equal to about 70 percent of the projections 162 in a chosen area of the laminate web 160 can be hollow. In various embodiments, greater than or equal to about 90 percent of the projections 162 in a chosen area of the laminate web 160 can be hollow.

The laminate web 160 can be the result of the movement of the fibers in the projection layer 166 in one and sometimes two or more directions. As previously noted, the laminate web 160 can be a fluid entangled laminate web. Referring to FIG. 12, if the forming surface upon which the projection layer 166 is placed is solid except for the forming holes used to form the projections 162, then the force of the fluid entangling streams hitting and rebounding off the solid surface land areas corresponding to the land areas 188 of the projection layer 166 can cause a migration of fibers adjacent the inner surface 174 of the projection layer 166 into the support layer 164 adjacent its second surface 170. This migration of fibers in the first direction can be represented by the arrows 198 shown in FIG. 12. In order to form the projections 162 extending outwardly from the outer surface 176 of the projection layer 166, there must be a migration of fibers in a second direction as shown by the arrows 200. It is this migration in the second direction which causes fibers from the projection layer 166 to move out and away from the outer surface 176 to form the projections 162. In various embodiments in which the support layer 164 can be a fibrous nonwoven web, depending on the degree of web integrity and the strength and dwell time of the fluid jets during the entanglement process, there may also be movement of support layer 164 fibers into the projection layer 166 as shown by arrows 202 in FIG. 12. The net result of these fiber movements can be the creation of a laminate web 160 with good overall integrity and lamination of the layers (164 and 166) at their interface 180 thereby allowing further processing and handling of the laminate web 160. As a result of the fluid entanglement process to create the laminate web 160, it is generally not desirable that the fluid pressure used to form the projections 162 be of sufficient force so as to force fibers from the support layer 164 to be exposed on the outer surface 176 of the projection layer 166.

The support layer 164 can support the projection layer 166 and can be made from a number of structures provided the support layer 164 can be capable of supporting the projection layer 166. The primary functions of the support layer 164 can be to protect the projection layer 166 during the formation of the projections 162, to be able to bond to or be entangled with the projection layer 166 and to aid in further processing of the projection layer 166 and the resultant laminate web 160. Suitable materials for the support layer 164 can include, but are not limited to, nonwoven fabrics or webs, scrim materials, netting materials, paper/cellulose/wood pulp-based products which can be considered a subset of nonwoven fabrics or webs as well as foam materials, films and combinations of the foregoing provided the material or materials chosen are capable of withstanding a process of manufacture such as a fluid-entangling process. In an embodiment, the support layer 164 can be a fibrous nonwoven web made from a plurality of randomly deposited fibers which may be staple length fibers such as are used, for example, in carded webs, air laid webs, etc. or they may be more continuous fibers such as are found in, for example, meltblown or spunbond webs. Due to the functions the support layer 164 must perform, the support layer 164 can have a higher degree of integrity than the projection layer 166. In this regard, the support layer 164 can remain substantially intact when it is subjected to a fluid-entangling process. The degree of integrity of the support layer 164 can be such that the material forming the support layer 164 can resist being driven down into and filling the projections 162 of the projection layer 166. As a result, in an embodiment in which the support layer 164 is a fibrous nonwoven web, it should have a higher degree of fiber-to-fiber bonding and/or fiber entanglement than the fibers in the projection layer 166. While it can be desirable to have fibers from the support layer 164 entangle with the fibers of the projection layer 166 adjacent the interface 180 between the two layers, it is generally desired that the fibers of this support layer 164 not be integrated or entangled into the projection layer 166 to such a degree that large portions of these fibers find their way inside the projections 162.

In order to resist the higher degree of fiber movement, as mentioned above, in an embodiment, the support layer 164 can have a higher degree of integrity than the projection layer 166. This higher degree of integrity can be brought about in a number of ways. One can be fiber-to-fiber bonding which can be achieved through thermal or ultrasonic bonding of the fibers to one another with or without the use of pressure as in through-air bonding, point bonding, powder bonding, chemical bonding, adhesive bonding, embossing, calender bonding, etc. In addition, other materials may be added to the fibrous mix such as adhesives and/or bicomponent fibers. Pre-entanglement of a fibrous nonwoven support layer 164 may also be used such as, for example, by subjecting the web to hydroentangling, needlepunching, etc., prior to this support layer 164 being joined to a projection layer 166. Combinations of the foregoing are also possible. Still other materials such as foams, scrims and nettings may have enough initial integrity so as to not need further processing. The level of integrity can in many cases be visually observed due to, for example, the observation with the unaided eye of such techniques as point bonding which is commonly used with fibrous nonwoven webs such as spunbond webs and staple fiber-containing webs. Further magnification of the support layer 164 may also reveal the use of fluid-entangling or the use of thermal and/or adhesive bonding to join the fibers together. Depending on whether samples of the individual layers (164 and 166) are available, tensile testing in either or both of the machine and cross-machine directions may be undertaken to compare the integrity of the support layer 164 to the projection layer 166. See for example ASTM test D5035-11 which is incorporated herein its entirety for all purposes.

The type, basis weight, tensile strength and other properties of the support layer 164 can be chosen and varied depending upon the particular end use of the resultant laminate web 160. When the laminate web 160 is to be used as part of a personal care absorbent article, it can be generally desirable that the support layer 164 be a layer that is fluid pervious, has good wet and dry strength, is able to absorb fluids such as body exudates, possibly retain the fluids for a certain period of time and then release the fluids to one or more subjacent layers. In this regard, fibrous nonwovens such as spunbond webs, meltblown webs and carded webs such as airlaid webs, bonded carded webs and coform materials are well-suited as support layers 164. Foam materials and scrim materials are also well-suited. In addition, the support layer 164 may be a multi-layered material due to the use of several layers or the use of multi-bank formation processes as are commonly used in making spunbond webs and meltblown webs as well as layered combinations of meltblown and spunbond webs. In the formation of such support layers 164, both natural and synthetic materials may be used alone or in combination to fabricate the materials. In various embodiments, the support layer 164 can have a basis weight ranging from about 5 to about 40 or 50 gsm.

The type, basis weight and porosity of the support layer 164 can affect the process conditions necessary to form the projections 162 in the projection layer 166. Heavier basis weight materials can increase the entangling force of the entangling fluid streams needed to form the projections 162 in the projection layer 166. However, heavier basis weight support layers 164 can also provide improved support for the projection layer 166 as the projection layer 166 by itself can be too stretchy to maintain the shape of the projections 162 post the formation process. The projection layer 164 by itself can unduly elongate in the machine direction due to the mechanical forces exerted on it by subsequent winding and converting processes and consequently diminish and distort the projections. Also, without the support layer 164, the projections 162 in the projection layer 166 tend to collapse due to the winding pressures and compressive weights the projection layer 166 experiences in the winding process and subsequent conversion and do not recover to the extent they do when a support layer 164 is present.

The support layer 164 may be subjected to further treatment and/or additives to alter or enhance its properties. For example, surfactants and other chemicals may be added both internally and externally to the components forming all or a portion of the support layer 164 to alter or enhance its properties. Compounds commonly referred to as hydrogels or superabsorbents which absorb many times their weight in liquids may be added to the support layer 164 in both particulate and fiber form.

The projection layer 166 can be made from a plurality of randomly deposited fibers which may be staple length fibers such as are used, for example, in carded webs, airlaid webs, coform webs, etc., or they may be more continuous fibers such as are found in, for example, meltblown or spunbond webs. The fibers in the projection layer 166 can have less fiber-to-fiber bonding and/or fiber entanglement and thus less integrity as compared to the integrity of the support layer 164, especially in embodiments when the support layer 164 is a fibrous nonwoven web. In an embodiment, the fibers in the projection layer 166 may have no initial fiber-to-fiber bonding for purposes of allowing the formation of the projections 162. Alternatively, when both the support layer 164 and the projection layer 166 can both be fibrous nonwoven webs, the projection layer 166 can have less integrity than the support layer 164 due to the projection layer 166 having, for example, less fiber-to-fiber bonding, less adhesive or less pre-entanglement of the fibers forming the projection layer 166.

The projection layer 166 can have a sufficient amount of fiber movement capability to allow a fluid entangling process to be able to move a first plurality of the plurality of fibers of the projection layer 166 out of the X-Y plane of the projection layer 166 and into the perpendicular or Z-direction of the projection layer 166 so as to be able to form the projections 162. As noted herein, in various embodiments, the projections 162 can be hollow. In an embodiment, a second plurality of the plurality of fibers in the projection layer 166 can become entangled with the support layer 164. If more continuous fiber structures are being used such as meltblown or spunbond webs, in an embodiment, there may be little or no pre-bonding of the projection layer 166 prior to the fluid entanglement process. Longer fibers such as are generated in meltblowing and spunbonding processes (which are often referred to as continuous fibers to differentiate them from staple length fibers) will typically require more force to displace the fibers in the Z-direction than will shorter, staple length fibers that typically have fiber lengths less than about 100 mm and more typically fibers lengths in the 10 to 60 mm range. Conversely, staple fiber webs such as carded webs and airlaid webs can have some degree of pre-bonding or entanglement of the fibers due to their shorter length. Such shorter fibers require less fluid force from the fluid entangling streams to move them in the Z-direction to form the projections 162. As a result, a balance must be met between fiber length, degree of pre-fiber bonding, fluid force, web speed and dwell time so as to be able to create the projections 162 without, unless desired, forming apertures in the land areas 188 or the projections 162 or forcing too much material into the interior space 196 of the projections 162 thereby making the projections 162 too rigid for some end-use applications.

In various embodiments, the projection layer 166 can have a basis weight ranging from about 10 gsm to about 60 gsm. Spunbond webs can typically have basis weights of between about 15 and about 50 gsm when being used as the projection layer 166. Fiber diameters can range between about 5 and about 20 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. Hollow fibers may also be used. The fibers may be formed from any polymer formulations typically used to form spunbond webs. Examples of such polymers include, but are not limited to, polypropylene ("PP"), polyester ("PET"), polyamide ("PA"), polyethylene ("PE") and polylactic acid ("PLA"). The spunbond webs may be subjected to post-formation bonding and entangling techniques if necessary to improve the processability of the web prior to its being subjected to the projection forming process.

Meltblown webs can typically have basis weights of between about 20 and about 50 gsm when being used as the projection layer 166. Fiber diameters can range between about 0.5 and about 5 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. The fibers may be formed from any polymer formulations typically used to form spunbond webs. Examples of such polymers include, but are not limited to, PP, PET, PA, PE and PLA.

Carded and airlaid webs can use staple fibers that can typically range in length between about 10 and about 100 millimeters. Fiber denier can range between about 0.5 and about 6 denier depending upon the particular end use. Basis weights can range between about 20 and about 60 gsm. The staple fibers may be made from a wide variety of polymers including, but not limited to, PP, PET, PA, PE, PLA, cotton, rayon, flax, wool, hemp and regenerated cellulose such as, for example, Viscose. Blends of fibers may be utilized too, such as blends of bicomponent fibers and single component fibers as well as blends of solid fibers and hollow fibers. If bonding is desired, it may be accomplished in a number of ways including, for example, through-air bonding, calender bonding, point bonding, chemical bonding and adhesive bonding such as powder bonding. If needed, to further enhance the integrity and processability of a projection layer 166 prior to the projection forming process, the projection layer 166 may be subjected to pre-entanglement processes to increase fiber entanglement within the projection layer 166 prior to the formation of the projections 162. Hydroentangling can be advantageous in this regard.

Examples of a laminate web 160 and process for manufacturing a laminate web 160 can be found in U.S. Pat. No. 9,474,660 to Kirby et al. which is hereby incorporated by reference in its entirety.

Absorbent Core:

An absorbent core 38 can be positioned between the topsheet layer 30 and the liquid impermeable layer 36 of the absorbent article 10. The absorbent core 38 can generally be any single layer structure or combination of layer components, which can demonstrate some level of compressibility, conformability, be non-irritating to the wearer's skin, and capable of absorbing and retaining liquids and other body exudates. In various embodiments, the absorbent core 38 can be formed from a variety of different materials and can contain any number of desired layers. For example, the absorbent core 38 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 38 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 38 in any amount as desired.

Regardless of the combination of absorbent materials used in the absorbent core 38, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 38 can vary as desired and can comprise any one of various shapes including, but not limited to, triangular, rectangular, dog-bone, elliptical, trapezoidal, T-shape, I-shape, and hourglass shapes. In various embodiments, the absorbent core 38 can have a shape that generally corresponds with the overall shape of the absorbent article 10. The dimensions of the absorbent core 38 can be substantially similar to those of the absorbent article 10, however, it will be appreciated that the dimensions of the absorbent core 38 while similar, will often be less than those of the overall absorbent article 10, in order to be adequately contained therein. The size and the absorbent capacity of the absorbent core 38 should be compatible with the size of the intended wearer and the liquid loading imparted by the intended use of the absorbent article 10. Additionally, the size and the absorbent capacity of the absorbent core 38 can be varied to accommodate wearers ranging from infants to adults.

The absorbent core 38 can have a length ranging from about 120, 125, 130, 140, 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, 520, 530, 540, 550, 600, 610, 620, or 630 mm. The absorbent core 38 may have a width in the central region 16 ranging from about 30, 40, 50, 55, 60, 65, or 70 mm to about 75, 80, 85, 90, 95, 100, 105, 110, 115, 120, 125, 130, 140, 150, 160, 170 or 180 mm. The width of the absorbent core 38 located within the anterior region 12 and/or posterior region 14 of the absorbent article 10 may range from about 50, 55, 60, 65, 70, 75, 80, 85, 90, or 95 mm to about 100, 105, 110, 115, 120, 125 or 130 mm. As noted herein, the absorbent core 38 can have a length and width that can be less than or equal to the length and width of the absorbent article 10.

In an embodiment, the absorbent article 10 can be a diaper having the following ranges of lengths and widths of an absorbent core 38 having an hourglass shape: the length of the absorbent core 38 may range from about 170, 180, 190, 200, 210, 220, 225, 240 or 250 mm to about 260, 280, 300, 310, 320, 330, 340, 350, 355, 360, 380, 385, or 390 mm; the width of the absorbent core 38 in the central region 16 may range from about 40, 50, 55, or 60 mm to about 65, 70, 75, or 80 mm; the width of the absorbent core 38 in the anterior region 12 and/or the posterior region 14 may range from about 80, 85, 90, or 95 mm to about 100, 105, or 110 mm.

In an embodiment, the absorbent article 10 may be a training pant or youth pant having the following ranges of lengths and widths of an absorbent core 38 having an hourglass shape: the length of the absorbent core 38 may range from about 400, 410, 420, 440 or 450 mm to about 460, 480, 500, 510 or 520 mm; the width of the absorbent core 38 in the central region 16 may range from about 50, 55, or 60 mm to about 65, 70, 75, or 80 mm; the width of the absorbent core 38 in the anterior region 12 and/or the posterior region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent core 38 having a rectangular shape: the length of the absorbent core 38 may range from about 400, 410 or 415 to about 425 or 450 mm; the width of the absorbent core 38 in the central region 16 may range from about 90, or 95 mm to about 100, 105, or 110 mm. It should be noted that the absorbent core 38 of an adult incontinence garment may or may not extend into either or both the anterior region 12 or the posterior region 14 of the absorbent article 10.

In an embodiment, the absorbent article 10 can be a feminine hygiene product having the following ranges of lengths and widths of an absorbent body 40 having an hourglass shape: the length of the absorbent core 38 may range from about 150, 160, 170, or 180 mm to about 190, 200, 210, 220, 230, 240, 250, 260, 270, 280, 290, 300, 310 or 320 mm; the width of the absorbent core 38 in the central region 16 may range from about 30, 40, or 50 mm to about 60, 70, 80, 90 or 100 mm.

By way of example, suitable materials and/or structures for the absorbent core 38 can include, but are not limited to, those described in U.S. Pat. Nos. 4,610,678 to Weisman, et al., 6,060,636 to Yahiaoui, et al., 6,610,903 to Latimer, et al., 7,358,282 to Krueger, et al., and U.S. Publication No. 2010/0174260 to Di Luccio, et al. each of which is hereby incorporated by reference thereto in its entirety.

In various embodiments, an absorbent core 38 can be a single layer structure and can include, for example, a matrix of cellulosic fluff and superabsorbent material. In various embodiments, an absorbent core 38 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 38 may be constructed of an airlaid material and the garment facing layer of the absorbent core 38 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Liquid Impermeable Layer:

The liquid impermeable layer 36 is generally liquid impermeable and is the portion of the absorbent article 10 which faces the garments of the wearer. The liquid impermeable layer 36 can permit the passage of air or vapor out of the absorbent article 10 while still blocking the passage of liquids. Any liquid impermeable material may generally be utilized to form the liquid impermeable layer 36. The liquid impermable layer 36 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the liquid impermeable layer 36 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a liquid impermeable layer 36 can be a polyethylene film such as that obtainable from Pliant Corp., Schaumburg, Ill., USA. Another example can include calcium carbonate-filled polypropylene film. In still another embodiment, the liquid impermeable layer 36 can be a hydrophobic nonwoven material with water barrier properties such as a nonwoven laminate, an example of which can be a spunbond, meltblown, meltblown, spunbons, four-layered laminate.

In various embodiments, the liquid impermeable layer 36 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent article 10 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, Ind., U.S.A.

The liquid impermeable layer 36 can, therefore, be of a single or multiple layer construction, such as of multiple film layers or laminates of film and nonwoven fibrous layers. Suitable liquid impermeable layers 36 can be constructed from materials such as those described in U.S. Pat. Nos. 4,578,069 to Whitehead, et al., 4,376,799 to Tusim, et al., 5,695,849 to Shawver, et al., 6,075,179 to McCormack, et al., and 6,376,095 to Cheung, et al., each of which are hereby incorporated by reference thereto in its entirety.

Exudate Management Layer:

In various embodiments, the absorbent article 10 can have an exudate management layer 40 in fluid communication with the topsheet layer 30. In various embodiments, such as, for example, illustrated in FIGS. 3, 4A, 4B, 5, 6A, and 6B, the exudate management layer 40 can be positioned on the body facing surface 32 of the topsheet layer 30. In various embodiments, such as, for example, illustrated in FIGS. 7, 8A, 8B, 9A, and 9B, the exudate management layer 40 can be positioned between the topsheet layer 30 and the absorbent core 38.

In various embodiments, the exudate management layer 40 can be made of a material that can be capable of transferring, in the depth direction (Z), body exudates that are delivered to the topsheet layer 30. Any of a variety of materials can be utilized as the exudate management layer 40.

In various embodiments, the material can be synthetic, cellulosic, or a combination of synthetic and cellulosic materials. In various embodiments, the exudate management layer 40 can be constructed from woven or nonwoven materials. For example, the exudate management layer 40 can be constructed as an airlaid or a TABCW material. For example, airlaid cellulosic tissues may be suitable for use in the exudate management layer 40. The airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity.

In various embodiments, a foam material can be utilized to form the exudate management layer 40. In various embodiments, the foam material can be an open-cell or porous foam. The physical properties of the foam material as well as its wettability and fluid management properties can be tailored to meet the specific characteristics desired for the usage of a foam material in the absorbent article 10. In various embodiments, the foam material can be moisture stable and not degrade or collapse and lose its structure and fluid management properties when exposed to body exudate. In various embodiments, the foam material can be an open-cell foam, a closed cell foam, or a partially open-cell foam that is either a thermoplastic or thermoset material. A foam material can be manufactured by extrusion or casting and coating processes including frothed foam, aerated foam, and emulsion foam methods. Such foams can be manufactured from different polymer chemistries to achieve the desired softness, flexibility, and resilience of the foam material when utilized in an absorbent article 10. In various embodiments, the foam material can be based on organic or inorganic chemistries and can also be based upon a foam material obtained from natural sources. In various embodiments, the foam material can have a polymer chemistry which can be a polyurethane foam, polyolefin foam, poly (styrene-butadiene) foam, poly(ethylene-vinyl acetate) foam, or a silicone based foam. Other polymer chemistries known to one of ordinary skill in the art could be used along with additives such as plasticizers, opacifiers, colorants, antioxidants, and stabilizers to obtain the desired foam properties. In various embodiments, the viscoelastic properties could be modified to obtain a desired response to applied load from the foam material including properties similar to that commonly referred to as polyurethane memory foam materials. In various embodiments, the Poisson's ratio of the foam material could be modified to obtain the desired response from the foam material to applied stress and foam materials with auxetic properties could be considered if desired.

In various embodiments in which a foam material is utilized for the exudate management layer, the foam material can have material properties to enable cutting of the foam material such as, for example, with a mechanical die, such as foam materials which are referred to as clickable foams in the polyurethane foam industry. In various embodiments, the foam material can also be selected to enable other methods of cutting the foam material including, but not limited to, laser die cutting and water jet cutting. In various embodiments, the foam material can be tailored to enable perforating the foam material utilizing mechanical dies and cutting or hole-punching devices and can also be capable of achieving the perforation utilizing ultrasonic processes.

A porous foam material can have pores which can vary in size and/or distribution. In various embodiments, a pore size of a foam material can be from about 10 microns to about 350 microns. In various embodiments, the foam material can have a multimodal pore size distribution in order to handle a variety of components within the body exudates. In various embodiments, a multimodal pore size distribution can be achieved within the same monolithic foam structure or could be achieved by using layers of foam material with a narrow pore size distribution which when combined into a single foam material would allow a multimodal pore size distribution to be achieved for the combination of layers.

In various embodiments, the foam material can be a polyester polyurethane foam material. In various embodiments, the average cell size of the foam material can be from about 100, 150, or 200 microns to about 250, 300, or 350 microns. The number of open cells in the foam material can provide the foam material with measurement of the foam material's porosity. The porosity of the foam material is measured in pores per linear inch (ppi) and refers to the number of pores in one linear inch of a two-dimensional planar foam material surface and is described by the Polyurethane Foam Association. The pores per linear inch is measured by counting the pores visually under a microscope using a grid. The smaller the ppi value of the foam material the larger the pore size, and vice versa. In various embodiments, the foam material can have a porosity from about 20 or 40 ppi to about 55, 65, or 90 ppi. In various embodiments in which an open-cell foam material is utilized, the foam material can be substantially open-cell or of a completely reticulated structure. The reticulation of the foam material can be achieved by several methods known to one skilled in the art include foam made by in-situ reticulation processes during foam formation. The reticulated foam material can also be made by treating a substantially open-cell foam material to a high pressure fluid stream to remove the cell walls of the foam material. In general, foam materials are capable of stretching, however, in various embodiments the foam material can have a reduced elongation capacity. In various embodiments, the foam material can have a low elongation, such as, for example, less than a 200% elongation at break. In various embodiments, the foam material has an elongation at break from about 80 or 100% to about 150 or 200%. In various embodiments, the basis weight of the foam material can be from about 45 gsm to about 50 or 55 gsm. In various embodiments, the density of the foam material can be from about 0.01, 0.02 or 0.03 g/cc to about 0.05 or 0.08 g/cc. The foam material can also have a compression modulus that allows it to be soft and flexible when used in an absorbent article. In various embodiments, the foam material can have a compression force deflection at 25% deflection from about 0.5 or 0.6 psi to about 0.8 or 1.0 psi.

The foam material can be either hydrophilic or hydrophobic dependent upon the desired properties of the foam material in the absorbent article 10. In various embodiments the foam material can be a hydrophilic foam material. In various embodiments, the foam material can be hydrophobic and can be treated with a surfactant to create a hydrophilic foam material. In various embodiments, for example, the material utilized to form the exudate management layer 40 can be a hydrophobic, open-cell, polyurethane foam treated with from about 0.3% or 0.8% to about 1.6, 2.0, or 3.0% of a surfactant. In various embodiments, the surfactant utilized to treat the foam material can be a nonionic surfactant such as a nonionic surfactant comprising at least an ethoxylated linear oleochemical alcohol such as an alkylphenol ethoxylate, such as LUTENSOL® A65N, commercially available from BASF, or an ethoxylated acetylenic diol such as SURFYNOL® 465, commercially available from Air Products, Allentown, Pa. In various embodiments, the hydrophilicity of the foam material, as a result of the surfactant treatment, can be uniform in the longitudinal direction (X) and the transverse direction (Y) of the foam material. In various embodiments, the hydrophilicity of the foam material, as a result of the surfactant treatment, can vary in the longitudinal direction (X), in the transverse direction (Y), or in both of the longitudinal direction (X) and the transverse direction (Y). In various embodiments, the polymer utilized to formulate the foam material can be selected to have the desired hydrophilic properties. In various embodiments, this can be achieved by using an inherently hydrophilic polymer that is wettable by aqueous fluids or by including additives in the polymer during formation of the foam material. These additives can make the foam material wettable to aqueous fluids even if the base polymer of the foam material is hydrophobic. A non-limiting example of such an approach can be to include polyethylene glycol as an additive with a hydrophobic polymer.

Figure 13:
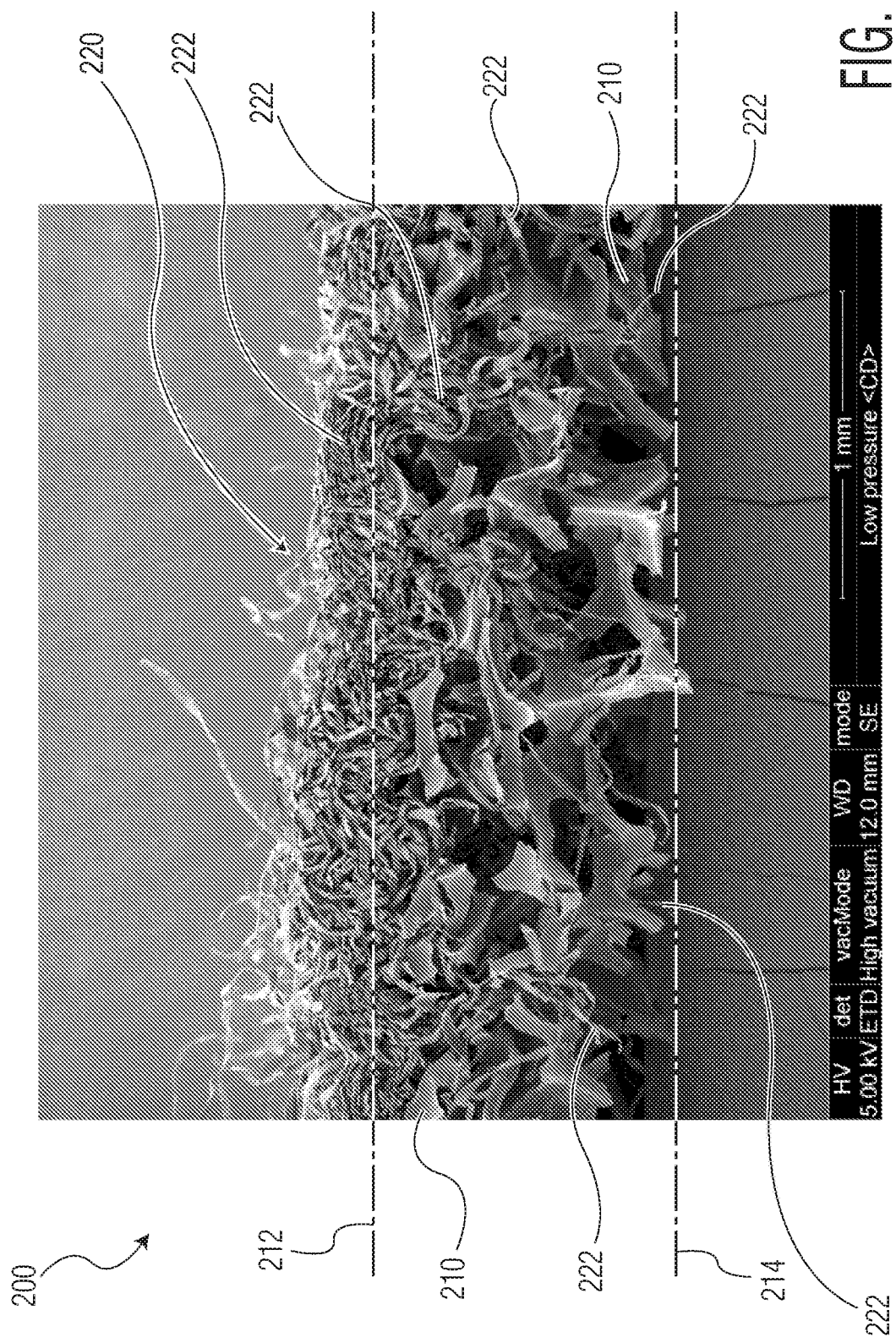
FIG. 13 is a photomicrograph of a cross-sectional view of a portion of a foam and fiber composite.
Figure 14:
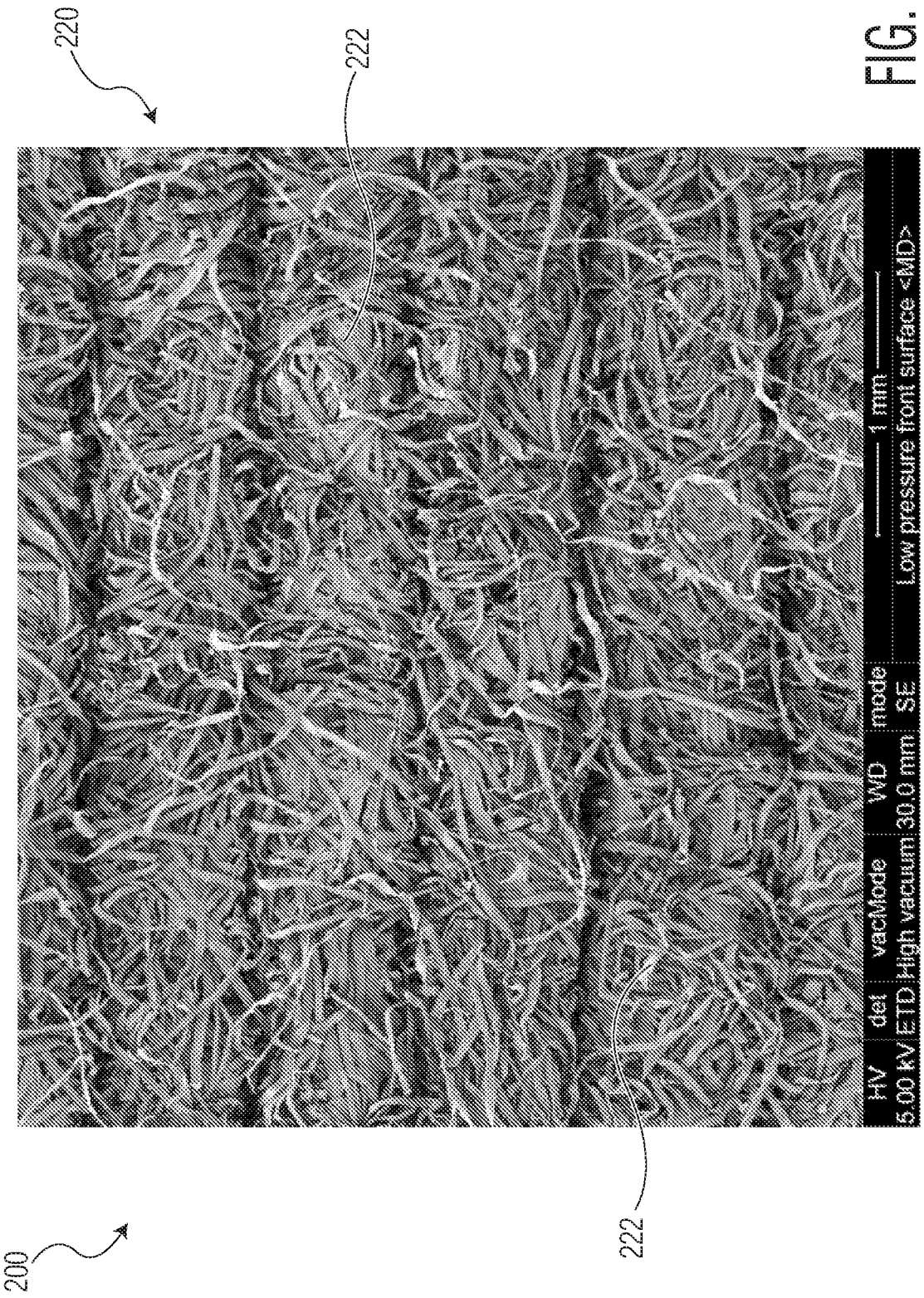
FIG. 14 is a photomicrograph of a planar view of the foam and fiber composite of FIG. 13 such that the fibrous material is visible to the viewer.
Figure 15:
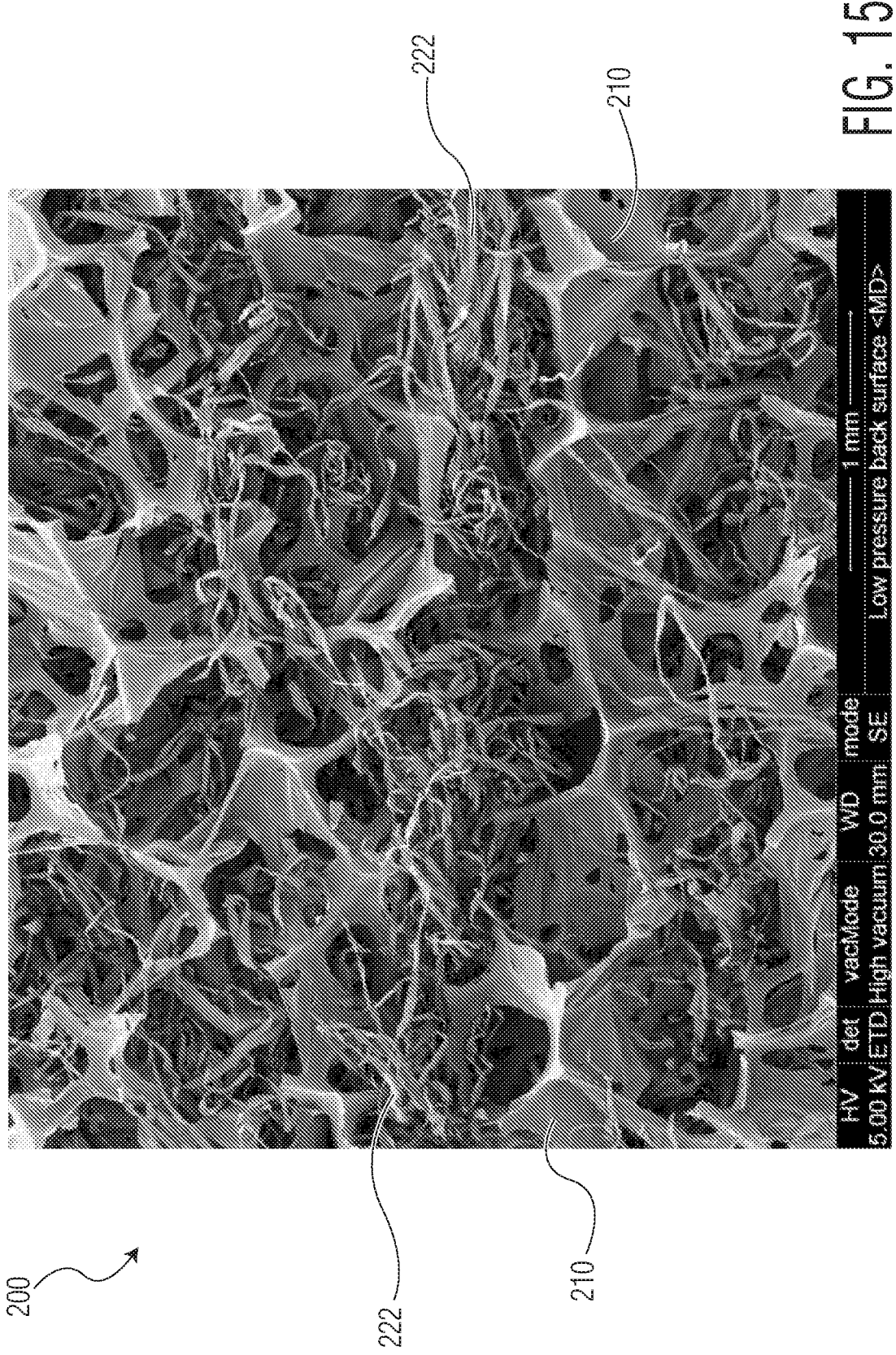
FIG. 15 is a photomicrograph of a planar view of the foam and fiber composite of FIG. 13 such that the second planar surface of the foam material and portions of fibers are visible to the viewer.

In various embodiments, the foam material can be hydrophobic and can have hydrophilic fibers inserted into the foam material to create a hydrophilic foam and fiber composite. The hydrophilic fibers within the foam material can provide a hydrophilic pathway through the foam material to direct body exudates through the foam material. Referring to FIGS. 13, 14, and 15, FIG. 13 is a photomicrograph (taken by scanning electron microscope at a magnification of 100×) of a cross-sectional view of a portion of a foam and fiber composite material 100 suitable for use as the exudate management layer 40, FIG. 14 is a photomicrograph (taken by scanning electron microscope at a magnification of 40×) of a planar view of the foam and fiber composite material 100 of FIG. 13 such that the fibrous material is visible to the viewer, and FIG. 15 is a photomicrograph (taken by scanning electron microscope at a magnification of 40×) of a planar view of the foam and fiber composite 100 of FIG. 13 such that the second planar surface of the foam material and portions of fibers are visible to the viewer. As is visible in FIGS. 13, 14, and 15, the foam and fiber composite material 100 can be formed of an open-cell foam material 110 and a fibrous material 120. The foam material 110 can have a first planar surface 112 and a second planar surface 114. In FIG. 13, each planar surface, 112 and 114, have been delineated by the corresponding broken lines for visual clarity. A layer of fibrous material 120 is in contact with one of the planar surfaces, such as planar surface 112, of the foam material 110. The layer of fibrous material 120 is formed from a plurality of individual fibers 122. As is visible in the foam and fiber composite material 100 shown in FIG. 13, a portion of the individual fibers 122 can extend from the fibrous material 120 and through the foam material 110 from the first planar surface 112 of the foam material 110 to the second planar surface 114 of the foam material 110. The foam and fiber composite 100 can have a total basis weight from about 20 gsm to about 250 gsm. The amount of fibrous material 120, including individual fibers 122 which are within the foam material, is at least about 10% of the total basis weight of the foam and fiber composite 100. In various embodiments, at least about 2, 5, 10, 15, 20, 30, 40, 50, 60 or 70 gsm of fibrous material 120 is brought into contact with a planar surface, such as planar surface 112 of the foam material 110. In various embodiments, the fibrous material 120 can be formed from a plurality of individual fibers 122. In various embodiments, the individual fibers 122 of the fibrous material 120 can be a loose configuration such as may occur with wet-laying or air-laying of the fibrous material 120. In various embodiments, the individual fibers 122 of the fibrous material 120 can be in the form of a nonwoven web of material such as, for example, a carded nonwoven web. The fibrous material 120 can, therefore, be manufactured via various processes such as, but not limited to, air-laying, wet-laying, and carding. In various embodiments, the fibers 122 forming the fibrous material 120 can be hydrophilic. The fibers 122 can be naturally hydrophilic or can be fibers which are naturally hydrophobic but which have been treated to be hydrophilic, such as, for example, via a treatment with a surfactant. Providing hydrophilic fibers 122 can allow for a foam and fiber composite 100 which can have hydrophilic pathways through the foam material 110. In various embodiments in which the foam material 110 is hydrophobic, the hydrophilic pathways provided by the hydrophilic fibers 122 can allow for the foam and fiber composite 100 in an absorbent article 10 to intake bodily exudates (via the hydrophilic fiber pathways) and maintain the body exudates in a location away from the topsheet layer 30 of the absorbent article 10 as the body exudates will not be able to readily pass through the hydrophobic foam material 110. In various embodiments, the fibers 122 forming the fibrous material 120 can be cellulosic fibers such as, but not limited to, cotton, ramie, jute, hemp, flax, bagasse, northern softwood kraft pulp, as well as synthetic cellulosic fibers such as, but not limited to, rayon, viscose, and cellulosic acetate. In various embodiments, the fibers 122 forming the fibrous material 120 can be synthetic fibers made from polymers such as polyethylene, polypropylene, aromatic polyesters, aliphatic polyesters, and polyamides. In such embodiments, the fibers 122 can be treated with additives to impart various degrees of surface energy ranging from very low surface energy and low wettability to high surface energy and high wettability.

The exudate management layer 40 is formed from a base sheet of material, such as any of the materials described above, and is configured to have a first component 50 which at least partially defines an opening 42 for direct passage of body exudates into the absorbent core 38 and a second component 60 connected to the first component 50. The first component 50 can provide the exudate management layer 40 with a first height dimension 76 and the second component 60 can provide the exudate management layer 40 with a second height dimension 78 that can be greater than the first height dimension 76.

The first component 50 of the exudate management layer 40 can have a first transverse direction end edge 52, a second transverse direction end edge 54, and an opposing pair of longitudinal direction side edges 56 extending between and connecting the transverse direction end edges, 52 and 54. The first component 50 can generally have any shape and/or size desired. In various embodiments, for example, the first component 50 can have a rectangular shape, a curved rectangular shape, an oval shape, an elliptical shape, a circular shape, an hourglass shape, a square shape, or a curved square shape. In various embodiments, each of the edges, 52, 54, and 56, of the first component 50 can be straight. In various embodiments, at least one of the edges, 52, 54, or 56, of the first component 50 can be arcuate and the remaining edges can be straight. In various embodiments, at least two of the edges, 52, 54, or 56, of the first component 50 can be arcuate and the remaining edges can be straight. In various embodiments, for example, the longitudinal direction side edges 56 of the first component 50 can be straight and the transverse direction end edges, 52 and 54, can be arcuate. In various embodiments, the transverse direction end edges, 52 and 54, can have an arcuate shape which can form a complementary configuration with each other if the two edges, 52 and 54, were to be brought together. In various embodiments, at least three of the edges, 52, 54, or 56, of the first component 50 can be arcuate and the remaining edge can be straight. In various embodiments, all of the edges, 52, 54, and 56, of the first component 50 can be arcuate.

In various embodiments, the first component 50 can have a longitudinal direction length as measured from the first transverse direction end edge 52 to the second transverse direction end edge 54 which can be less than the overall length of the absorbent article 10. For example, the first component 50 can have a longitudinal length between about 20, 30, 40, 50, or 60 mm to about 100, 150, 175, 200, 250, or 300 mm. In various embodiments, the first component 50 can have a longitudinal direction length that is from about 15, 20, 25, 30, 35, or 40% to about 50, 55, 60, 65, 70, 75, 80, 85, or 90% of the longitudinal length of the absorbent article 10. In various embodiments, the first component 50 can have a transverse width as measured form a first longitudinal direction side edge 56 to a second longitudinal direction side edge 56 which can be equal to or less than the overall width of the absorbent article 10. For example, the first component 50 can have a transverse width between about 10, 15, 20, or 30 mm to about 60, 80, 100, 110, 115, 120, 125, 130, 140, or 150 mm. In various embodiments, the first component 50 can have a transverse width that is from about 15, 20, 25, 30, 35, of 40% to about 50, 55, 60, 65, 70, 75, 80, 85, or 90% of the transverse width of the absorbent article 10. The first component 50 has a body facing surface 72 and a garment facing surface 74. The first component 50 can provide the exudate management layer 40 with a first height dimension 76 in the depth direction (Z) of the exudate management layer 40. In various embodiments, the first height dimension 76 can be from about 0.5, 0.75, 1, 1.5, 2, or 3.5 mm to about 3, 3.5, 4, 4.5, 5, 6, or 10 mm.

To enhance the ability of the absorbent article 10 to transfer body exudates in the depth direction (Z) as well as to enhance the ability of the exudate management layer 40 to conform to the wearer's body based on its ability to bend, the first component 50 of the exudate management layer 40 can have an opening 42 which can be any suitable shape, such as, but not limited to, ovular, circular, rectangular, square, elliptical, hourglass, triangular, etc. In various embodiments, the shape of the opening 42 can include a shape of a physical object, such as, for example, the outer shape of a leaf, an animal, a star, a heart, a tear drop, a moon, or an abstract configuration. In various embodiments, the opening 42 in the first component 50 can be elongate and can be oriented in the longitudinal direction (X) of the absorbent article 10. The opening 42 can be bounded at least partially by a perimeter 44, which can form an inner border or inner edge of the first component 50, and bounded at least partially by a primary fold 70 connecting the first component 50 to a second component 60 of the exudate management layer 40. The opening 42 passes through the first component 50 from the body facing surface 72 of the first component to the garment facing surface 74 of the first component 50. The opening 42 can form a cup or well-like structure for holding body exudates and preventing its leakage away from a region of the absorbent article 10 and towards the edges of the absorbent article 10.

The opening 42 can be located at various positions along the longitudinal and transverse directions of the absorbent article 10 depending upon the primary location of body exudate intake within the absorbent article 10. This variability in positioning allows the opening 42 to be positioned below the main point of body exudate discharge so that it can act as the primary body exudate receiving area for the absorbent article 10. For example, in various embodiments, the absorbent article 10 can have a longitudinal centerline 18 and a transverse centerline 80. It should be understood that the longitudinal centerline 18 is disposed at a distance that is equidistant from the longitudinal direction side edges 24 and runs the length of the absorbent article 10 in the longitudinal direction (X), while the transverse centerline 80 is disposed at a location that is equidistant from the first transverse direction end edge 20 and the second transverse direction end edge 22 and runs along the width of the absorbent article 10 in the transverse direction (Y). In various embodiments, the opening 42 of the exudate management layer 40 can be positioned so that it is in symmetrical alignment with the longitudinal centerline 18 and the transverse centerline 80 of the absorbent article 10. This allows the opening 42 to be centrally disposed within the absorbent article 10. However, centralized positioning of the opening 42 in the absorbent article 10 is not required and, in various embodiments, depending on the primary location where body exudate intake might occur within the absorbent article 10, the opening 42 of the exudate management layer 40 may be either symmetrical about the longitudinal centerline 18 only or may not be symmetrical about either the longitudinal centerline 18 or the transverse centerline 80. In various embodiments, it may be desirable for the opening 42 to be shifted in the longitudinal direction (X) towards the posterior region 14 transverse direction end edge 22 to provide an absorbent article 10 with an improved ability to receive and isolate body exudate such as fecal material. Providing an absorbent article 10 with a structure that can receive and isolate fecal material can reduce the incidence of the fecal material contacting the wearer's genitalia as well as reduce the incidence of leakage of the fecal material from the absorbent article 10. In various embodiments, the opening 42 of the exudate management layer 40 may be symmetrical about the longitudinal centerline 18 and asymmetrical about the transverse centerline 80. In various embodiments, the opening 42 of the exudate management layer 40 may be asymmetrical about each of the longitudinal centerline 18 and the transverse centerline 80. In various embodiments, the opening 42 of the exudate management layer 40 can be positioned between the transverse centerline 80 and the posterior region 14 transverse direction end edge 22 of the absorbent article 10. In such embodiments, the opening 42 of the exudate management layer 40 may or may not be symmetrical about the longitudinal centerline 18.

The opening 42 in the exudate management layer 40 can have a longitudinal length from about 15, 20, 30, or 50 mm to about 60, 75, 100, or 150 mm and can have a transverse width from about 10, 15, 20, or 30 mm to about 40, 60, 80, 100, 110, 120, or 130 mm. The opening 42 in the exudate management layer 40 can have a longitudinal length that is from about 15, 20, or 25% to about 70, 75, or 80% of the overall longitudinal length of the first component 50 in the longitudinal direction (X). The opening 42 in the exudate management layer 40 can have a transverse width that can be from about 20, 25, or 30% to about 70, 75, or 80% of the overall width of the first component 50 in the transverse direction (Y). The opening 42 of the exudate management layer 40 can be sized as deemed suitable for the receipt and isolation of fecal material within the absorbent article 10.

In addition to the first component 50, the exudate management layer 40 has a second component 60 which is in an at least partially overlapping configuration with the first component 50. The second component 60 is formed from the same base sheet of material forming the first component 50 of the exudate management layer 40 and is connected to the first component 50 via a primary fold 70 in the material forming the exudate management layer 40. The second component 60 of the exudate management layer 40 extends from the primary fold 70 in the longitudinal direction (X) of the absorbent article 10 in a direction towards the posterior region 14 of the absorbent article 10. The second component 60 can help shape the absorbent article 10, create a close-to-body fit, and absorb fluid from a wearer's buttock's region. In various embodiments, the second component 60 can extend beyond the second transverse direction end edge 54 of the first component 50. In various embodiments, the second component 60 may not extend beyond the second transverse direction end edge 54 of the first component 50.

The second component 60 can have a first transverse direction end edge 62 which is coextensive with the primary fold 70, a second transverse direction end edge 64 and an opposing pair of longitudinal direction side edges 66 extending between and connecting the transverse direction end edges, 62 and 64. The second component 60 can generally have any shape and/or size desired. The second component 60 is created by cutting, punching, or otherwise separating the material forming the second component 60 from the material forming the first component 50. Such cutting, punching, or otherwise separating of the second component 60 from the first component 50 will result in the perimeter 44 which at least partially defines the opening 42 in the first component 50. The second component 60 is positioned into an at least partially overlapping configuration with the first component 50 by incorporating a primary fold 70 into the material forming the exudate management layer 40. The second component 60 is not fully separated from the first component 50 and remains attached to the first component 50 via the primary fold 70. In various embodiments, as the formation of the second component 60 results in the formation of the opening 42, the second component 60 can have a shape and size which can be considered a mate of and is complementary to the shape and size of the opening 42. In such embodiments, the second component 60 therefore, when not in an at least partially overlapping configuration with the first component 50, can fit entirely within the opening 42 of the exudate management layer 40 and the edges, 64 and 66, of the second component 60 can be adjacent to the perimeter 44 of the first component 50. In various embodiments, the second component 60 can be smaller in dimension than the opening 42, such as, for example, if the second component 60 is further reduced in size dimension. In such embodiments, the second component 60 can fit entirely within the opening 42 of the exudate management layer 40 but the edges of the second component 60 may not be adjacent to the perimeter 44 of the first component 50. In various embodiments, a portion of the second component 60 may be removed from the second component 60 as part of the cutting or punching to form the second component 60 such that the second component 60 is not a perfect mate or is not exactly complementary to the shape and size of the opening 42.

The second component 60 can have a longitudinal length from about 15, 20, 30, or 50 mm to about 60, 75, 100, or 150 mm and can have a transverse width from about 10, 15, 20, or 30 mm to about 40, 60, 80, 100, 110, 120, or 130 mm. In various embodiments, the second component 60 can have a longitudinal direction length that is from about 15, 20, 25, 30, 35, or 40% to about 50, 55, 60, 65, 70, 75, 80, 85, or 90% of the longitudinal length of the first component 50. In various embodiments, the second component 60 can have a transverse width that is from about 15, 20, 25, 30, 35, or 40% to about 50, 55, 60, 65, 70, 75, 80, 85, or 90% of the transverse width of the first component 50. In various embodiments, the second transverse direction end edge 64 of the second component 60 can be from about 15 mm to about 75 mm from the second transverse direction end edge 22 of the absorbent article 10. The second component 60 can provide a height dimension 78 to the exudate management layer 40 and the second height dimension 78, in the depth direction (Z), can be from about 0.5, 0.75, 1, 1.5, 2, 3, 3.5, 4, 4.5, 5, 5.5, 6, 6.5, 7, 7.5, 8, 8.5, 9, 9.5, or 10 mm to about 10.5, 11, 11.5, 12, 12.5, 13, 13.5, 14, 14.5, 15, 15.5, 16, 16.5, 17, 17.5, 18, 18.5, 19, 19.5, or 20 mm.

The first component 50 and the second component 60 can be in an at least partially overlapping configuration with each other. In various embodiments, the second component 60 can overlap a portion of the first component 50 such that the second component 60 is in contact with a portion of the body facing surface 72 of the first component 50. In various embodiments, the portion of the second component 60 in contact with the portion of the body facing surface 72 of the first component 50 can be bonded to each other such as, for example, by adhesive bonding, thermal bonding, ultrasonic bonding, etc. FIGS. 3, 4A, 4B, 8A, and 8B provide exemplary illustrations of embodiments in which the second component 60 overlaps a portion of the first component 50 so that the second component 60 is in contact with a portion of the body facing surface 72 of the first component 50. In various embodiments, the second component 60 can underlap a portion of the first component 50 such that the second component 60 is in contact with a portion of the garment facing surface 74 of the first component 50. In various embodiments, the portion of the second component 60 in contact with the portion of the garment facing surface 74 of the first component 50 can be bonded to each other such as, for example, by adhesive bonding, thermal bonding, ultrasonic bonding, etc. FIGS. 5, 6A, 6B, 9A, and 9B, provide exemplary illustrations of embodiments in which the second component 60 underlaps a portion of the first component 50 so that the second component 60 is in contact with a portion of the garment facing surface 74 of the first component 50.

Figure 3:
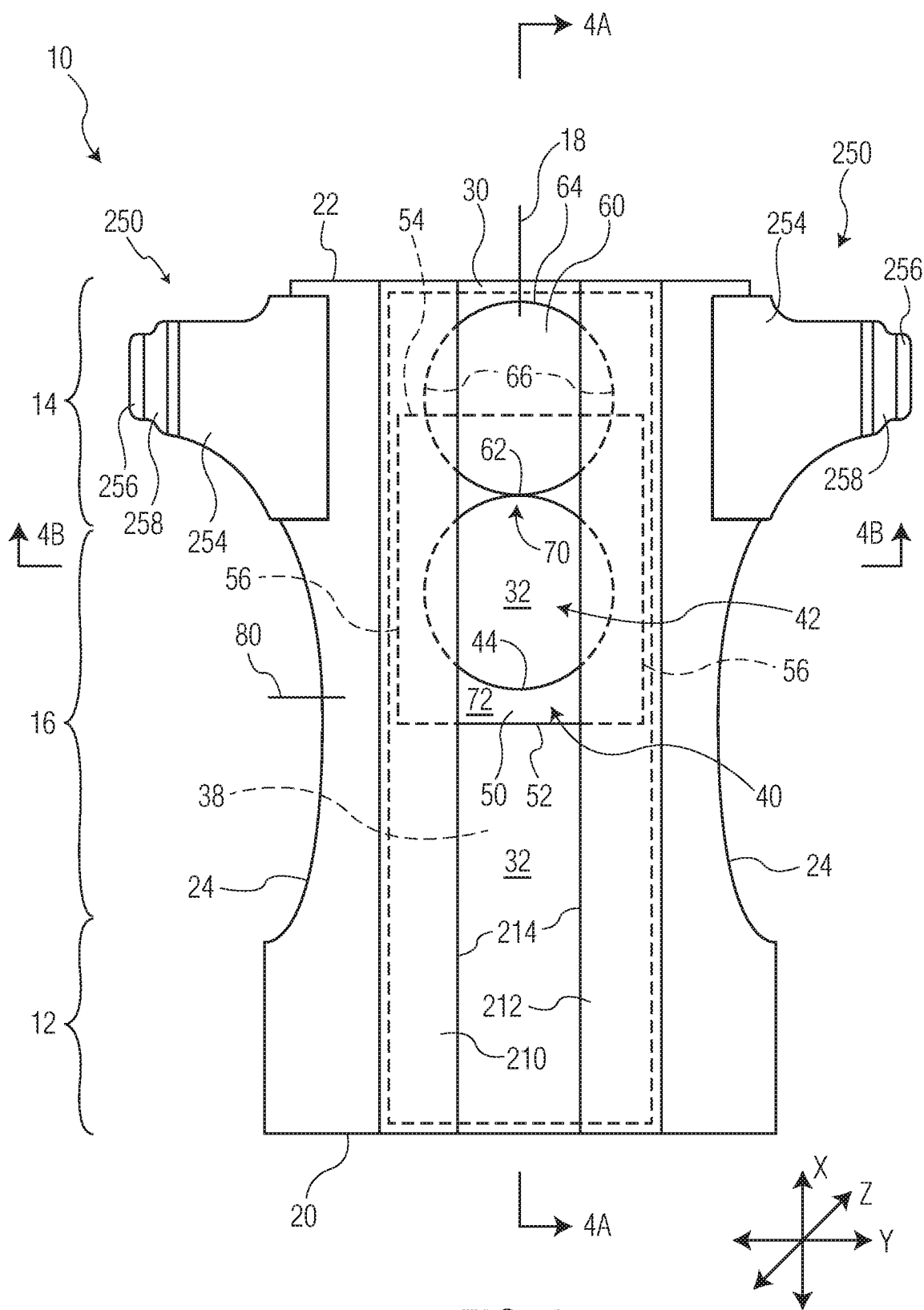
FIG. 3 is a top down view of an exemplary embodiment of an absorbent article.
Figure 4A:
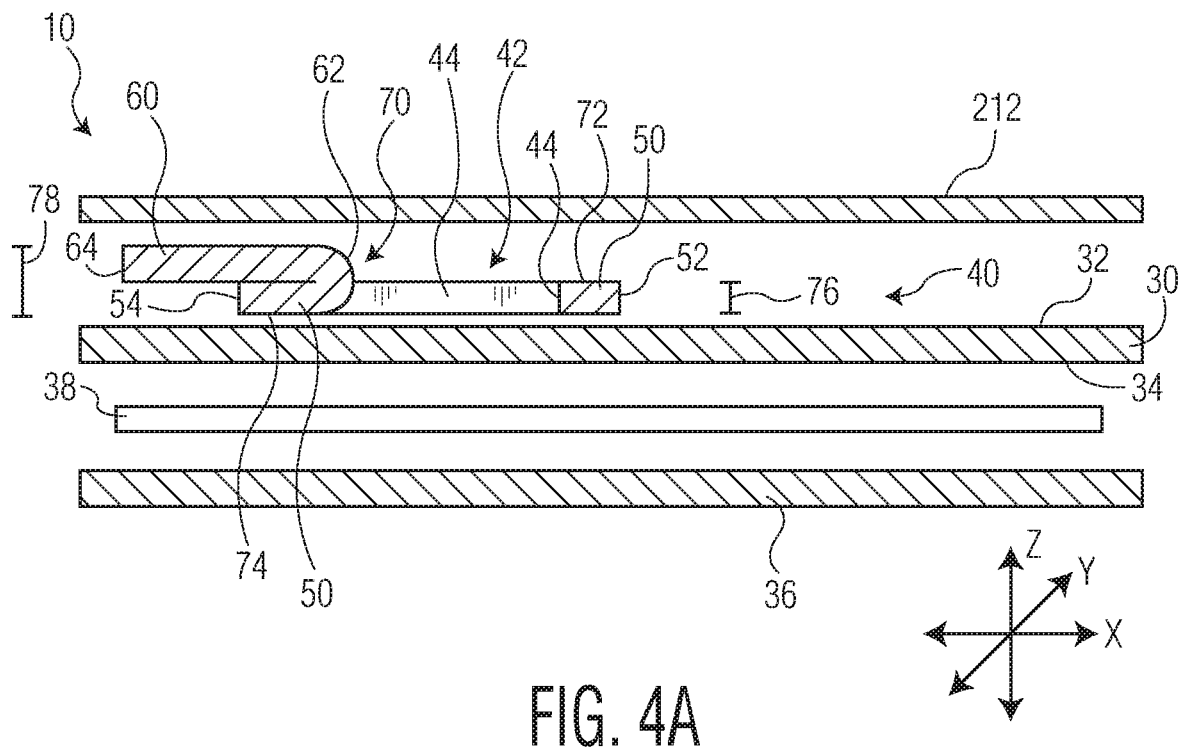
FIG. 4A is an exploded cross-sectional view of the absorbent article of FIG. 3 taken along line 4A-4A.
Figure 4B:
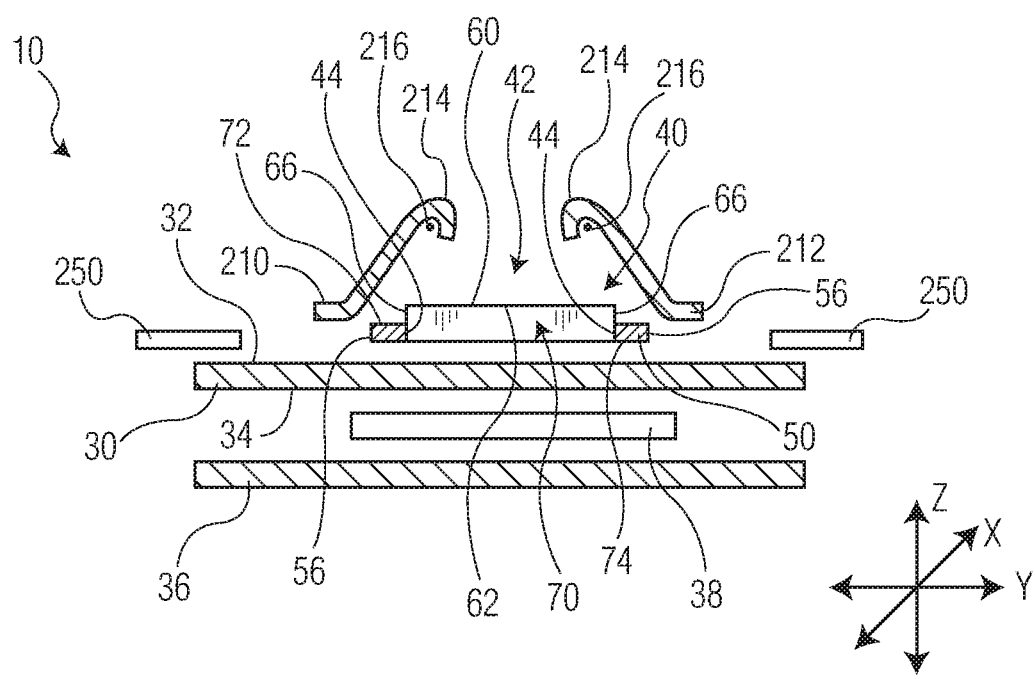
FIG. 4B is an exploded cross-sectional view of the absorbent article of FIG. 3 taken along line 4B-4B.

FIGS. 3, 4A, and 4B provide an exemplary illustration of an absorbent article 10 having an exudate management layer 40 in fluid communication with the topsheet layer 30 of the absorbent article 10. In the embodiment illustrated in FIGS. 3, 4A, and 4B, the exudate management layer 40 is positioned on the body facing surface 32 of the topsheet layer 30. The opening 42 of the exudate management layer 40 is positioned such that the opening 42 is symmetrical about the longitudinal centerline 18 but not symmetrical about the transverse centerline 80. The opening 42 of the exudate management layer 40 illustrated in FIGS. 3, 4A, and 4B is positioned between the transverse centerline 80 and the posterior region 14 transverse direction end edge 22. The transverse width of the first component 50 is uniform in the longitudinal direction of the first component 50. The exudate management layer 40 is configured such that the second component 60 is in an at least partially overlapping configuration with the first component 50 such that a portion of the second component 60 is in contact with a portion of the body facing surface 72 of the first component 50. The opening 42 of the exudate management layer 40 is generally circular in shape.

Figure 5:
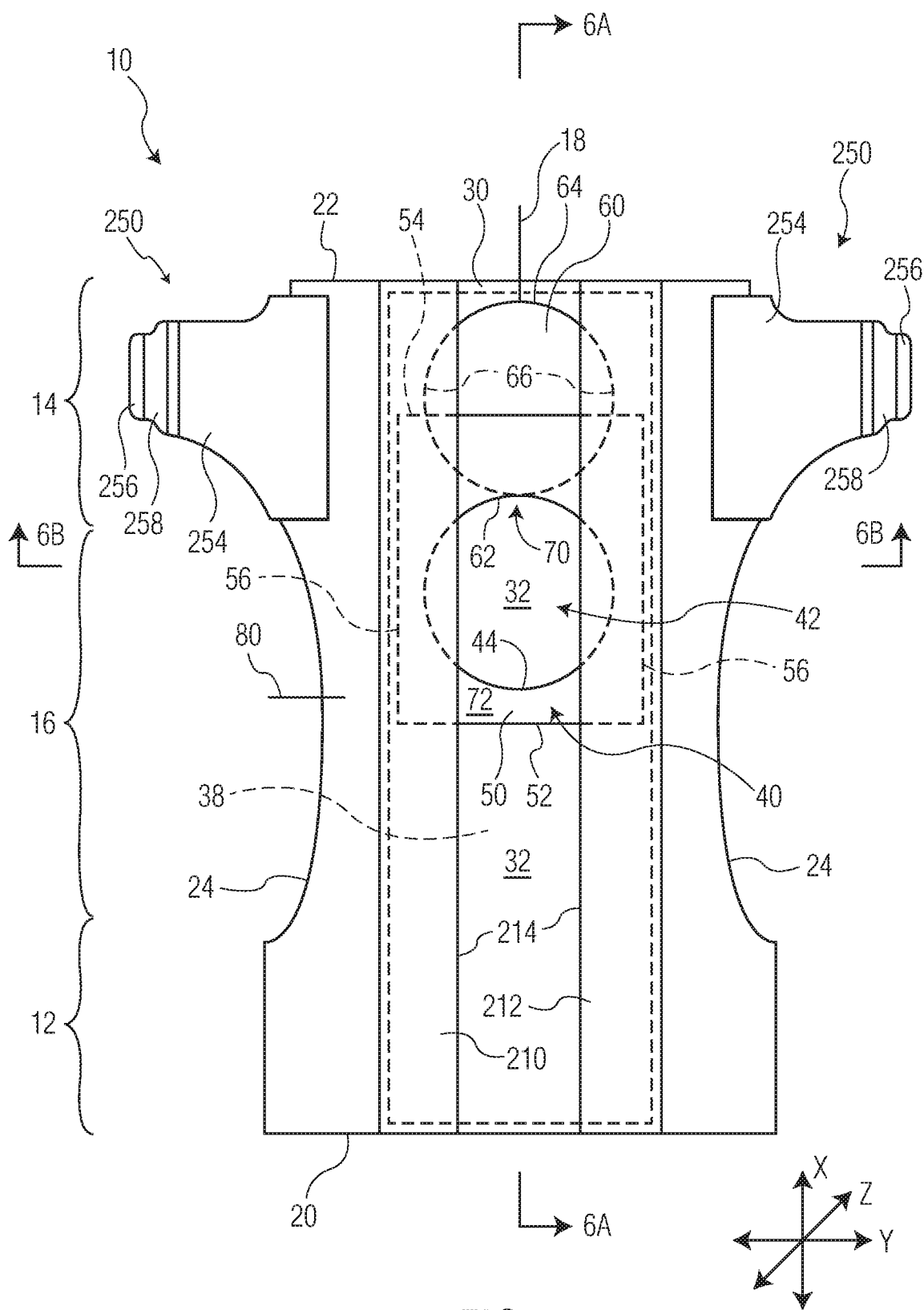
FIG. 5 is a top down view of an exemplary embodiment of an absorbent article.
Figure 6A:
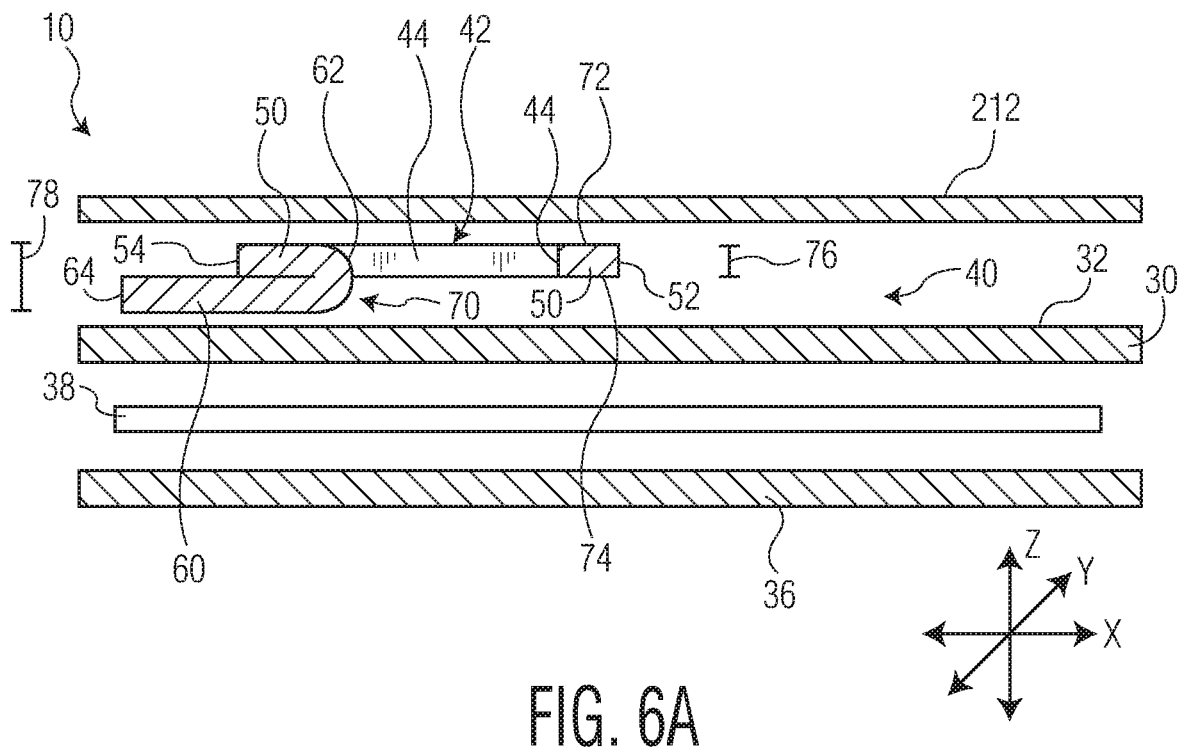
FIG. 6A is an exploded cross-sectional view of the absorbent article of FIG. 5 taken along line 6A-6A.
Figure 6B:
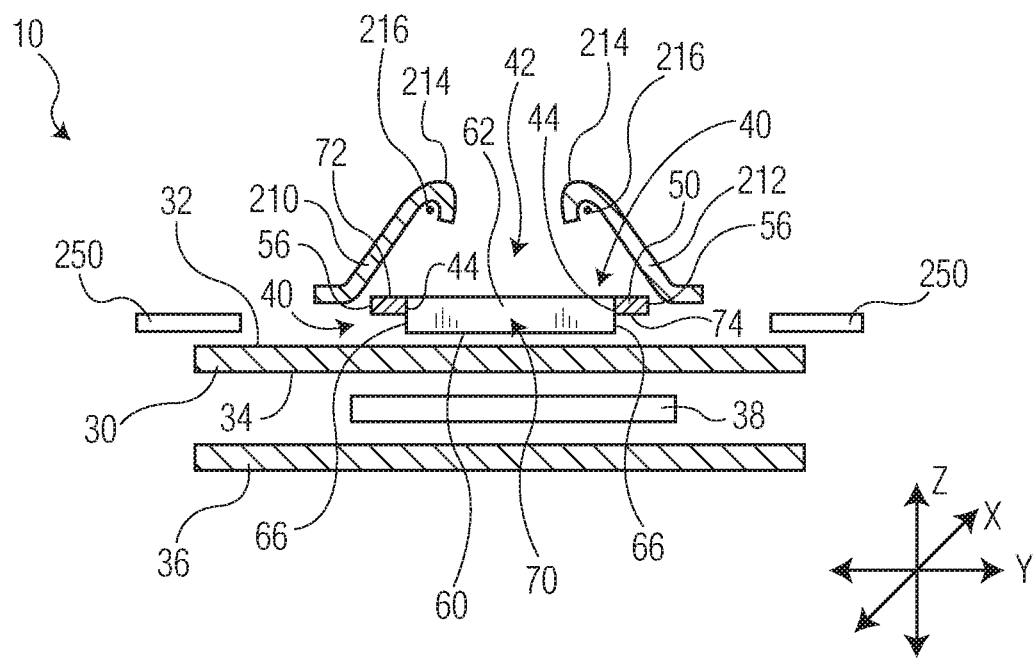
FIG. 6B is an exploded cross-sectional view of the absorbent article of FIG. 5 taken along line 6B-6B.

FIGS. 5, 6A, and 6B provide an exemplary illustration of an absorbent article 10 having an exudate management layer 40 in fluid communication with the topsheet layer 30 of the absorbent article 10. In the embodiment illustrated in FIGS. 5, 6A, and 6B, the exudate management layer 40 is positioned on the body facing surface 32 of the topsheet layer 30. The opening 42 of the exudate management layer 40 is positioned such that the opening 42 is symmetrical about the longitudinal centerline 18 but not symmetrical about the transverse centerline 80. The opening 42 of the exudate management layer 40 illustrated in FIGS. 5, 6A, and 6B, is positioned between the transverse centerline 80 and the posterior region 14 transverse direction end edge 22. The transverse width of the first component 50 is uniform in the longitudinal direction of the first component 50. The exudate management layer 40 is configured such that the second component 60 is in an at least partially underlapping configuration with the first component 50 such that a portion of the second component 60 is in contact with a portion of the garment facing surface 74 of the first component 50. The opening 42 of the exudate management layer 40 is generally circular in shape.

Figure 7:
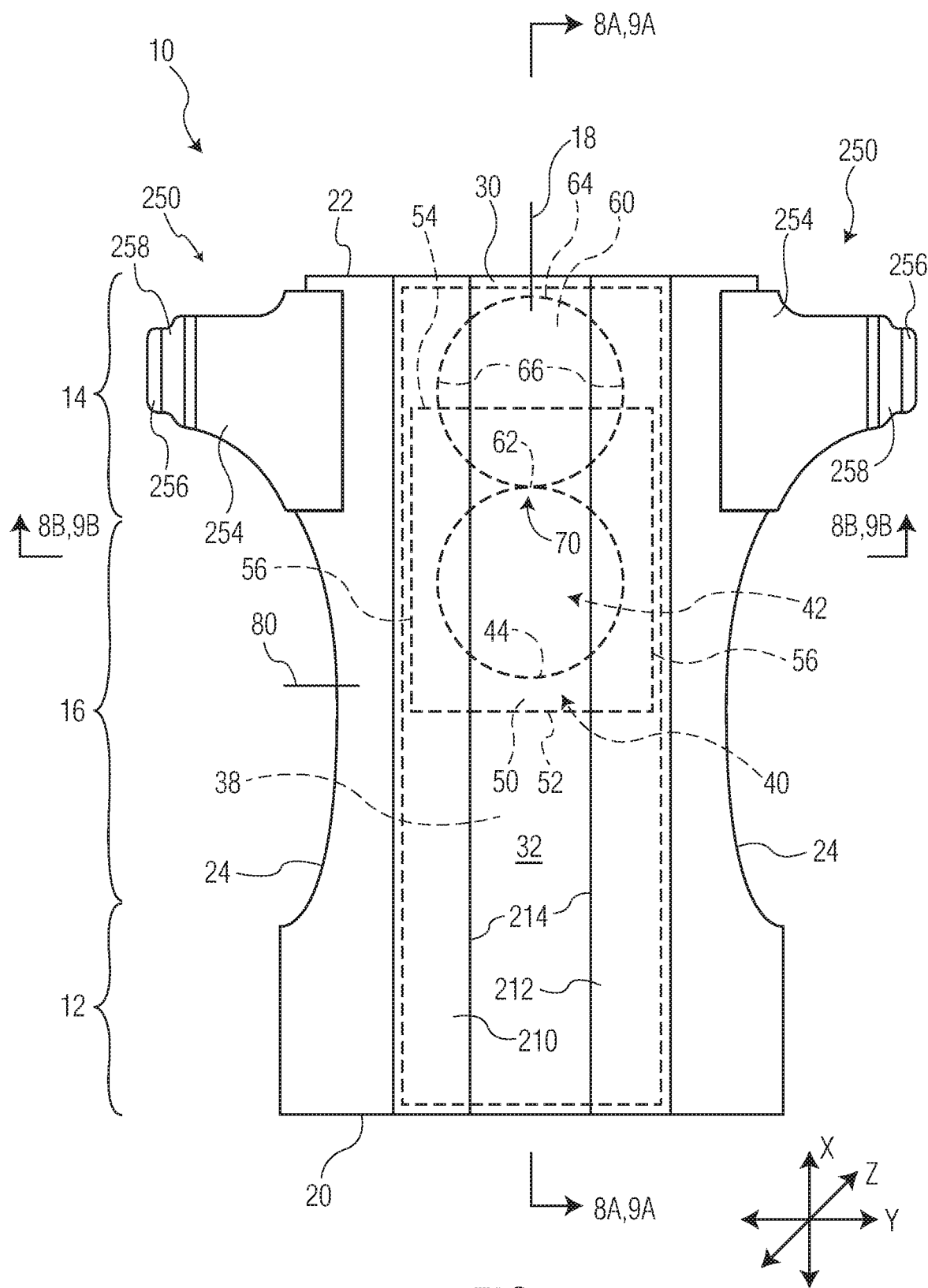
FIG. 7 is a top down view of an exemplary embodiment of an absorbent article.
Figure 8A:
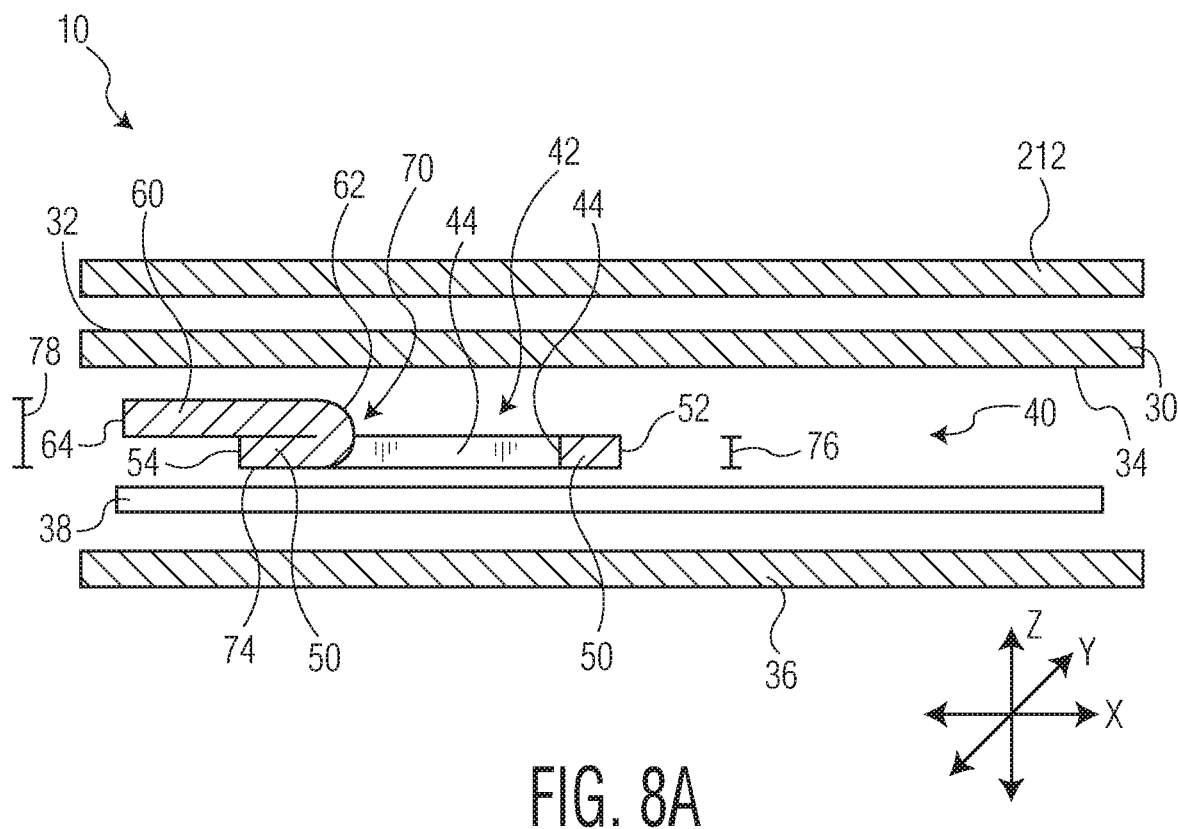
FIG. 8A is an exploded cross-sectional view of an exemplary embodiment of the absorbent article of FIG. 7 taken along line 8A-8A.
Figure 8B:
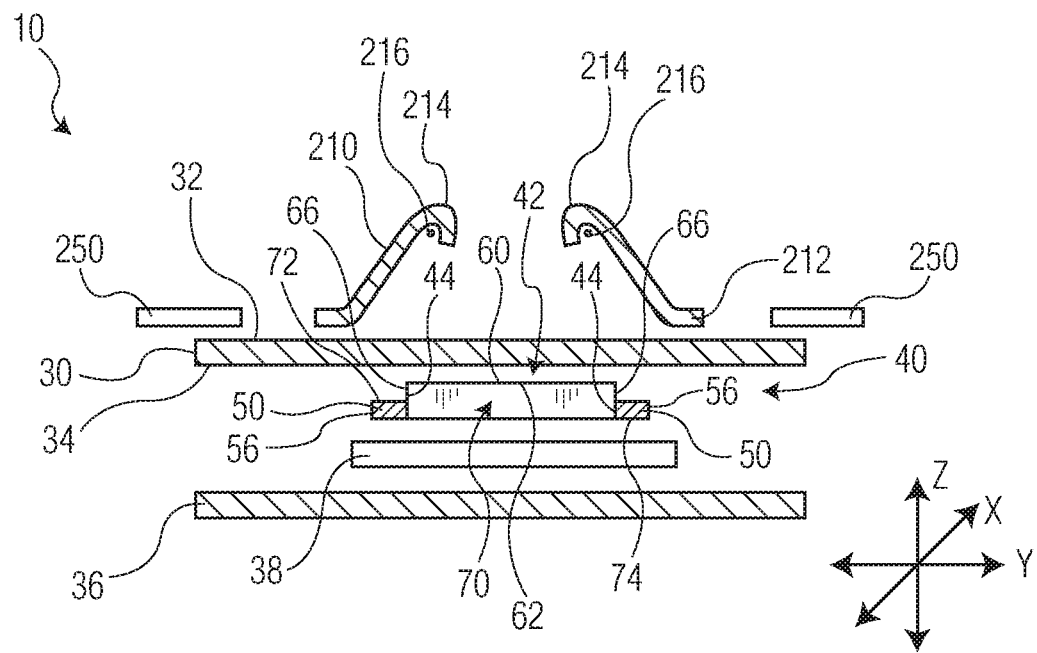
FIG. 8B is an exploded cross-sectional view of an exemplary embodiment of the absorbent article of FIG. 7 taken along line 8B-8B.
Figure 9A:
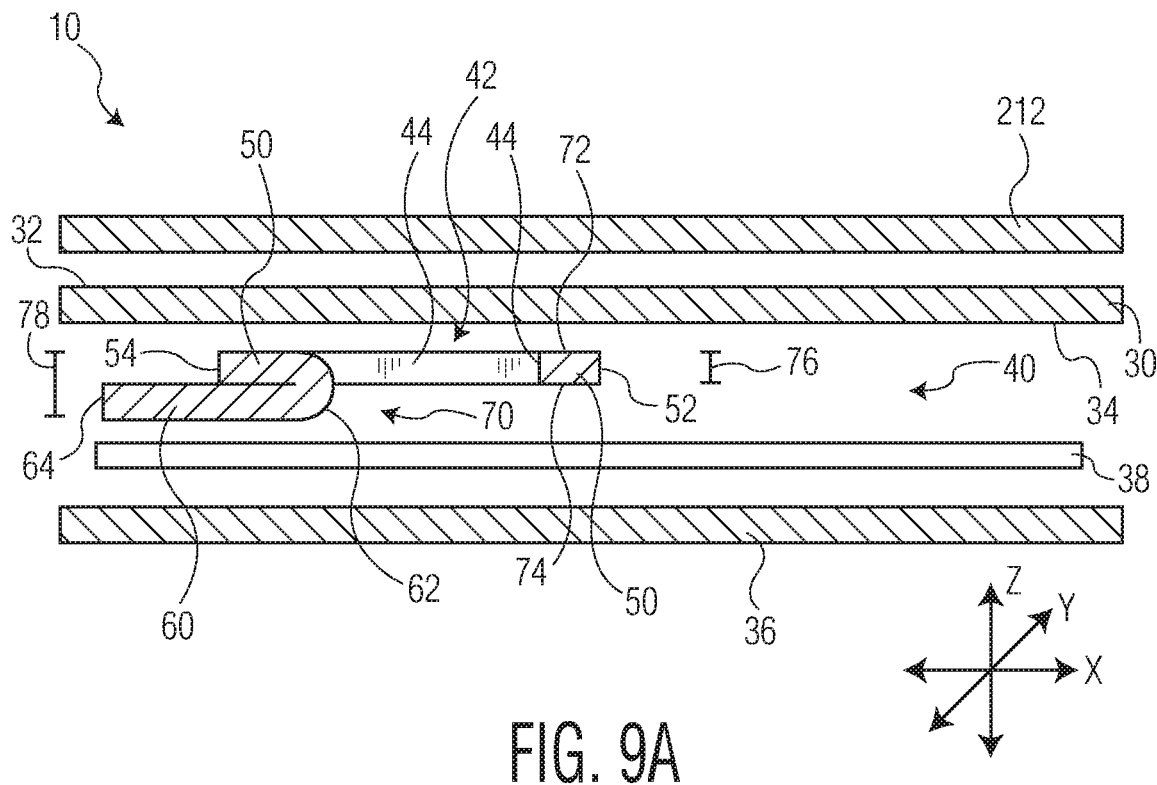
FIG. 9A is an exploded cross-sectional view of another exemplary embodiment of the absorbent article of FIG. 7 taken along line 9A-9A.
Figure 9B:
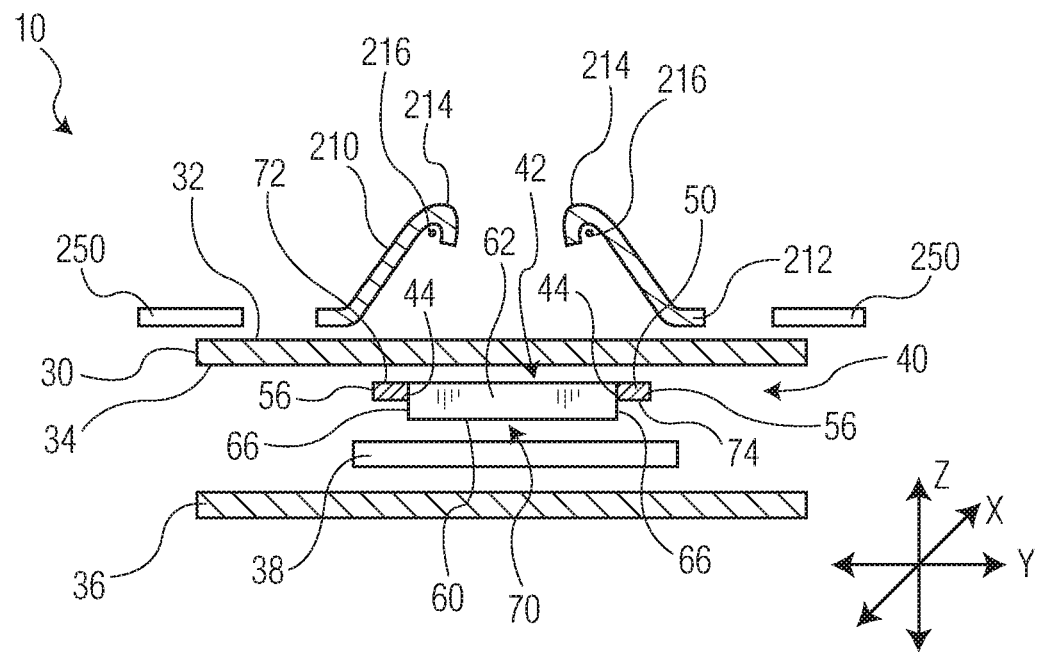
FIG. 9B is an exploded cross-sectional view of another exemplary embodiment of the absorbent article of FIG. 7 taken along line 9B-9B.

FIG. 7 provides an exemplary illustration of an absorbent article 10 having an exudate management layer 40 in fluid communication with the topsheet layer 30 of the absorbent article 10. In the embodiment illustrated in FIG. 7, the exudate management layer is positioned between the topsheet layer 30 and the absorbent core 38 of the absorbent article 10. The exudate management layer 40 can be in contact with the garment facing surface 34 of the topsheet layer 30. The opening 42 of the exudate management layer 40 is positioned such that the opening 42 is symmetrical about the longitudinal centerline 18 but not symmetrical about the transverse centerline 80. The opening 42 of the exudate management layer 40 is positioned between the transverse centerline 80 and the posterior region 14 transverse direction end edge 22. The transverse width of the first component 50 is uniform in the longitudinal direction of the first component 50. FIGS. 8A and 8B provide exemplary illustrations of an embodiment of an exudate management layer 40 which can be present in the absorbent article 10 of FIG. 7. As illustrated in FIGS. 8A and 8B, the exudate management layer is configured such that the second component 60 is in an at least partially overlapping configuration with the first component 50 such that a portion of the second component 60 is in contact with a portion of the body facing surface 72 of the first component 50. The opening 42 of the exudate management layer 40 is generally circular in shape. FIG. 9A and 9B provide exemplary illustrations of an embodiment of an exudate management layer 40 which can be present in the absorbent article 10 of FIG. 7. As illustrated in FIGS. 9A and 9B, the exudate management layer is configured such that the second component 60 is in an at least partially underlapping configuration with the first component 50 such that a portion of the second component 60 is in contact with a portion of the garment facing surface 74 of the first component 50. The opening 42 of the exudate management layer 40 is generally circular in shape.

Figure 16A:
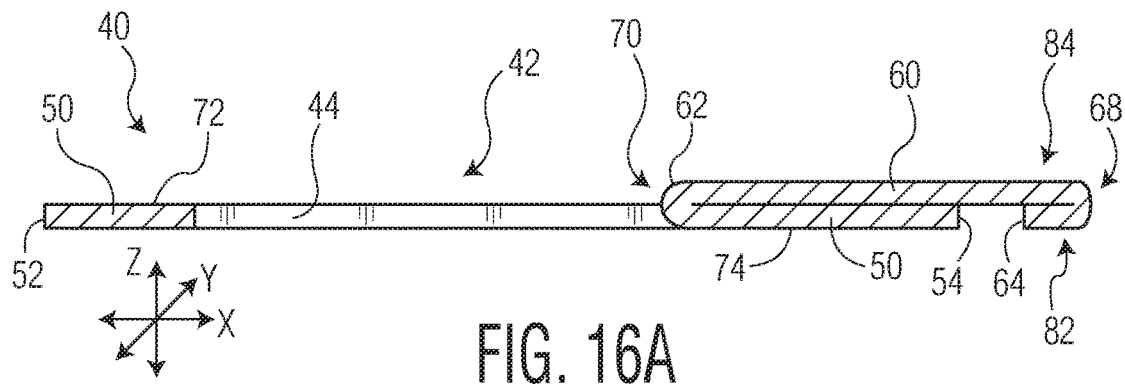
FIGS. 16A-16D are cross-sectional side views taken in the longitudinal direction of exemplary embodiments of exudate management layers.
Figure 16B:
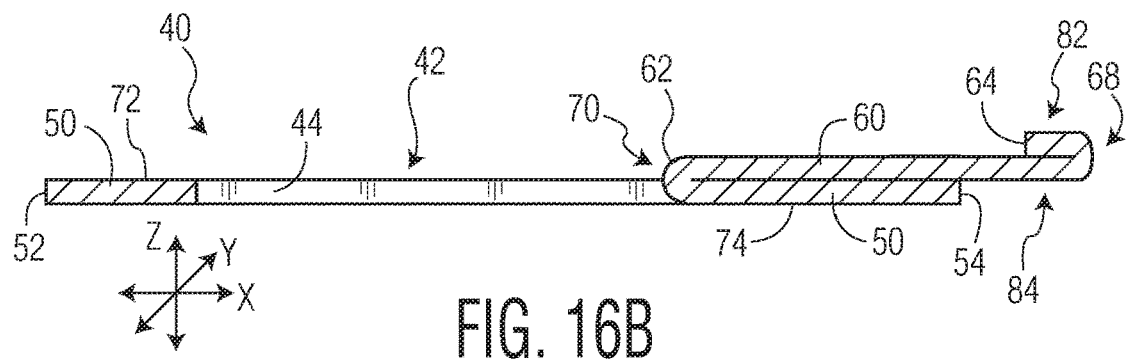
Figure 16C:
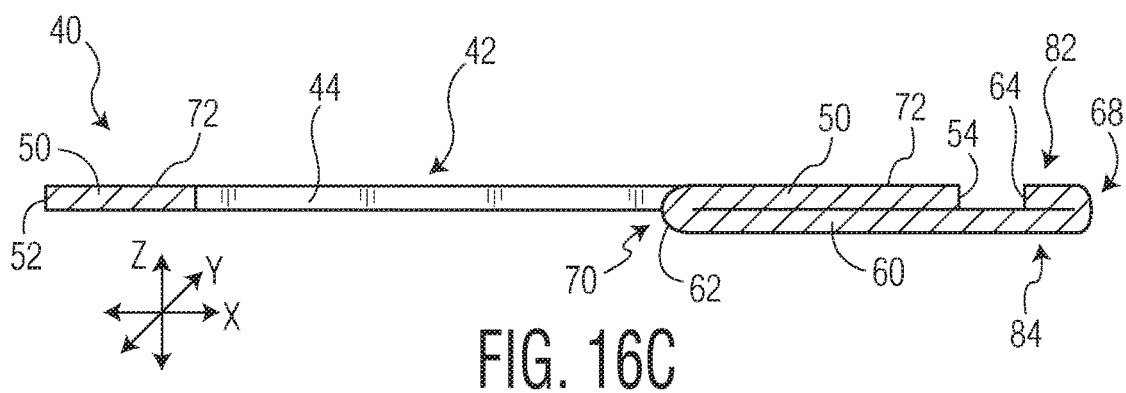
Figure 16D:
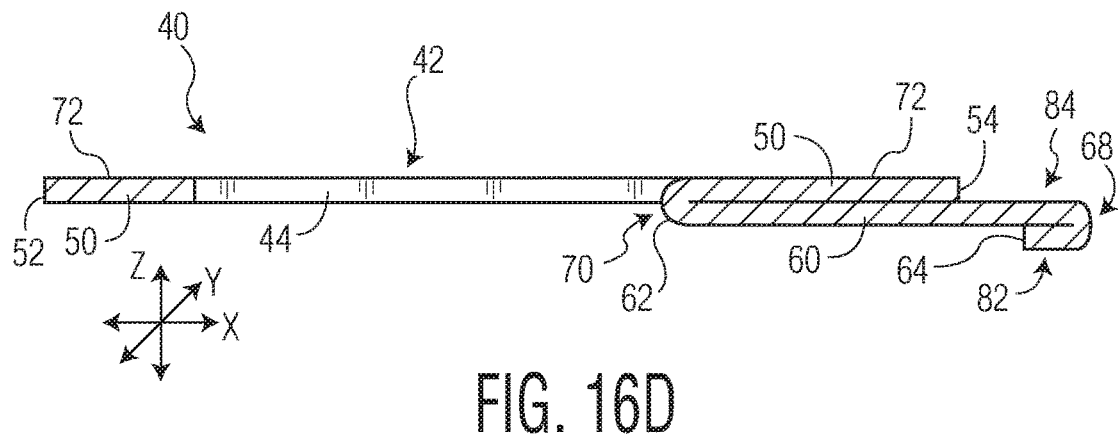

In various embodiments, the second component 60 can have a secondary fold 68. The secondary fold 68 can be a fold within the second component 60 and can bring a first portion 82 of the second component 60 into contact with a second portion 84 of the second component 60. FIGS. 16A-16D provide exemplary illustrations of cross-sectional side views taken in the longitudinal direction of exemplary exudate management layers 40 in which the second component 60 has a secondary fold 68. The exudate management layer 40 illustrated in FIGS. 16A-16D has a first component 50 connected to a second component 60 via the primary fold 70 and wherein the first component 50 and the second component 60 are in a partially overlapping configuration. Referring to FIG. 16A, the second component 60 is in an at least partially overlapping configuration with the first component 50 such that the second component 60 is in contact with a portion of the body facing surface 72 of the first component 50. The second component 60 further has a secondary fold 68 which brings a first portion 82 of the second component 60 into contact with a second portion 84 of the second component 60. The first portion 82 can be in an underlapping configuration with the second portion 84 of the second component 60. Referring to FIG. 16B, the second component 60 is in an at least partially overlapping configuration with the first component 50 such that the second component 60 is in contact with a portion of the body facing surface 72 of the first component 50. The second component 60 further has a secondary fold 68 which brings a first portion 82 of the second component 60 into contact with a second portion 84 of the second component 60. The first portion 82 can be in an overlapping configuration with the second portion 84 of the second component 60. Referring to FIG. 16C, the second component 60 is in an at least partially underlapping configuration with the first component 50 such that the second component 60 is in contact with a portion of the garment facing surface 74 of the first component 50. The second component 60 further has a secondary fold 68 which brings a first portion 82 of the second component 60 into contact with a second portion 84 of the second component 60. The first portion 82 can be in an overlapping configuration with the second portion 84 of the second component 60. Referring to FIG. 16D, the second component 60 is in an at least partially underlapping configuration with the first component 50 such that the second component 60 is in contact with a portion of the garment facing surface 74 of the first component 50. The second component 60 further has a secondary fold 68 which brings a first portion 82 of the second component 60 into contact with a second portion 84 of the second component. While the embodiments illustrated in FIGS. 16A-16D illustrate a single secondary fold 68 in the second components 60, it is to be understood that the second component 68 can have more than one secondary fold 68. While the embodiments illustrated in FIGS. 16A-16D illustrate the secondary fold 68 of the second component 60 to be in a location beyond the second transverse direction end edge 54 of the first component 50, it is to be understood that the secondary fold 68 can occur close in proximity to the second transverse direction end edge 54 of the first component 50 or can occur such that the resulting overlapping configuration of a first portion 82 and second portion 84 of the second component 60 can occur in an overlapping configuration with the first component 50 of the exudate management layer 40.

Figure 17:
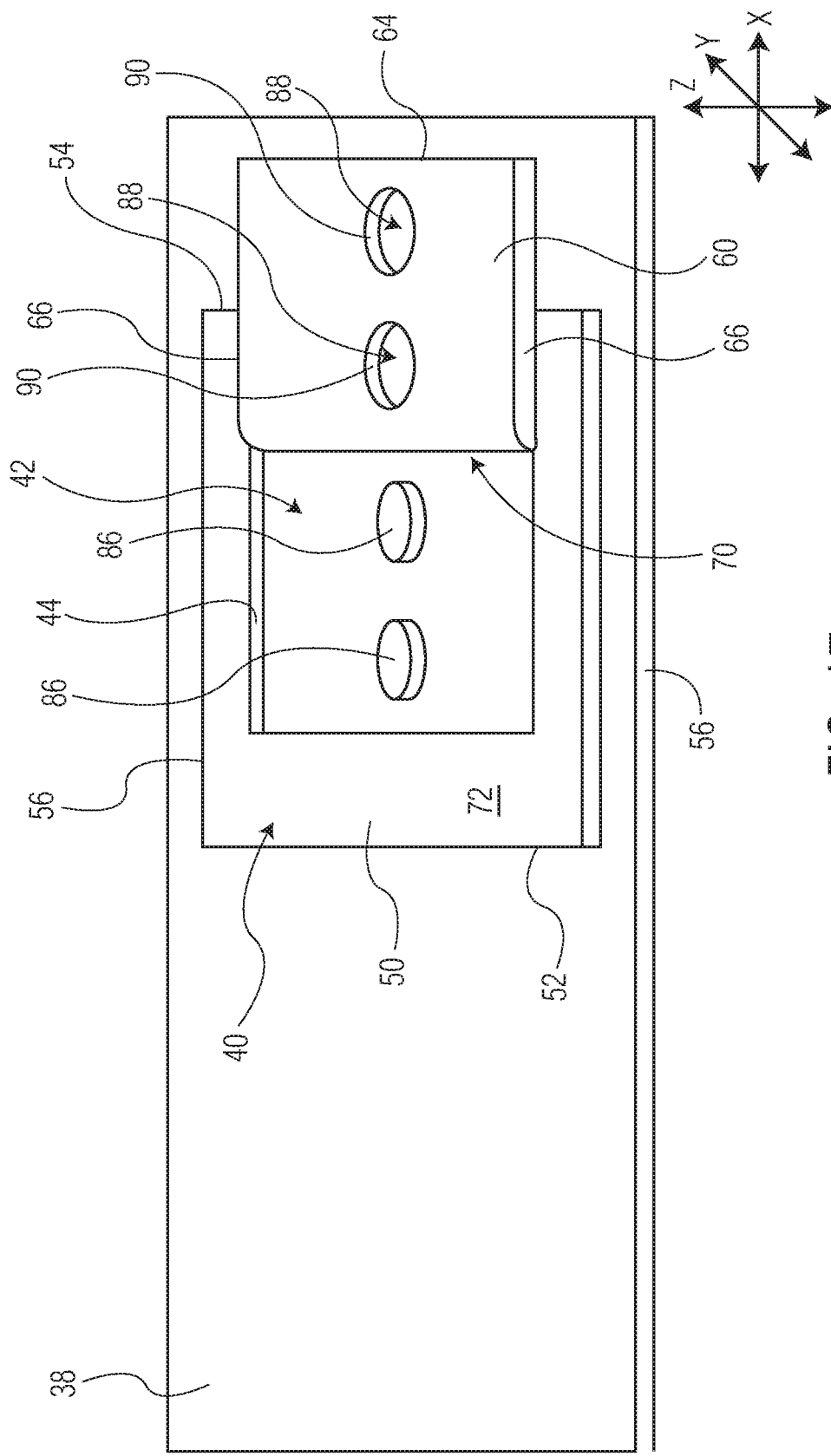
FIG. 17 is a perspective view of an exemplary embodiment of an exudate management layer in fluid communication with an absorbent core.

Referring to FIG. 17, in various embodiments, the second component 60 of the exudate management layer 40 can have at least one opening 88 which can be any suitable shape, such as, but not limited to, ovular, circular, rectangular, square, elliptical, hourglass, triangle, etc. In various embodiments, the shape of the opening 88 can include a shape of a physical object, such as, for example, the outer shape of a leaf, an animal, a star, a heart, a tear drop, a moon, or an abstract configuration. In various embodiments, the opening 88 can be elongate and can be oriented in the longitudinal direction (X) of the absorbent article 10. The opening 88 can be bounded by a perimeter 90 which can form an inner border or inner edge of the second component 60. The opening 88 in the second component 60 can pass through the second component 60 from the body facing surface of the second component 60 to the garment facing surface of the second component 60. In the event of body exudate coming into the location of the opening 88 in the second component, the opening 88 can form a cup or well-like structure for holding body exudate and preventing its leakage away from a region of the absorbent article 10 and towards the edges of the absorbent article 10. The opening 88 can be located at various positions of the second component 60. In various embodiments, the second component 60 can have more than one opening 88 and the plurality of openings 88 can be arranged in the second component 60 in any manner deemed suitable. In various embodiments, the opening 88 can be formed by cutting, punching, or otherwise separating a first portion of the material forming the second component 60 from a second portion of material forming the second component 60. The second portion of material forming the second component 60 is that portion of material which remains as the second component 60 of the exudate management layer 40 and is connected to the first component 50 via the primary fold 70. In various embodiments, the first portion of the material which has been cut, punched, or otherwise separated from the second portion of material forming the second component 60 can be discarded. In various embodiments, the first portion of the material which has been cut, punched, or otherwise separated from the second portion of material forming the second component 60 can be bonded to the absorbent core 38 and can form projection(s) 86 extending upward, in the depth direction (Z) from the body facing surface of the absorbent core 38. The material forming the projection(s) 86 can be bonded to the absorbent core 38 prior to or after the cutting, punching, or otherwise separating the first portion of material forming the second component 60 from the second portion of material forming the second component 60.

Figure 18:
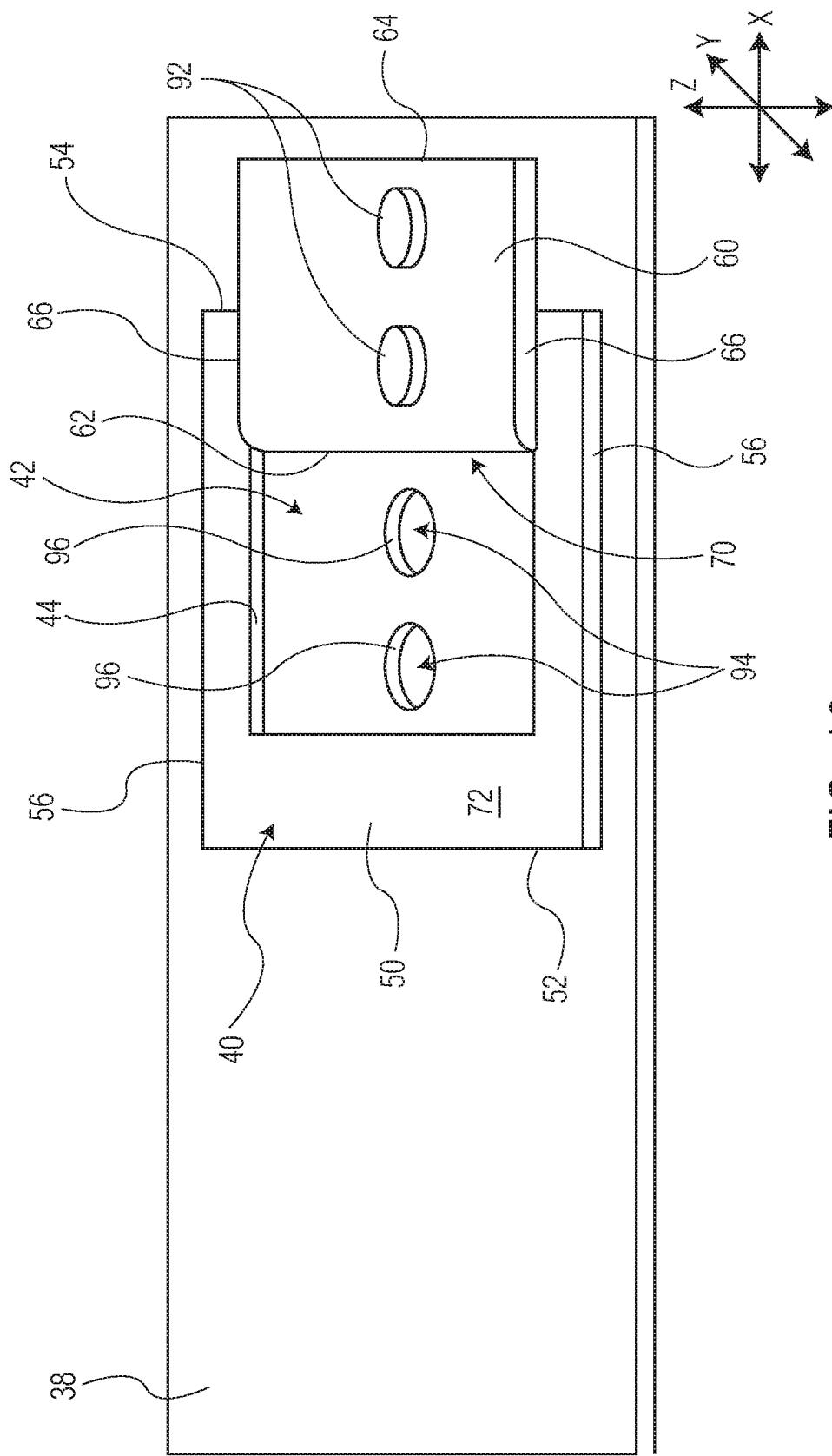
FIG. 18 is a perspective view of an exemplary embodiment of an exudate management layer in fluid communication with an absorbent core.

Referring to FIG. 18, in various embodiments, the absorbent core 38 can have at least one opening 94 which can be any suitable shape, such as, but not limited to, ovular, circular, rectangular, square, elliptical, hourglass, triangle, etc. In various embodiments, the shape of the opening 94 can include a shape of a physical object, such as, for example, the outer shape of a leaf, an animal, a star, a heart, a tear drop, a moon, or an abstract configuration. In various embodiments, the opening 94 can be elongate and can be oriented in the longitudinal direction (X) of the absorbent article 10. The opening 94 can be bounded by a perimeter 96 which can form an inner border or inner edge of the absorbent core 38. The opening 94 in the absorbent core 38 passes through the absorbent core 38 from the body facing surface of the absorbent core 38 to the garment facing surface of the absorbent core 38. In the event of body exudate coming into the location of the opening 94 in the absorbent core 38, the opening 94 can form a cup or well-like structure for holding the body exudate and preventing its leakage away from a region of the absorbent article 10 and towards the edges of the absorbent article 10. The opening 94 can be located at various positions of the absorbent core 38 and within the region of the absorbent core 38 visible through the opening 42 of the exudate management layer 40. In various embodiments, the absorbent core 38 can have more than one opening 94 and the plurality of openings 94 can be arranged in the absorbent core 38 in any manner deemed suitable. The opening 94 in the absorbent core 38 can be formed by cutting, punching, or otherwise separating a first portion of material forming the absorbent core 38 from a second portion of material forming the absorbent core 38. The second portion of material forming the absorbent core 38 is that portion of material which remains as the absorbent core 38 of the absorbent article 10. In various embodiments, the first portion of the material which has been cut, punched, or otherwise separated from the second portion of material forming the absorbent core 38 can be discarded. In various embodiments, the first portion of the material which has been cut, punched, or otherwise separated from the second portion of material forming the absorbent core 38 can be bonded to the second component 60 of the exudate management layer 40 and can form projection(s) 92 extending upward, in the depth direction (Z) from the body facing surface of the second component 60. The material forming the projection(s) 92 can be bonded to the second component 60 prior to or after the cutting, punching, or otherwise separating of the second component 60 from the first component 50 of the exudate management layer 40.

Figure 19:
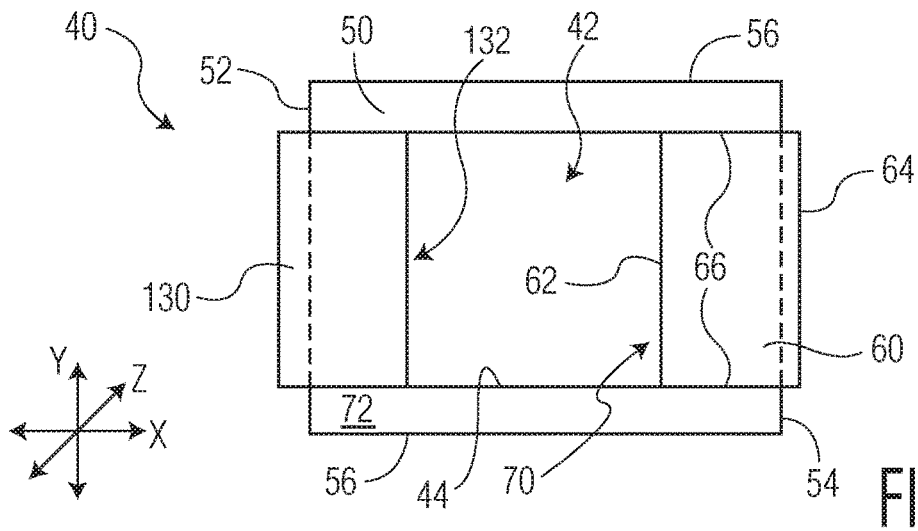
FIG. 19 is a top down view of an exemplary embodiment of an exudate management layer.
Figure 20:
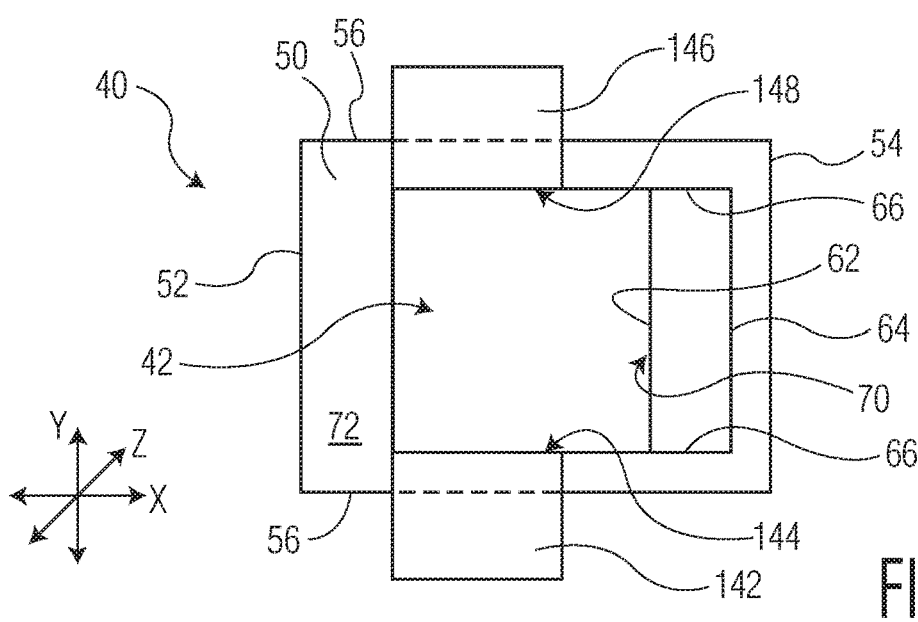
FIG. 20 is a top down view of an exemplary embodiment of an exudate management layer.
Figure 21:
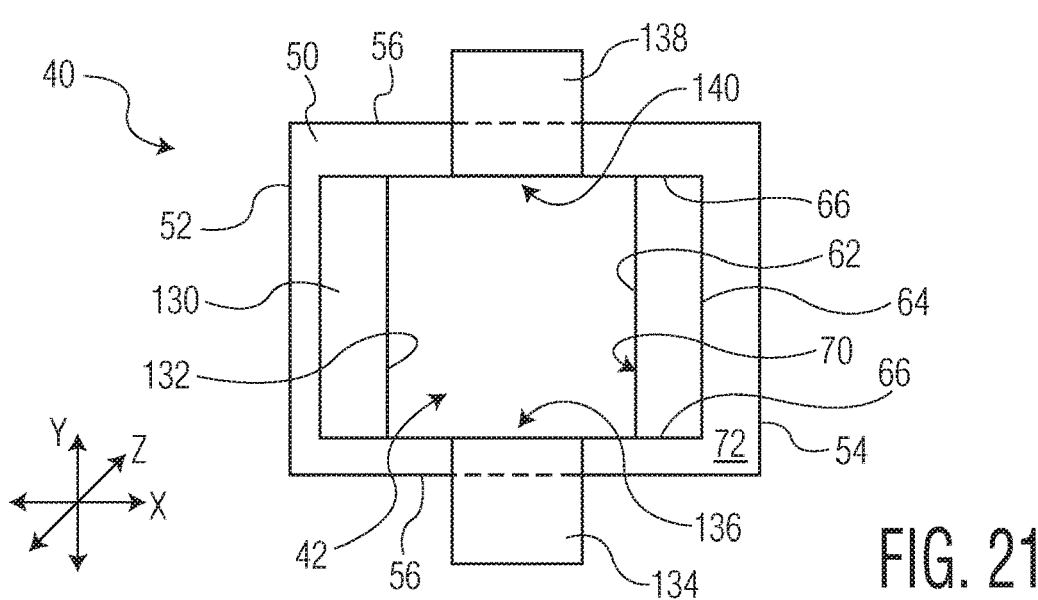
FIG. 21 is a top down view of an exemplary embodiment of an exudate management layer.

As described herein, the exudate management layer 40 has a first component 50 which at least partially defines an opening 42 and a second component 60 connected to the first component 50 via a primary fold 70. In various embodiments, the exudate management layer 40 can have a third component connected to the first component 50 via a third component primary fold. In various embodiments, the exudate management layer 40 can have a third component and a fourth component wherein each of the third component and fourth component is connected to the first component 50 via their own component primary folds. In various embodiments, the exudate management layer 40 can have a third component, a fourth component, and a fifth component connected to the first component 50 via their own component primary folds. Referring to FIG. 19, FIG. 19 provides an exemplary illustration of an exudate management layer 40 having a first component 50, a second component 60 connected to the first component 50 via primary fold 70, a third component 130 connected to the first component 50 via third component primary fold 132, and an opening 42 defined by the first component 50, the primary fold 70, and the third component primary fold 132. The second component 60 can extend from the primary fold 70 in the longitudinal direction (X) of the absorbent article 10 in a direction towards the posterior region 14 of the absorbent article 10 and the third component 130 can extend from the third component primary fold 132 in the longitudinal direction (X) of the absorbent article 10 in a direction towards the anterior region 12 of the absorbent article 10. FIG. 20 provides an exemplary illustration of an exudate management layer 40 having a first component 50, a second component 60 connected to the first component 50 via primary fold 70, a third component 142 connected to the first component via third component primary fold 144, a fourth component 146 connected to the first component 50 via fourth component primary fold 148, and an opening 42 defined by the first component 50, the primary fold 70, the third component primary fold 144, and the fourth component primary fold 148. In the embodiments illustrated in FIG. 20, the second component 60 can extend from the primary fold 70 in the longitudinal direction (X) of the absorbent article 10 in a direction towards the posterior region 14 of the absorbent article 10, the third component 142 can extend from the third component primary fold 144 in the transverse direction (Y) of the absorbent article 10, and the fourth component 146 can extend from the fourth component primary fold 148 in the transverse direction (Y) of the absorbent article 10. FIG. 21 provides an exemplary illustration of an exudate management layer 40 having a first component 50, a second component 60 connected to the first component 50 via primary fold 70, a third component 130 connected to the first component 50 via third component primary fold 132, a fourth component 134 connected to the first component 50 via fourth component primary fold 136, a fifth component 138 connected to the first component 50 via fifth component primary fold 140, and an opening 42 defined by the first component 50, the primary fold 70, the third component primary fold 132, the fourth component primary fold 136, and the fifth component primary fold 140. In the embodiment illustrated in FIG. 21, the second component 60 can extend from the primary fold 70 in the longitudinal direction (X) of the absorbent article 10 in a direction towards the posterior region 14 of the absorbent article 10, the third component 130 can extend from the third component primary fold 132 in the longitudinal direction (X) of the absorbent article 10 in a direction towards the anterior region 12 of the absorbent article 10, the fourth component 134 can extend from the fourth component primary fold 136 in the transverse direction (Y) of the absorbent article 10, and the fifth component 138 can extend from the fifth component primary fold 140 in the transverse direction (Y) of the absorbent article 10.

Figure 22:
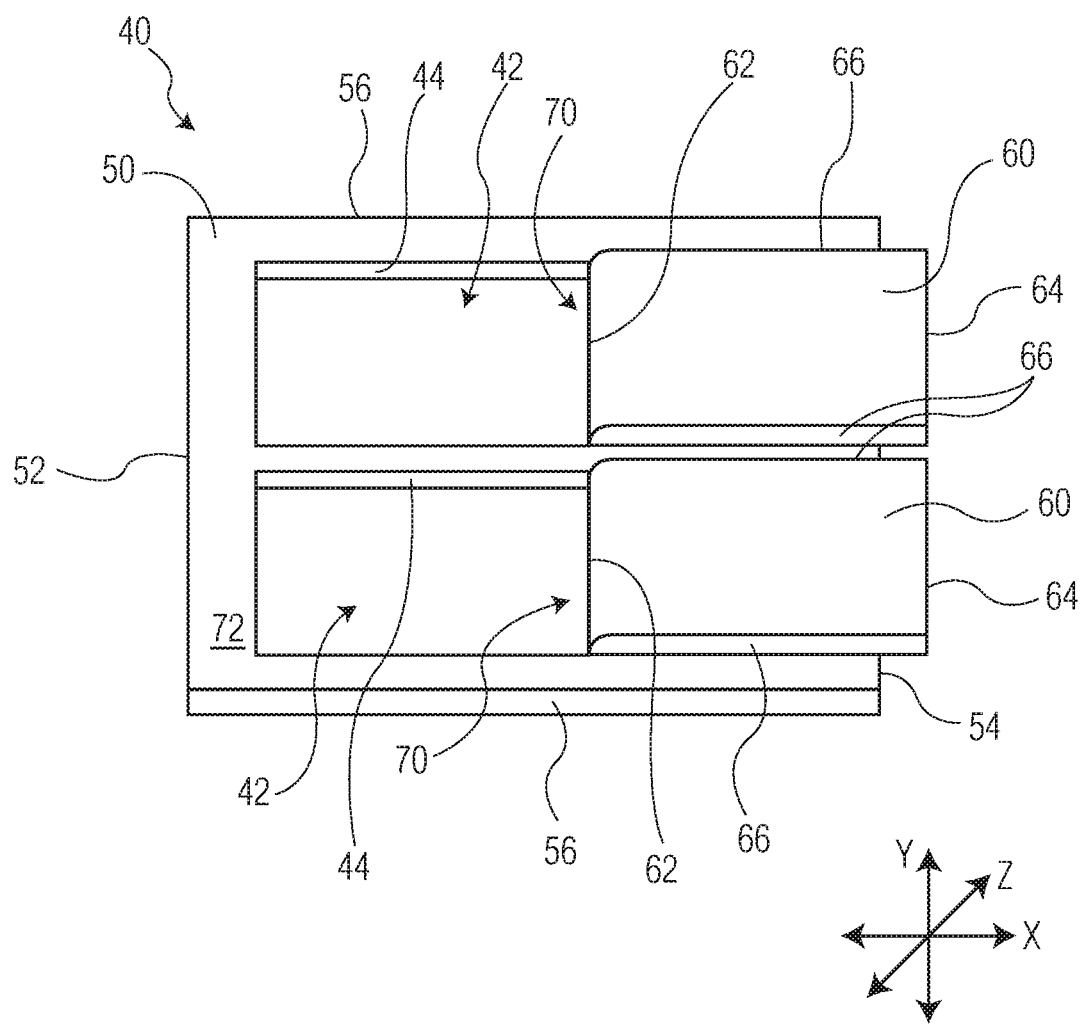
FIG. 22 is a perspective view of an exemplary embodiment of an exudate management layer.

In various embodiments, such as, for example illustrated in FIG. 22, the exudate management layer 40 can have at least two openings 42 for the capture and containment of fecal material. In various embodiments, the exudate management layer 40 can have at least 1, 2, 3, 4, or 5 openings 42. Each of the openings 42 can have any shape deemed suitable such as, for example, described herein. Each of the openings 42 can be bounded at least partially by a perimeter 44 and at least partially by a primary fold 70 of their respective second component 60. The plurality of openings 42 can be arranged in the exudate management layer 40 in any manner deemed suitable. In various embodiments, at least one of the plurality of openings 42 can be symmetrical about the longitudinal centerline 18. In various embodiments, none of the openings 42 is symmetrical about the longitudinal centerline 18. In various embodiments, one of the plurality of openings 42 can be positioned that that a portion of the opening 42 crosses over the transverse centerline 80. In various embodiments, each of the openings 42 is positioned between the transverse centerline 80 and the second transverse direction end edge 22 of the absorbent article 10.

Containment Flaps:

In various embodiments, the absorbent article can have containment flaps. FIGS. 2, 3, 5, and 7 provide illustrations of exemplary embodiments of an absorbent article 10 with containment flaps, 210 and 212. In various embodiments, containment flaps, 210 and 212, can be secured to the topsheet layer 30 of the absorbent article 10 in a generally parallel, spaced relation with each other laterally inward of the longitudinal direction side edges 24 to provide a barrier against the flow of body exudates in the transverse direction (Y) of the absorbent article 10. In various embodiments, the containment flaps, 210 and 212, can extend longitudinally from the anterior region 12 of the absorbent article 10, through the central region 16 to the posterior region 14 of the absorbent article 10.

The containment flaps, 210 and 212, can be constructed of a fibrous material which can be similar to the material forming the topsheet layer 30. Other conventional material, such as polymer films, can also be employed. Each containment flap, 210 and 212, can have a moveable distal end 214 which can include flap elastics 216. Suitable elastic materials for the flap elastics 216 can include sheets, strands or ribbons of natural rubber, synthetic rubber, or thermoplastic elastomeric materials. In various embodiments, the flap elastics 216 can have two strands of elastomeric material extending longitudinally along the distal ends 214 of the containment flaps, 210 and 212, in generally parallel, spaced relation with each other. The elastic strands can be within the containment flaps, 210 and 212, while in an elastically contractible condition such that contraction of the strands gathers and shortens the distal ends 214 of the containment flaps, 210 and 212. As a result, the elastic strands can bias the distal ends 214 of each containment flap, 210 and 212, toward a position spaced from the proximal end of the containment flaps, 210 and 212, so that the containment flaps, 210 and 212, can extend away from the topsheet layer 30 in a generally upright orientation of the containment flaps, 210 and 212, especially in the central region 16 of the absorbent article 10, when the absorbent article 10 is fitted on the wearer. The distal end 214 of the containment flaps, 210 and 212, can be connected to the flap elastics 216 by partially doubling the containment flap, 210 and 212, material back upon itself by an amount which can be sufficient to enclose the flap elastics 216. It is to be understood, however, that the containment flaps, 210 and 212, can have any number of strands of elastomeric material and may also be omitted from the absorbent article 10 without departing from the scope of this disclosure.

In various embodiments, such as, for example, illustrated in FIGS. 3, 4A, 4B, 5, 6A, and 6B, the absorbent article 10 can have an exudate management layer 40 positioned on the body facing surface 32 of the topsheet layer 30. In various embodiments, the exudate management layer 40 can be sized and positioned such that the longitudinal direction side edges 56 of the first component 50 of the exudate management layer 40 are located underneath the containment flaps, 210 and 212, of the absorbent article 10. In various embodiments, portions of the first component 50 such as, for example, at least portions of the longitudinal direction side edges 56, can be bonded to the containment flaps, 210 and 212. In such embodiments, when the containment flaps, 210 and 212, extend away from the topsheet layer 30 in a generally upright orientation of the containment flaps, 210 and 212, the exudate management layer 40 can be elevated away from the topsheet layer 30 and provide a close to body fit of the absorbent article 10 to the body of the wearer. In various embodiments, the transverse direction end edges, 52 ad 54, of the first component 50 can be bonded to the topsheet layer 30 so as to create a pocket for the body exudate when the exudate management layer 40 is elevated away from the topsheet layer 30 as the containment flaps, 210 and 212, are in a generally upright orientation during usage of the absorbent article 10.

Acquisition Layer:

In various embodiments, the absorbent article 10 can have an acquisition layer. The acquisition layer can help decelerate and diffuse surges or gushes of liquid body exudates penetrating the topsheet layer 30. In various embodiments, the exudate management layer 40 can be positioned on the body facing surface 32 of the topsheet layer 30 and the acquisition layer can be positioned between the topsheet layer 30 and the absorbent core 38. In various embodiments, the acquisition layer can be positioned on the body facing surface 32 of the topsheet layer 30 and the exudate management layer 40 can be positioned on the body facing surface of the acquisition layer. In various embodiments, an absorbent article 10 can have an exudate management layer 40 positioned between the topsheet layer 30 and the absorbent core 38 with an acquisition layer positioned between the exudate management layer 40 and the absorbent core 38.

The acquisition layer may have any longitudinal length dimension as deemed suitable. In various embodiments, the longitudinal length of the acquisition layer can be the same as the longitudinal length of the absorbent core 38. In various embodiments, the longitudinal length of the acquisition layer can be shorter than the longitudinal length of the absorbent core 38. In such embodiments, the acquisition layer may be positioned at any desired location along the longitudinal length of the absorbent core 38.

In an embodiment, the acquisition layer can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer can be formed from a material that is substantially hydrophobic, such as a nonwoven web composed of polypropylene, polyethylene, polyester, and the like, and combinations thereof. In various embodiments, the acquisition layer can include conjugate, biconstituent, and/or homopolymer fibers of staple or other lengths and mixtures of such fibers with other types of fibers. In various embodiments, the acquisition layer can have fibers which can have a denier of greater than about 5. In various embodiments, the acquisition layer can have fibers which can have a denier of less than about 5.

In various embodiments, the acquisition layer can be a bonded carded web or an airlaid web. In various embodiments, the bonded carded web may be, for example, a powder bonded carded web, an infrared bonded carded web, or a through air bonded carded web.

In various embodiments, the basis weight of the acquisition layer can be at least about 10 or 20 gsm. In various embodiments, the basis weight of the acquisition layer can be from about 10, 20, 30, 40, 50 or 60 gsm to about 65, 70, 75, 80, 85, 90, 100, 110, 120, or 130 gsm. In various embodiments, the basis weight of the acquisition layer can be less than about 130, 120, 110, 100, 90, 85, 80, 75, 70, 65, 60 or 50 gsm.

Figure 23:
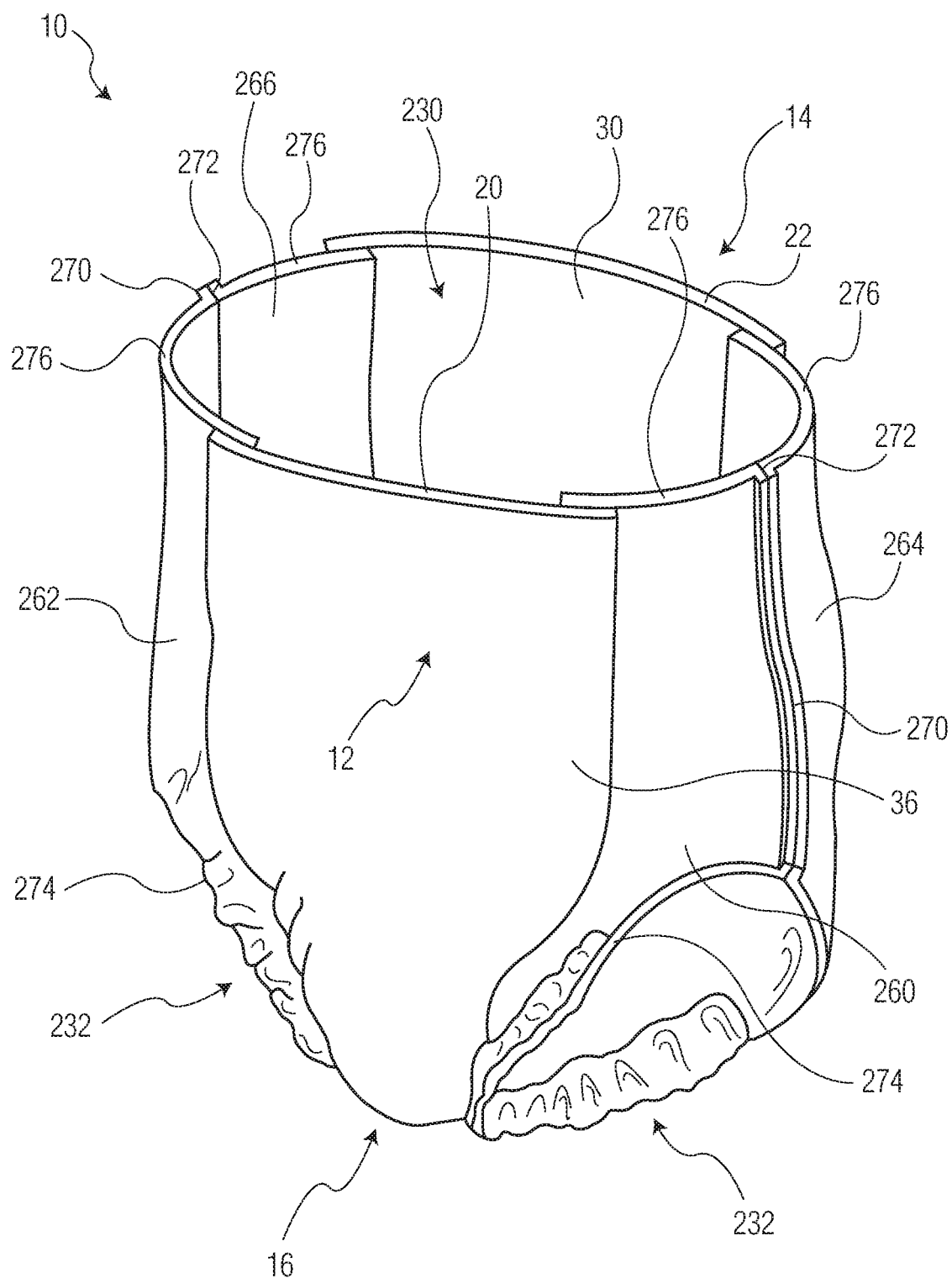
FIG. 23 is a perspective view of an exemplary embodiment of an absorbent article.

Side Panels:

FIG. 23 provides an illustration of an exemplary embodiment of a perspective view of an absorbent article 10 such as a pant, such as, for example, a training pant, youth pant, diaper pant, or an adult incontinence pant. In an embodiment in which the absorbent article 10 can be a training pant, youth pant, diaper pant, or adult incontinence pant, the absorbent article 10 may have front side panels, 260 and 262, and rear side panels, 264 and 266. FIG. 23 provides a non-limiting illustration of an absorbent article 10 that can have side panels, such as front side panels, 260 and 262, and rear side panels, 264 and 266. The front side panels 260 and 262 and the rear side panels 264 and 266 of the absorbent article 10 can be bonded to the absorbent article 10 in the respective anterior and posterior regions, 12 and 14, and can extend outwardly beyond the longitudinal side edges 24 of the absorbent article 10. In an example, the front side panels, 260 and 262, can be bonded to the liquid impermeable layer 36 such as being bonded thereto by adhesive, by pressure bonding, by thermal bonding or by ultrasonic bonding. The back side panels, 264 and 266, may be secured to the liquid impermeable layer 36 in substantially the same manner as the front side panels, 260 and 262. Alternatively, the front side panels, 260 and 262, and the back side panels, 264 and 266, may be formed integrally with the absorbent article 10, such as by being formed integrally with the liquid impermeable layer 36, the topsheet layer 30 or other layers of the absorbent article 10.

For improved fit and appearance, the front side panels, 260 and 262, and the back side panels, 264 and 266, can suitably have an average length measured parallel to the longitudinal centerline 18 of the absorbent article 10 that is about 20 percent or greater, and more suitably about 25 percent or greater, of the overall length of the absorbent article 10, also measured parallel to the longitudinal centerline 18. For example, absorbent articles 10 having an overall length of about 54 centimeters, the front side panels, 260 and 262, and the back side panels, 264 and 266, suitably have an average length of about 10 centimeters or greater, and more suitably have an average length of about 15 centimeters. Each of the front side panels, 260 and 262, and back side panels, 264 and 266, can be constructed of one or more individual, distinct pieces of material. For example, each front side panel, 260 and 262, and back side panel, 264 and 266, can include first and second side panel portions (not shown) joined at a seam (not shown), with at least one of the portions including an elastomeric material. Alternatively, each individual front side panel, 260 and 262, and back side panel, 264 and 266, can be constructed of a single piece of material folded over upon itself along an intermediate fold line (not shown).

The front side panels, 260 and 262, and back side panels, 264 and 266, can each have an outer edge 270 spaced laterally from the engagement seam 272, a leg end edge 274 disposed toward the longitudinal center of the absorbent article 10, and a waist end edge 276 disposed toward a longitudinal end of the absorbent article 10. The leg end edge 274 and waist end edge 276 can extend from the longitudinal side edges 24 of the absorbent article 10 to the outer edges 270. The leg end edges 274 of the front side panels, 260 and 262, and back side panels, 264 and 266, can form part of the longitudinal side edges 24 of the absorbent article 10. The leg end edges 274 of the illustrated absorbent article 10 can be curved and/or angled relative to the transverse centerline 80 to provide a better fit around the wearer's legs. However, it is understood that only one of the leg end edges 274 can be curved or angled, such as the leg end edge 274 of the posterior region 14, or neither of the leg end edges 274 can be curved or angled, without departing from the scope of this disclosure. The waist end edges 276 can be parallel to the transverse centerline 80. The waist end edges 276 of the front side panels, 260 and 262, can form part of the first transverse direction end edge 20 of the absorbent article 10, and the waist end edges 276 of the back side panels, 264 and 266, can form part of the second transverse direction end edge 22 of the absorbent article 10.

The front side panels, 260 and 262, and back side panels, 264 and 266, can include an elastic material capable of stretching laterally. Suitable elastic materials, as well as one described process for incorporating elastic front side panels, 260 and 262, and back side panels, 264 and 266, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987, in the names of Taylor et al., and PCT Application WO 01/88245 in the name of Welch et al., all of which are incorporated herein by reference. Other suitable materials are described in U.S. patent application Ser. Nos. 12/649,508 to Welch et al. and 12/023,447 to Lake et al., all of which are incorporated herein by reference. Alternatively, the front side panels, 260 and 262, and back side panels, 264 and 266, may include other woven or non-woven materials, such as those described above as being suitable for the liquid impermeable layer 36.

Method to Determine Percent Open Area:

The percentage of open area can be determined by using the image analysis measurement method described herein. In this context, the open area is considered the regions within a material where light transmitted from a light source passes directly thru those regions unhindered in the material of interest. Generally, the image analysis method determines a numeric value of percent open area for a material via specific image analysis measurement parameters such as area. The percent open area method is performed using conventional optical image analysis techniques to detect open area regions in both land areas and projections separately and then calculating their percentages in each. To separate land areas and projections for subsequent detection and measurement, incident lighting is used along with image processing steps. An image analysis system, controlled by an algorithm, performs detection, image processing and measurement and also transmits data digitally to a spreadsheet database. The resulting measurement data are used to determine the percent open area of materials possessing land areas and projections.

Figure 24:
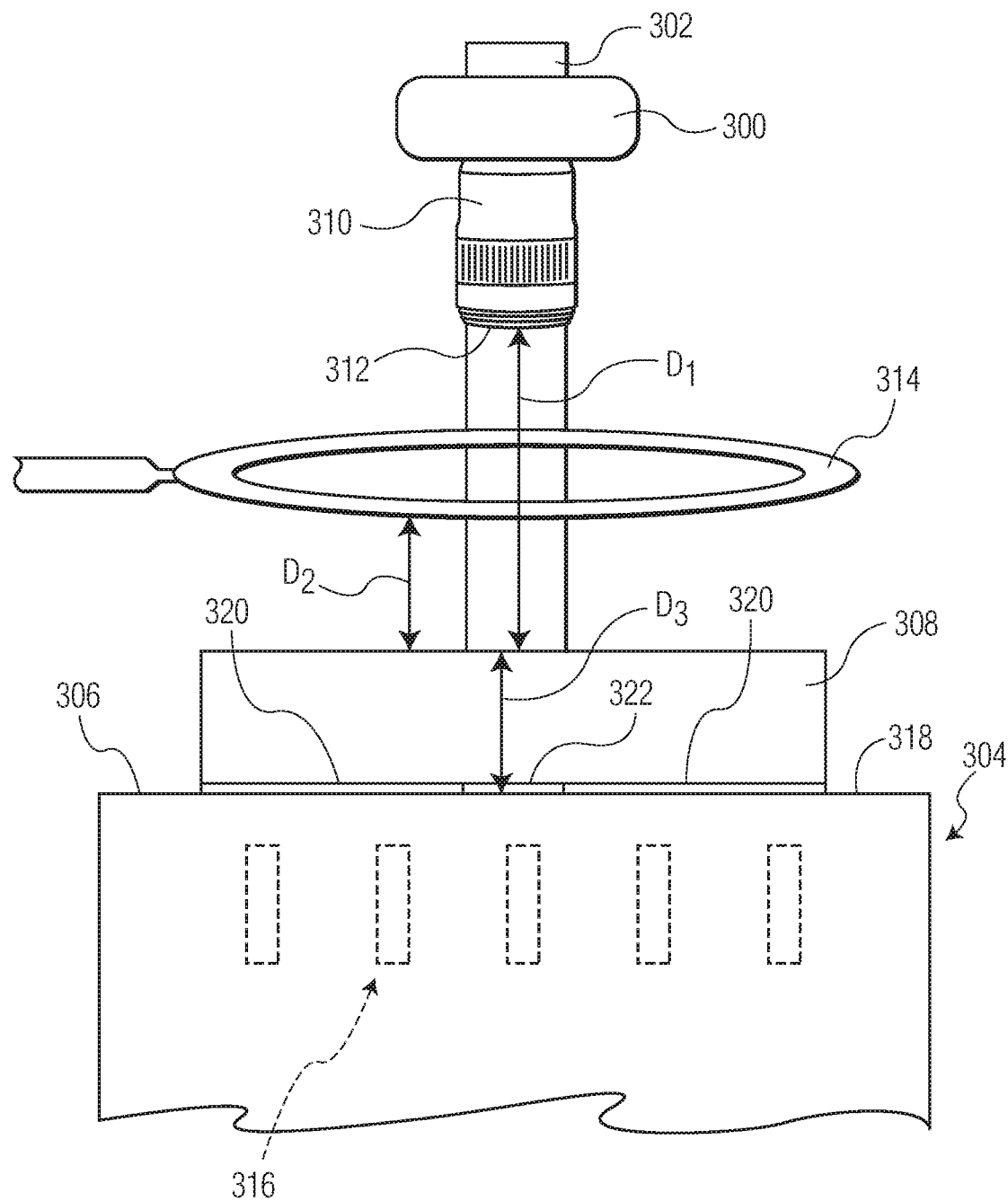
FIG. 24 is a perspective view of an exemplary illustration of a set-up of an imaging system used for determining the percent open area of a fluid entangled laminate web.

The method for determining the percent open area in both land areas and projections of a given material includes the step of acquiring two separate digital images of the material. An exemplary setup for acquiring the image is representatively illustrated in FIG. 24. Specifically, a CCD video camera 300 (e.g., a Leica DFC 310 FX video camera operated in gray scale mode and available from Leica Microsystems of Heerbrugg, Switzerland) is mounted on a standard support 302 such as a Polaroid MP-4 Land Camera standard support or equivalent available from Polaroid Resource Center in Cambridge, Miss. The standard support 302 is attached to a macro-viewer 304 such as a KREONITE macro-viewer available from Dunning Photo Equipment, Inc., having an office in Bixby, Okla. An auto stage 308 is placed on the upper surface 306 of the macro-viewer 304. The auto stage 308 is used to automatically move the position of a given material for viewing by the camera 300. A suitable auto stage is Model H112, available from Prior Scientific Inc., having an office in Rockland, Mass.

The material possessing land areas and projections is placed on the auto stage 308 under the optical axis of a 60 mm Nikon AF Micro Nikkor lens 310 with an f-stop setting of 4. The Nikon lens 310 is attached to the Leica DFC 310 FX camera 300 using a c-mount adaptor. The distance D1 from the front face 312 of the Nikon lens 310 to the material is 21 cm. The material is laid flat on the auto stage 308 and any wrinkles removed by gentle stretching and/or fastening it to the auto stage 308 surface using transparent adhesive tape at its outer edges. The material is oriented so the machine-direction (MD) runs in the horizontal direction of the resulting image. The material surface is illuminated with incident fluorescent lighting provided by a 16 inch diameter, 40 watt, GE Circline fluorescent lamp 314. The lamp 314 is contained in a fixture that is positioned so it is centered over the material and under the video camera above and is a distance D2 of 3 inches above the material surface. The illumination level of the lamp 314 is controlled with a Variable Auto-transformer, type 3PN1010, available from Staco Energy Products Co. having an office in Dayton, Ohio. Transmitted light is also provided to the material from beneath the auto stage 308 by a bank of five 20 watt fluorescent lights 316 covered with a diffusing plate 318. The diffusing plate 318 is inset into, and forms a portion of, the upper surface 306 of the macro-viewer 304. The diffusing plate 318 is overlaid with a black mask 320 possessing a 3-inch by 3-inch opening 322. The opening 322 is positioned so that it is centered under the optical axis of the Leica camera and lens system. The distance D3 from the opening 322 to the surface of the auto stage 308 is approximately 17 cm. The illumination level of the fluorescent light bank 316 is also controlled with a separate Variable Auto-transformer.

The image analysis software platform used to perform the percent open area measurements is a QWIN Pro (Version 3.5.1) available from Leica Microsystems, having an office in Heerbrugg, Switzerland. The system and images are also calibrated using the QWIN software and a standard ruler with metric markings at least as small as one millimeter. The calibration is performed in the horizontal dimension of the video camera image. Units of millimeters per pixel are used for the calibration.

The method for determining the percent open area of a given material includes the step of performing several area measurements from both incident and transmitted light images. Specifically, an image analysis algorithm is used to acquire and process images as well as perform measurements using Quantimet User Interactive Programming System (QUIPS) language. The image analysis algorithm is reproduced below.

```
NAME = % Open Area – Land vs Projection Regions–1
PURPOSE = Measures % open area on 'land' and 'projection' regions via 'sandwich' lighting technique
    DEFINE VARIABLES & OPEN FILES
    Open File ( C:\Data\39291\% Open Area\data.xls, channel #1 )
    MFLDIMAGE = 2
    TOTCOUNT = 0
    TOTFIELDS = 0
    SAMPLE ID AND SET UP
    Configure ( Image Store 1392 × 1040, Grey Images 81, Binaries 24 )
    Enter Results Header
    File Results Header ( channel #1 )
    File Line ( channel #1 )
    Image Setup DC Twain [PAUSE] ( Camera 1, AutoExposure Off, Gain 0.00,
      ExposureTime 34.23 msec, Brightness 0, Lamp 38.83 )
    Measure frame ( x 31, y 61, Width 1330, Height 978 )
    Image frame ( x 0, y 0, Width 1392, Height 1040 )
    -- Calvalue = 0.0231 mm/px
    CALVALUE = 0.0231
    Calibrate ( CALVALUE CALUNITS$ per pixel )
    Clear Accepts
    For ( SAMPLE = 1 to 1, step 1 )
       Clear Accepts
       File ( "Field No.", channel #1, field width: 9, left justified )
       File ( "Land Area", channel #1, field width: 9, left justified )
       File ( "Land Open Area", channel #1, field width: 13, left justified )
       File ( "%Open Land Area", channel #1, field width: 15, left justified )
       File ( "Proj. Area", channel #1, field width: 9, left justified )
       File ( "Proj. Open Area", channel #1, field width: 13, left justified )
       File ( "% Open Proj. Area", channel #1, field width: 15, left justified )
       File ( "Total % Open Area", channel #1, field width: 14, left justified )
       File Line ( channel #1 )
       Stage ( Define Origin )
       Stage ( Scan Pattern, 5 × 1 fields, size 82500.000000 × 82500.000000 )
       IMAGE ACQUISITION I - Projection isolation
       For ( FIELD = 1 to 5, step 1 )
          Display ( Image0 (on), frames (on,on), planes (off,off,off,off,off,off), lut 0, x 0, y 0, z
            1, Reduction off )
          PauseText ( "Ensure incident lighting is correct (WL = 0.88 – 0.94) and acquire
              image." )
          Image Setup DC Twain [PAUSE] ( Camera 1, AutoExposure Off, Gain 0.00,
              ExposureTime 34.23 msec, Brightness 0, Lamp 38.83 )
          Acquire ( into Image0 )
          DETECT - Projections only
          PauseText ( "Ensure that threshold is set at least to the right of the left gray-level
              histogram peak which corresponds to the 'land' region." )
          Detect [PAUSE] ( whiter than 127, from Image0 into Binary0 delineated )
       BINARY IMAGE PROCESSING
       Binary Amend (Close from Binary0 to Binary1, cycles 10, operator Disc, edge erode on)
       Binary Identify ( Fill Holes from Binary1 to Binary1 )
       Binary Amend (Open from Binary1 to Binary2, cycles 20, operator Disc, edge erode on)
       Binary Amend (Close from Binary2 to Binary3, cycles 8, operator Disc, edge erode on )
       PauseText ("Toggle <control> and <b> keys to check bump detection and correct if
            necessary." )
        Binary Edit [PAUSE] ( Draw from Binary3 to Binary3, nib Fill, width 2 )
        Binary Logical ( copy Binary3, inverted to Binary4 )
       IMAGE ACQUISITION 2 - % Open Area
       Display ( Image0 (on), frames (on,on), planes (off,off,off,off,off,off), lut 0, x 0, y 0, z
            1, Reduction off )
       PauseText ( "Turn off incident light & ensure transmitted lighting is correct (WL =
          0.97) and acquire image." )
         Image Setup DC Twain [PAUSE] ( Camera 1, AutoExposure Off, Gain 0.00,
             ExposureTime 34.23 msec, Brightness 0, Lamp 38.83 )
         Acquire ( into Image0 )
         DETECT - Open areas only
         Detect ( whiter than 210, from Image0 into Binary10 delineated )
         BINARY IMAGE PROCESSING
         Binary Logical ( C = A AND B : C Binary11, A Binary3, B Binary10 )
         Binary Logical ( C = A AND B : C Binary12, A Binary4, B Binary10 )
```

```
               MEASURE AREAS - Land, projections, open area within each
               -- Land Area
               MFLDIMAGE = 4
               Measure field ( plane MFLDIMAGE, into FLDRESULTS(1), statistics into
                   FLDSTATS(7,1) ) Selected parameters: Area
               LANDAREA = FLDRESULTS(1)
               -- Projection Area
               MFLDIMAGE = 3
               Measure field ( plane MFLDIMAGE, into FLDRESULTS(1), statistics into
                   FLDSTATS(7,1) ) Selected parameters: Area
               BUMPAREA = FLDRESULTS(1)
               -- Open Projection area
               MFLDIMAGE = 11
               Measure field ( plane MFLDIMAGE, into FLDRESULTS(1), statistics into
                   FLDSTATS(7,1) ) Selected parameters: Area
               APBUMPAREA = FLDRESULTS(1)
               -- Open land area
               MFLDIMAGE = 12
               Measure field ( plane MFLDIMAGE, into FLDRESULTS(1), statistics into
                   FLDSTATS(7,1) ) Selected parameters: Area
               APLANDAREA = FLDRESULTS(1)
               -- Total % open area
               MFLDIMAGE = 10
               Measure field ( plane MFLDIMAGE, into FLDRESULTS(1), statistics into
                   FLDSTATS(7,1) ) Selected parameters: Area %
               TOTPERCAPAREA = FLDRESULTS(1)
               CALCULATE AND OUTPUT AREAS
               PERCAPLANDAREA = APLANDAREA/LANDAREA*100
               PERCAPBUMPAREA = APBUMPAREA/BUMPAREA*100
               File ( FIELD, channel #1, 0 digits after '.' )
               File ( LANDAREA, channel #1, 2 digits after '.' )
               File ( APLANDAREA, channel #1, 2 digits after '.' )
               File ( PERCAPLANDAREA, channel #1, 1 digit after '.' )
               File ( BUMPAREA, channel #1, 2 digits after '.' )
               File ( APBUMPAREA, channel #1, 4 digits after '.' )
               File ( PERCAPBUMPAREA, channel #1, 5 digits after '.' )
               File ( TOTPERCAPAREA, channel #1, 2 digits after '.' )
               File Line ( channel #1 )
               Stage ( Step, Wait until stopped + 1100 msecs )
            Next (FIELD)
            PauseText ( "If no more samples, enter '0.'" )
            Input ( FINISH )
            If ( FINISH=0 )
               Goto OUTPUT
            Endif
            PauseText ( "Place the next replicate specimen on the auto-stage, turn on incident light
               and turn-off and/or block sub-stage lighting." )
            Image Setup DC Twain [PAUSE] ( Camera 1, AutoExposure Off, Gain 0.00,
               ExposureTime 34.23 msec, Brightness 0, Lamp 38.83 )
               File Line (channel #1)
         Next ( SAMPLE )
         OUTPUT:
         Close File ( channel #1 )
      END
```

The QUIPS algorithm is executed using the QWIN Pro software platform. The analyst is initially prompted to enter the material set information which is sent to the EXCEL file.

The analyst is next prompted by a live image set up window on the computer monitor screen to place a material onto the auto-stage 308. The material should be laid flat and gentle force applied at its edges to remove any macro-wrinkles that may be present. It should also be aligned so that the machine direction runs horizontally in the image. At this time, the Circline fluorescent lamp 314 can be on to assist in positioning the material. Next, the analyst is prompted to adjust the incident Circline fluorescent lamp 314 via the Variable Auto-transformer to a white level reading of approximately 0.9. The sub-stage transmitted light bank 316 should either be turned off at this time or masked using a piece of light-blocking, black construction paper placed over the 3 inch by 3 inch opening 322.

The analyst is now prompted to ensure that the detection threshold is set to the proper level for detection of the projections using the Detection window which is displayed on the computer monitor screen. Typically, the threshold is set using the white mode at a point approximately near the middle of the 8-bit gray-level range (e.g. 127). If necessary, the threshold level can be adjusted up or down so that the resulting detected binary will optimally encompass the projections shown in the acquired image with respect to their boundaries with the surrounding land region.

After the algorithm automatically performs several binary image processing steps on the detected binary of the projections, the analyst will be given an opportunity to re-check projection detection and correct any inaccuracies. The analyst can toggle both the 'control' and 'b' keys simultaneously to re-check projection detection against the underlying acquired gray-scale image. If necessary, the analyst can select from a set of binary editing tools (e.g. draw, reject, etc.) to make any minor adjustments. If care is taken to ensure proper illumination and detection in the previously described steps, little or no correction at this point should be necessary.

Next, the analyst is prompted to turn off the incident Circline fluorescent lamp 314 and either turn on the sub-stage transmitted light bank or remove the light blocking mask. The sub-stage transmitted light bank is adjusted by the Variable Auto-transformer to a white level reading of approximately 0.97. At this point, the image focus can be optimized for the land areas of the material.

The algorithm, after performing additional operations on the resulting separate binary images for projections, land areas and open area, will then automatically perform measurements and output the data into a designated EXCEL spreadsheet file. The following measurement parameter data will be located in the EXCEL file after measurements and data transfer has occurred:

Land Area
Land Open Area
Land % Open Area
Projection Area
Projection Open Area
Projection % Open Area
Total % Open Area Following the transfer of data, the algorithm will direct the auto-stage 308 to move to the next field-of-view and the process of turning on the incident, Circline fluorescent lamp 314 and blocking the transmitted sub-stage lighting bank 316 will begin again. This process will repeat four times so that there will be five sets of data from five separate field-of-view images per single material replicate.

Multiple sampling replicates from a single material can be performed during a single execution of the QUIPS algorithm (Note: The Sample For-Next line in the algorithm needs to be adjusted to reflect the number of material replicate analyses to be performed per material). The final material mean spread value is usually based on an N=5 analysis from five, separate, material subsample replicates. A comparison between different materials can be performed using a Student's T analysis at the 90% confidence level.

Method to Determine Height of Projections Test Method:

The height of the projections can be determined by using the image analysis measurement method described herein. The image analysis method determines a dimensional numeric height value for projections using specific image analysis measurements of both land areas and projections with underlying land regions in a sample and then calculating the projection height alone by difference between the two. The projection height method is performed using conventional optical image analysis techniques to detect cross-sectional regions of both land areas and projection structures and then measure a mean linear height value for each when viewed using a camera with incident lighting. The resulting measurement data are used to compare the projection height characteristics of different types of body-side intake layers.

Prior to performing image analysis measurements, the sample of interest must be prepared in such a way to allow visualization of a representative cross-section that passes thru the center of a projection. Cross-sectioning can be performed by anchoring a representative piece of the sample on at least one of its cross-machine running straight edges on a flat, smooth surface with a strip of tape such as ¾ inch SCOTCH® Magic™ tape produced by 3M. Cross-sectioning is then performed by using a new, previously unused single edge carbon steel blue blade (PAL) and carefully cutting in a direction away from and orthogonal to the anchored edge and thru the centers of at least one projection and preferably more if projections are arranged in rows running in the machine direction. Any remaining rows of projections located behind the cross-sectioned face of projections should be cut away and removed prior to mounting so that only cross-sectioned projections of interest are present. Such blades for cross-sectioning can be acquired from Electron Microscopy Sciences of Hatfield, Pa. (Cat. #71974). Cross-sectioning is performed in the machine-direction of the sample, and a fresh, previously unused blade should be used for each new cross-sectional cut. The cross-sectioned face can now be mounted so that the projections are directed upward away from the base mount using an adherent such as two-side tape so that it can be viewed using a video camera possessing an optical lens. The mount itself and any background behind the sample that will be viewed by the camera must be darkened using non-reflective black tape and black construction paper 346 (shown in FIG. 25), respectively. For a typical sample, enough cross-sections should be cut and mounted separately from which a total of six projection height values can be determined.

Figure 25:
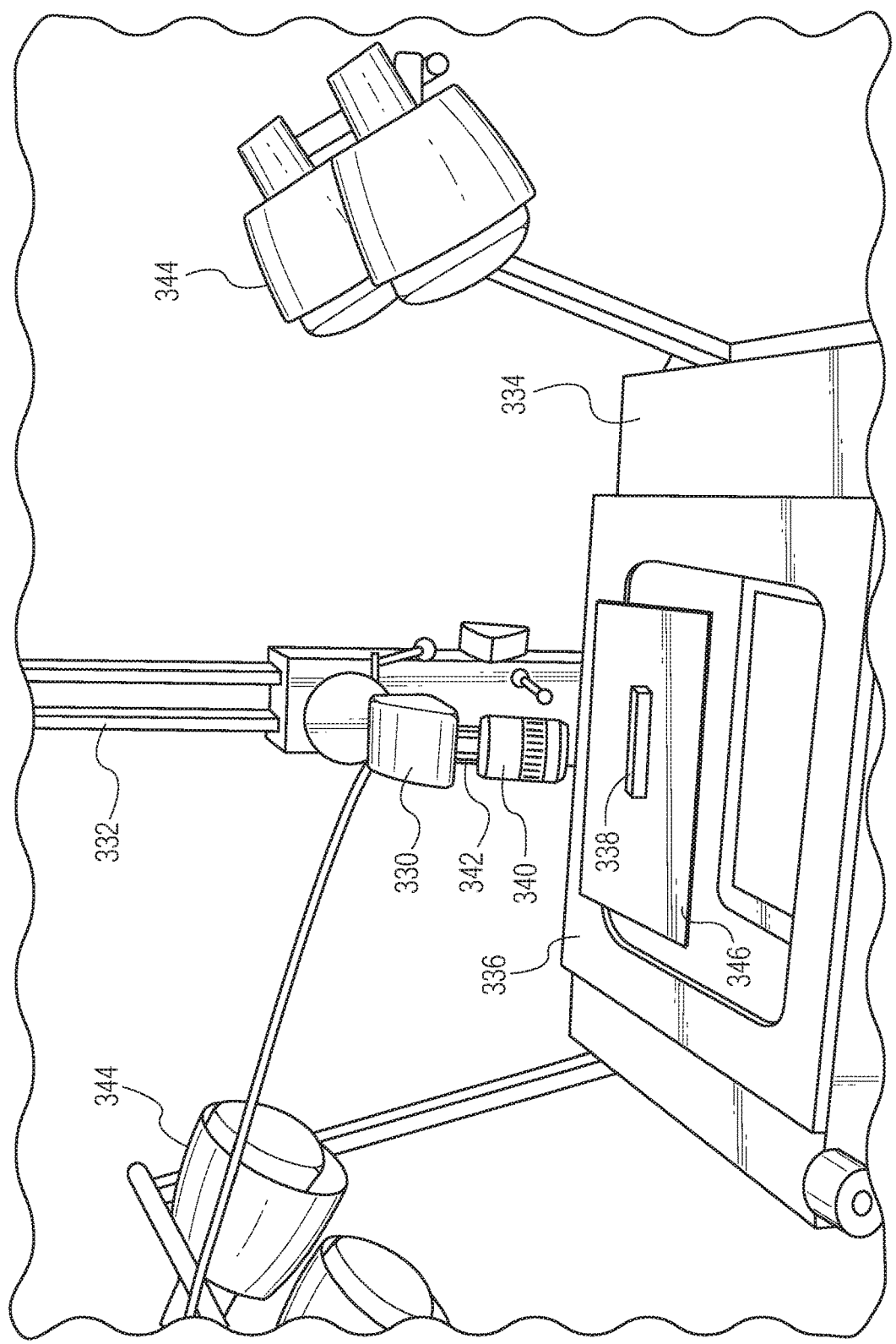
FIG. 25 is a perspective view of an exemplary illustration of a set-up of an imaging system for determining projection height of a fluid entangled laminate web.

An exemplary setup for acquiring the images is representatively illustrated in FIG. 25. Specifically, a CCD video camera 330 (e.g., a Leica DFC 310 FX video camera operated in gray scale mode is available from Leica Microsystems of Heerbrugg, Switzerland) is mounted on a standard support 332 such as a Polaroid MP-4 Land Camera standard support available from Polaroid Resource Center in Cambridge, Miss. or equivalent. The standard support 332 is attached to a macro-viewer 334 such as a KREONITE macro-viewer available from Dunning Photo Equipment, Inc., having an office in Bixby, Okla. An auto stage 336 is placed on the upper surface of the macro-viewer 334. The auto stage 336 is used to move the position of a given sample for viewing by the camera 330. A suitable auto stage 336 is a Model H112, available from Prior Scientific Inc., having an office in Rockland, Mass.

The darkened sample mount 338 exposing the cross-sectioned sample face possessing land areas and projections is placed on the auto stage 336 under the optical axis of a 50 mm Nikon lens 340 with an f-stop setting of 2.8. The Nikon lens 340 is attached to the Leica DFC 310 FX camera 330 using a 30 mm extension tube 342 and a c-mount adaptor. The sample mount 338 is oriented so the sample cross-section faces flush toward the camera 330 and runs in the horizontal direction of the resulting image with the projections directed upward away from the base mount. The cross-sectional face is illuminated with incident, incandescent lighting 344 provided by two, 150 watt, GE Reflector Flood lamps. The two flood lamps are positioned so that they provide more illumination to the cross-sectional face than to the sample mount 338 beneath it in the image. When viewed from overhead directly above the camera 330 and underlying sample cross-section mount 338, the flood lamps 344 will be positioned at approximately 30 degrees and 150 degrees with respect to the horizontal plane running thru the camera 330. From this view the camera support will be at the 90 degree position. The illumination level of the lamps is controlled with a Variable Auto-transformer, type 3PN1010, available from Staco Energy Products Co. having an office in Dayton, Ohio.

The image analysis software platform used to perform measurements is a QWIN Pro (Version 3.5.1) available from Leica Microsystems, having an office in Heerbrugg, Switzerland. The system and images are also calibrated using the QWIN software and a standard ruler with metric markings at least as small as one millimeter. The calibration is performed in the horizontal dimension of the video camera image. Units of millimeters per pixel are used for the calibration.

Thus, the method for determining projection heights of a given sample includes the step of performing several, dimensional measurements. Specifically, an image analysis algorithm is used to acquire and process images as well as perform measurements using Quantimet User Interactive Programming System (QUIPS) language. The image analysis algorithm is reproduced below.

```
NAME = Height – Projection vs Land Regions – 1
PURPOSE = Measures height of projection and land regions
DEFINE VARIABLES & OPEN FILES
  -- The following line is set to designate where measurement data will be stored.
Open File (C:\Data\39291\Height\data.xls, channel #1)
FIELDS = 6
SAMPLE ID AND SET UP
Enter Results Header
File Results Header ( channel #1 )
File Line ( channel #1 )
Measure frame ( x 31, y 61, Width 1330, Height 978 )
Image frame ( x 0, y 0, Width 1392, Height 1040 )
  -- Calvalue = 0.0083 mm/pixel
CALVALUE = 0.0083
Calibrate ( CALVALUE CALUNITS$ per pixel )
For ( REPLICATE = 1 to FIELDS, step 1 )
   Clear Feature Histogram #1
   Clear Feature Histogram #2
   Clear Accepts
   IMAGE ACQUISITION AND DETECTION
   PauseText ( "Position sample, focus image and set white level to 0.95." )
   Image Setup DC Twain [PAUSE] ( Camera 1, AutoExposure Off, Gain 0.00,
   ExposureTime 200.00 msec, Brightness 0, Lamp 49.99 )
   Acquire ( into Image0 )
     ACQOUTPUT = 0
     -- The following line can be optionally set-up for saving image files to a specific
     location.
     ACQFILE$ = "C:\Images\39291 - for Height\Text.
     2H_"+STR$(REPLICATE)+"s.jpg"
   Write image ( from ACQOUTPUT into file ACQFILE$ )
   Detect ( whiter than 104, from Image0 into Binary0 delineated )
   IMAGE PROCESSING
   Binary Amend (Close from Binary0 to Binary1, cycles 4, operator Disc, edge erode on)
   Binary Amend (Open from Binary1 to Binary2, cycles 4, operator Disc, edge erode on)
   Binary Identify (FillHoles from Binary2 to Binary3)
   Binary Amend (Close from Binary3 to Binary4, cycles 15, operator Disc, edge erode on)
   Binary Amend (Open from Binary4 to Binary5, cycles 20, operator Disc, edge erode on)
   PauseText ( "Fill in projection & land regions that should be included, and reject over
   detected regions." )
   Binary Edit [PAUSE] ( Draw from Binary5 to Binary6, nib Fill, width 2 )
   PauseText ( "Select 'Land' region for measurement." )
   Binary Edit [PAUSE] (Accept from Binary6 to Binary7, nib Fill, width 2 )
   PauseText ( "Select 'Projection' region for measurement." )
   Binary Edit [PAUSE] ( Accept from Binary6 to Binary8, nib Fill, width 2 )
   -- Combine land and projection regions with measurement grid.
   Graphics ( Grid, 30 x 0 Lines, Grid Size 1334 × 964, Origin 21 × 21, Thickness 2,
   Orientation 0.000000, to Binary15 Cleared )
   Binary Logical (C = A AND B : C Binary10, A Binary7, B Binary15)
   Binary Logical (C = A AND B : C Binary11, A Binary8, B Binary15)
   MEASURE HEIGHTS
   -- Land region only
   Measure feature (plane Binary10, 8 ferets, minimum area: 8, grey image: Image0 )
      Selected parameters: X FCP, Y FCP, Feret90
   Feature Histogram #1 ( Y Param Number, X Param Feret90, from 0.0100 to 5.,
      logarithmic, 20 bins )
   Display Feature Histogram Results ( #1, horizontal, differential, bins + graph (Y axis
   linear), statistics ) Data Window ( 1278, 412, 323, 371 )
   -- Projection regions only (includes any underlying land material)
   Measure feature ( plane Binary11,8 ferets, minimum area: 8, grey image: Image0 )
      Selected parameters: X FCP, Y FCP, Feret90
   Feature Histogram #2 ( Y Param Number, X Param Feret90, from 0.0100 to 10.,
      logarithmic, 20 bins )
   Display Feature Histogram Results ( #2, horizontal, differential, bins + graph (Y axis
   linear), statistics ) Data Window ( 1305, 801, 297, 371 )
   OUTPUT DATA
   File ( "Land Height (mm)", channel #1 )
   File Line ( channel #1 )
   File Feature Histogram Results ( #1, differential, statistics, bin details, channel #1 )
   File Line ( channel #1 )
   File Line ( channel #1 )
   File ( "Projection + Land Height (mm)", channel #1 )
   File Line ( channel #1 )
```

-continued

```
   File Feature Histogram Results ( #2, differential, statistics, bin details, channel #1 )
      File Line ( channel #1 )
      File Line ( channel #1 )
      File Line ( channel #1 )
Next ( REPLICATE )
Close File (channel #1)
END
```

The QUIPS algorithm is executed using the QWIN Pro software platform. The analyst is initially prompted to enter sample identification information which is sent to a designated EXCEL file to which the measurement data will also be subsequently sent.

The analyst is then prompted to position the mounted sample cross-section on the auto-stage 336 possessing the darkened background so the cross-sectional face is flush to the camera 330 with projections directed upward and the length running horizontally in the live image displayed on the video monitor screen. The analyst next adjusts the video camera 330 and lens' 340 vertical position to optimize the focus of the cross-sectional face. The illumination level is also adjusted by the analyst via the Variable Auto-transformer to a white level reading of approximately 0.95.

Once the analyst completes the above steps and executes the continue command, an image will be acquired, detected and processed automatically by the QUIPS algorithm. The analyst will then be prompted to fill-in the detected binary image, using the computer mouse, of any projection and/or land areas shown in the cross-sectional image that should have been included by the previous detection and image processing steps as well as rejecting any over detected regions that go beyond the boundaries of the cross-sectional structure shown in the underlying gray-scale image. To aid in this editing process, the analyst can toggle the 'control' and 'B' keys on the keyboard simultaneously to turn the overlying binary image on and off to assess how closely the binary matches with the boundaries of the sample shown in the cross-section. If the initial cross-sectioning sample preparation was performed well, little if any manual editing should be required.

The analyst is now prompted to "Select 'Land' region for measurement" using the computer mouse. This selection is performed by carefully drawing a vertical line down through one side of a single land area located between or adjacent to projections and then, with the left mouse button still depressed, moving the cursor beneath the land area to its opposite side and then drawing another vertical line upward. Once this has occurred, the left mouse button can be released and the land area to be measured should be filled in with a green coloring. If the vertical edges of the resulting selected region are skewed in any way, the analyst can reset to the original detected binary by clicking on the 'Undo' button located within the Binary Edit window and begin the selection process again until straight vertical edges on both sides of the selected land region are obtained.

Similarly, the analyst will next be prompted to "Select 'Projection' region for measurement." The top portion of a projection region adjacent to the previously selected land area is now selected in the same manner that was previously described for a land area selection.

The algorithm will then automatically perform measurements on both selected regions and output the data, in histogram format, into the designated EXCEL spreadsheet file. In the EXCEL file, the histograms for land and projection regions will be labeled "Land Height (mm)" and "Projection+Land Height (mm)," respectively. A separate set of histograms will be generated for each selection of land and projection region pairs.

The analyst will then again be prompted to position the sample and begin the process of selecting different land and projection regions. At this point, the analyst can either use the auto-stage joystick to move the same cross-section to a new sub-sampling position or an entirely different mounted cross-section obtained from the same sample can be positioned on the auto-stage 306 for measurement. The process for positioning the sample and selecting land and projection regions for measurement will occur six times for each execution of the QUIPS algorithm.

A single projection height value is then determined by calculating the numerical difference between the mean values of the separate land and projection region histograms for each single pair of measurements. The QUIPS algorithm will provide six replicate measurement sets of both land and projection regions for a single sample so that six projection height values will be generated per sample. The final sample mean spread value is usually based on an N=6 analysis from six, separate subsample measurements. A comparison between different samples can be performed using a Student's T analysis at the 90% confidence level.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a) a longitudinal direction and a transverse direction;
   b) a longitudinal centerline and a transverse centerline;
   c) an anterior region, a posterior region, and a central region positioned between the anterior region and the posterior region;
   d) an anterior region transverse direction end edge, a posterior region transverse direction end edge, and a pair of longitudinal direction side edges extending between and connecting the anterior region transverse direction end edge and a posterior region transverse direction end edge;
   e) a topsheet layer defining a body facing surface of the absorbent article, a liquid impermeable layer defining a garment facing surface of the absorbent article, and an absorbent core positioned between the topsheet layer and the liquid impermeable layer; and
   f) an exudate management layer in fluid communication with the topsheet layer, the exudate management layer comprising a first component comprising an outer peripheral edge and an opening in the exudate management layer, the opening located inward from the outer peripheral edge and having a perimeter partially defined by an inner edge of the first component; and a second component connected to the first component via a primary fold, the primary fold defining a remaining perimeter of the opening, and the second component extending from the primary fold such that a portion overlaps or underlaps with the first component and a remaining portion extends past the outer peripheral edge.

2. The absorbent article of claim 1 wherein the exudate management layer is positioned on the body facing surface of the topsheet layer.

3. The absorbent article of claim 1 wherein the exudate management layer is positioned between the topsheet layer and the absorbent core.

4. The absorbent article of claim 1 further comprising an acquisition layer positioned between the topsheet layer and the absorbent core.

5. The absorbent article of claim 1 wherein the opening is positioned between the transverse centerline and the posterior region transverse direction end edge.

6. The absorbent article of claim 1 wherein the secondary component extends from the primary fold in the longitudinal direction towards the posterior region of the absorbent article.

7. The absorbent article of claim 1 wherein the second component comprises a secondary fold on the remaining portion past the outer peripheral edge.

8. The absorbent article of claim 1 wherein the secondary component is divided into a first secondary component and a second secondary component such that the primary fold comprises a first primary fold and a second primary fold on opposing portions of the remaining perimeter, the first secondary component extending from the first primary fold such that the portion overlaps or underlaps with the first component and the remaining portion extends past the outer peripheral edge and the second secondary component extending from the second primary fold such that the portion overlaps or underlaps with the first component and the remaining portion extends past the outer peripheral edge in an opposing direction.

9. The absorbent article of claim 8 wherein the first secondary component extends from the first primary fold in the longitudinal direction toward the posterior region of the absorbent article and the second secondary component extends from the second primary fold in the longitudinal direction towards the anterior region of the absorbent article.

10. The absorbent article of claim 1 wherein the absorbent article further comprises an opposing pair of containment flaps extending in the longitudinal direction of the absorbent article.

11. The absorbent article of claim 1 wherein the topsheet layer is a fluid entangled laminate web comprising a support layer comprising a plurality of fibers and opposed first and second surfaces; a projection layer comprising a plurality of fibers and opposed inner and outer surfaces, the second surface of the support layer in contact with the inner surface of the projection layer, fibers of at least one of the support layer and the projection layer being fluid-entangled fibers of the other of the support layer and the projection layer; a plurality of hollow projections formed form a first plurality of the plurality of fibers in the projection layer, the plurality of hollow projections extending from the outer surface of the projection layer in a direction away from the support layer; and a land area, wherein the plurality of hollow projections are surrounded by the land area.

12. The absorbent article of claim 1 wherein the absorbent core comprises a body facing surface and projections extending away from the body facing surface of the absorbent core.

13. The absorbent article of claim 1 wherein the second component comprises at least one opening.

* * * * *